US012797375B2

(12) United States Patent
Chavan et al.

(10) Patent No.: US 12,797,375 B2
(45) Date of Patent: Nov. 17, 2026

(54) MODULATION OF DRUG-DRUG INTERACTIONS OF VADADUSTAT

(71) Applicant: Akebia Therapeutics, Inc., Cambridge, MA (US)

(72) Inventors: Ajit Chavan, Cambridge, MA (US); Steven Burke, Cambridge, MA (US)

(73) Assignee: Akebia Therapeutics, Inc., Cambridge, MA (US)

( * ) Notice: Subject to any disclaimer, the term of this patent is extended or adjusted under 35 U.S.C. 154(b) by 324 days.

(21) Appl. No.: 18/279,680

(22) PCT Filed: Feb. 28, 2022

(86) PCT No.: PCT/US2022/018152

§ 371 (c)(1),
(2) Date: Aug. 31, 2023

(87) PCT Pub. No.: WO2022/187142

PCT Pub. Date: Sep. 9, 2022

(65) Prior Publication Data

US 2024/0148707 A1 May 9, 2024

Related U.S. Application Data

(60) Provisional application No. 63/155,022, filed on Mar. 1, 2021.

(51) Int. Cl.

| | |
|---|---|
| ***A61K 31/44*** | (2006.01) |
| ***A61K 31/785*** | (2006.01) |
| ***A61K 45/06*** | (2006.01) |
| ***A61P 7/06*** | (2006.01) |

(52) U.S. Cl.

CPC ............ *A61K 31/44* (2013.01); *A61K 31/785* (2013.01); *A61K 45/06* (2013.01); *A61P 7/06* (2018.01)

(58) Field of Classification Search

CPC .............................. A61K 31/44; A61K 31/785
USPC ......................................................... 514/355
See application file for complete search history.

(56) References Cited

U.S. PATENT DOCUMENTS

| | | | |
|---|---|---|---|
| 2007/0299086 | A1 | 12/2007 | Kawamoto |
| 2012/0309977 | A1 | 12/2012 | Lanthier et al. |
| 2013/0085121 | A1 | 4/2013 | Wang et al. |
| 2014/0057892 | A1 | 2/2014 | Kawamoto et al. |
| 2016/0143891 | A1 | 5/2016 | Shalwitz et al. |
| 2018/0092892 | A1 | 4/2018 | Smith et al. |
| 2020/0368223 | A1 | 11/2020 | King |
| 2023/0071553 | A1 | 3/2023 | Smith et al. |
| 2023/0263786 | A1 | 8/2023 | Chavan et al. |

FOREIGN PATENT DOCUMENTS

| | | | |
|---|---|---|---|
| JP | 2016537365 | A | 12/2016 |
| KR | 20160083118 | A | 7/2016 |
| TW | 201605801 | A | 2/2016 |
| WO | 2008002576 | A2 | 1/2008 |
| WO | 2014168986 | A1 | 10/2014 |
| WO | 2014200773 | A2 | 12/2014 |
| WO | 2015073779 | A1 | 5/2015 |
| WO | 2016161094 | A1 | 10/2016 |
| WO | 2021257800 | A1 | 12/2021 |
| WO | 2022187142 | A1 | 9/2022 |

OTHER PUBLICATIONS

Clinicaltrials.gov, Archive No. NCT01235936, Aug. 30, 2012, retrieved Dec. 1, 2014 from URL: http://clinicaltrials.gov/archive/NCT01235936/2012_09_30 (3 pages).
International Search Report for PCT/US2021/037781 dated Oct. 15, 2021 (6 pages).
International Search Report for PCT/US2022/018152 dated Jun. 14, 2022 (5 pages).
"Akebia Closes $41 Million Series C", Triathlon Medical Ventures, Jun. 4, 2013, retrieved Dec. 1, 2014 from URL: http://www.tmvp.com/news_Akebia_06042013.html, (2 pages).
Chavan, et al., "Pharmacokinetic Evaluation of Drug Interactions Between Vadadustat and HMG-CoA Reductase Inhibitors (Statins)", EMBASE / Elsevier, Oct. 2020, Database Accession No. EMB-633697266, Conference Abstract (2 pages).
Haase, et al., "Effects of vadadustat on hemoglobin concentrations in patients receiving hemodialysis previously treated with erythropoiesis-stimulating agents", Nephrology, dialysis, transplantation: official publication of the European Dialysis and Transplant Association—European Renal Association, vol. 34, No. 1, Jan. 1, 2019, pp. 90-99, DOI:10.1093/ndt/gfy055 (10 pages).
Markham, "Vadadustat: First Approval", Drugs, vol. 80, Aug. 27, 2020, pp. 1365-1371, DOI: 10.1007/s40265-020-01383-z, (7 pages).
Pasqualetti, et al., "Circadian rhythm of serum erythropoietin in myelodysplastic syndromes", European Review for Medical and Pharmacological Sciences, vol. 4, 2000, pp. 111-115 (5 pages).
PMDA, "Report on the Deliberation Results", Pharmaceuticals and Medical Devices Agency (PMDA), Jun. 4, 2020 (99 pages).
Qunibi, et al., "A randomized controlled trial comparing intravenous ferric carboxymaltose with oral iron for treatment of iron deficiency anaemia of non-dialysis-dependent chronic kidney disease patients", Nephrology Dialysis Transplantation, vol. 26, No. 5, May 2011, pp. 1599-1607, DOI: 10.1093/ndt/gfq613, (9 pages).
Stohlawetz, et al., "Effects of erythropoietin on platelet reactivity and thrombopoiesis in humans", Blood, vol. 95, No. 9, May 1, 2000, pp. 2983-2989 (7 pages).
"Study in Healthy Adult Subjects to Assess the Effect of Phosphate Binders on the Pharmacokinetics of Single Dose of Vadadustat", ClinicalTrials.gov, Study Details: NCT04299633, Oct. 8, 2020 (9 pages).

(Continued)

*Primary Examiner* — Raymond J Henley, III
(74) *Attorney, Agent, or Firm* — Proskauer Rose LLP

(57) ABSTRACT

Provided herein are methods for reducing, minimizing, or controlling drug-drug interactions resulting from administration of a drug (e.g., a first drug) that is vadadustat (i.e., {[5-(3-chlorophenyl)-3-hydroxypyridine-2-carbonyl] amino}acetic acid (Compound 1)) and another (e.g., a second) drug (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)).

26 Claims, 8 Drawing Sheets

(56) References Cited

OTHER PUBLICATIONS

Kuriyama, Satoru , et al., "A new insight into the treatment of renal anemia with HIF stabilizer", Renal Replacement Therapy, 2020, vol. 6, No. 63 (14 pages).
Lentini, Silvia, et al., "Effects of oral iron and calcium supplement on the pharmacokinetics and pharmacodynamics of molidustat: an oral HIF-PH inhibitor for the treatment of renal anaemia", European Journal of Clinical Pharmacology, 2020 (pp. 185-197).
Martin , et al., "Clinical Trial of Vadadustat in Patients with Anemia Secondary to Stage 3 or 4 Chronic Kidney Disease", American journal of nephrology, vol. 45, No. 5, May 25, 2017, pp. 380-388, doi:10.1159/000464476 (15 pages).
Pai, et al., "Iron-based phosphate binders—a new element in management of hyperphosphatemia", Expert Opinion on Drug Metabolism & Toxicology, vol. 12, No. 1, 2016, pp. 115-127, DOI:10.1517/17425255.2016.1110573 (14 pages).
Tsushinsha, Iyaku , "New drug explanation: Focusing on the oral treatment for renal anemia (HIF-PH inhibitor) 'Vafseo tablets (Tanabe Pharma Corporation)'", https://iyakutsushinsha.com/2020/10/19, Oct. 19, 2020 (2 pages).
Ruospo, Marinella , et al., "Phosphate binders for preventing and treating chronic kidney disease-mineral and bone disorder (CKD-MBD)", Cochrane Database of Systematic Reviews, Aug. 22, 2018, vol. 2018, No. 8 (296 pages).
Shah, Pankaj B., et al., "Diuretics for people with chronic kidney disease", Cochrane Database of Systematic Reviews, Oct. 26, 2017, vol. 2017, No. 10 (4 pages).
Daoud, Kirollos , et al., "The Role of Iron-Based Phosphate Binder in the Treatment of Hyperphosphatemia", Nephrology Nursing Journal, Apr. 2023, vol. 50, No. 2 (pp. 140-144).

MODULATION OF DRUG-DRUG INTERACTIONS OF VADADUSTAT

CROSS-REFERENCE TO RELATED APPLICATIONS

The present application is a 35 U.S.C. § 371 National Stage Application of International Application No. PCT/US2022/018152, filed on Feb. 28, 2022, which claims benefit of U.S. Provisional Application No. 63/155,022, filed Mar. 1, 2021, each of which is incorporated herein by reference in its entirety.

BACKGROUND OF THE INVENTION

{[5-(3-chlorophenyl)-3-hydroxypyridine-2-carbonyl] amino}acetic acid (Vadadustat, Code: AKB-6548, Compound 1), having a chemical formula:

Compound 1

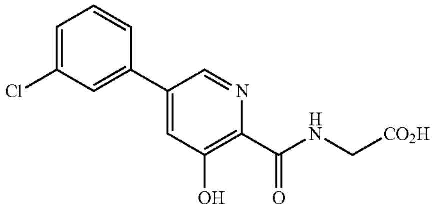

is prolyl hydroxylase inhibitor, and may be administered to subjects to treat or prevent diseases ameliorated by modulation of hypoxia-inducible factor (HIF) prolyl hydroxylase (e.g., Peripheral Vascular Disease (PVD), Coronary Artery Disease (CAD), heart failure, ischemia, hypoxia, and anemia). For some subjects receiving Compound 1, this compound may be administered as part of a therapeutic regimen that includes other medications and therapeutic agents. For example, some subjects being administered Compound 1 also require therapeutic agents such as phosphate binders (e.g., a polymeric amine that binds phosphate); or inhibitors and/or substrates of certain proteins, receptors and/or transporters (e.g., probenecid, cyclosporine, rifampin, digoxin, or adefovir). The bioavailability of Compound 1 and/or the other medications and therapeutic agents (e.g., phosphate binders, probenecid, cyclosporine, rifampin, digoxin, or adefovir) potentially may be affected when co-administered to the subjects. For example, some subjects being administered Compound 1 also require phosphate binders (e.g., a polymeric amine that binds phosphate) to control serum phosphorus levels. Phosphate binders potentially may reduce the bioavailability of Compound 1. Accordingly, new methods are needed for controlling any such drug-drug interactions when administering Compound 1 with other medications and therapeutic agents so as not to adversely impact the therapeutic effects of an administered drug or to adversely impact a subject.

SUMMARY

The invention is based, in part, on the surprising discovery of new therapeutic regimens that result in the modulation of drug-drug interactions (e.g., preventing, controlling, reducing, or minimizing drug-drug interactions) between a first drug that is vadadustat and a second drug (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)). Such regimens can have beneficial outcomes for a patient, including those described herein.

In one aspect, the present invention provides herein a method of preventing, controlling, reducing, or minimizing drug-drug interaction between a first drug and a second drug comprising administering to a subject:

(a) an effective amount of the first drug or a pharmaceutical composition comprising an effective amount of the first drug, wherein the first drug is {[5-(3-chlorophenyl)-3-hydroxypyridine-2-carbonyl]amino}acetic acid; and (b) an effective amount of the second drug, wherein the second drug comprises a polymeric amine that binds phosphate, wherein the subject has renal anemia (anemia secondary to or associated with chronic kidney disease), and wherein (a) is given at least 2 hours before and/or after taking (b).

In another aspect, the present invention provides herein a method of preventing, controlling, reducing, or minimizing drug-drug interaction between a first drug and a second drug comprising administering to a subject:

(a) an effective amount of the first drug or a pharmaceutical composition comprising an effective amount of the first drug, wherein the first drug is {[5-(3-chlorophenyl)-3-hydroxypyridine-2-carbonyl]amino}acetic acid; and (b) an effective amount of the second drug, wherein the second drug comprises a polymeric amine that binds phosphate, wherein the subject has renal anemia (anemia secondary to or associated with chronic kidney disease), and wherein (a) is given at least 1 hour before and/or after taking (b).

In another aspect, the present invention provides a method of increasing or maintaining bioavailability of a drug comprising administering to the subject:

(a) an effective amount of a drug or a pharmaceutical composition comprising an effective amount of the drug, wherein the drug is {[5-(3-chlorophenyl)-3-hydroxypyridine-2-carbonyl]amino}acetic acid; and (b) an effective amount of a drug that is a composition comprising a polymeric amine that binds to phosphate, wherein the subject has renal anemia (anemia secondary to or associated with chronic kidney disease), and wherein (a) is given at least 2 hours before and/or after taking (b).

In another aspect, the present invention provides a method of increasing or maintaining bioavailability of a drug comprising administering to the subject:

(a) an effective amount of the drug or a pharmaceutical composition comprising an effective amount of the drug, wherein the drug is {[5-(3-chlorophenyl)-3-hydroxypyridine-2-carbonyl]amino}acetic acid; and (b) an effective amount of a drug that is a composition comprising a polymeric amine that binds to phosphate, wherein the subject has renal anemia (anemia secondary to or associated with chronic kidney disease), and wherein (a) is given at least 1 hour before and/or after taking (b).

In another aspect, the present invention provides a method of minimizing, controlling, or preventing a decrease in the absorption of a drug comprising administering to the subject:

(a) an effective amount of a drug or a pharmaceutical composition comprising an effective amount of the drug, wherein the drug is {[5-(3-chlorophenyl)-3-hydroxypyridine-2-carbonyl]amino}acetic acid; and (b) an effective amount of a drug that is a composition comprising a polymeric amine that binds to phosphate, wherein the subject has renal anemia (anemia secondary to or associated with chronic kidney disease), and wherein (a) is given at least 2 hours before and/or after taking (b).

In another aspect, the present invention provides a method of minimizing, controlling, or preventing a decrease in the absorption of a drug comprising administering to the subject:

(a) an effective amount of the drug or a pharmaceutical composition comprising an effective amount of the drug, wherein the drug is {[5-(3-chlorophenyl)-3-hydroxypyridine-2-carbonyl]amino}acetic acid; and (b) an effective amount of a drug that is a composition comprising a polymeric amine that binds to phosphate, wherein the subject has renal anemia (anemia secondary to or associated with chronic kidney disease), and wherein (a) is given at least 1 hour before and/or after taking (b).

In embodiments, (b) is a sevelamer hydrochloride or sevelamer carbonate.

In embodiments, (b) is a sevelamer hydrochloride.

In embodiments, (b) is a sevelamer carbonate.

In embodiments, (b) is administered as a tablet.

In embodiments, (b) is administered as a powder.

In embodiments, the first drug is given at least 1 hour before taking the second drug.

In embodiments, the first drug is given at least 2 hours after taking the second drug.

In embodiments, (a) is given at least 1 hour before taking (b), wherein (b) is a sevelamer hydrochloride or sevelamer carbonate.

In embodiments, (a) is given at least 2 hours after taking (b), wherein (b) is a sevelamer hydrochloride or sevelamer carbonate.

In another aspect, the present invention provides a method of reducing or minimizing drug-drug interaction between a first drug and a second drug comprising administering to a subject:

(a) an effective amount of the first drug or a pharmaceutical composition comprising an effective amount of the first drug, wherein the first drug is {[5-(3-chlorophenyl)-3-hydroxypyridine-2-carbonyl]amino}acetic acid (Compound 1); and (b) an effective amount of the second drug, wherein the second drug is an OAT1/OAT3 inhibitor, wherein the subject has renal anemia (anemia secondary to or associated with chronic kidney disease), and wherein the amount of (a) is adjusted compared to the amount when administered in the absence of (b) or in monotherapy.

In another aspect, the present invention provides a method of preventing drug-drug interaction between a first drug and a second drug comprising administering to a subject:

(a) an effective amount of the first drug or a pharmaceutical composition comprising an effective amount of the first drug, wherein the first drug is {[5-(3-chlorophenyl)-3-hydroxypyridine-2-carbonyl]amino}acetic acid (Compound 1); and (b) an effective amount of the second drug, wherein the second drug is an OAT1/OAT3 inhibitor, wherein the subject has renal anemia (anemia secondary to or associated with chronic kidney disease), and wherein the amount of (a) is adjusted compared to the amount when administered in the absence of (b) or in monotherapy.

In another aspect, the present invention provides a method of controlling drug-drug interaction between a first drug and a second drug comprising administering to a subject:

(a) an effective amount of the first drug or a pharmaceutical composition comprising an effective amount of the first drug, wherein the first drug is {[5-(3-chlorophenyl)-3-hydroxypyridine-2-carbonyl]amino}acetic acid (Compound 1); and (b) an effective amount of the second drug, wherein the second drug is an OAT1/OAT3 inhibitor, wherein the subject has renal anemia (anemia secondary to or associated with chronic kidney disease), and wherein the amount of (a) is adjusted compared to the amount when administered in the absence of (b) or in monotherapy.

In another aspect, the present invention provides a method of maintaining bioavailability of a drug comprising administering to the subject:

(a) an effective amount of a drug or a pharmaceutical composition comprising an effective amount of the drug, wherein the drug is {[5-(3-chlorophenyl)-3-hydroxypyridine-2-carbonyl]amino}acetic acid (Compound 1); and (b) an effective amount of the second drug, wherein the second drug is an OAT1/OAT3 inhibitor, wherein the subject has renal anemia (anemia secondary to or associated with chronic kidney disease), and wherein the amount of (a) is adjusted compared to the amount when administered in the absence of (b) or in monotherapy.

In another aspect, the present invention provides a method of minimizing an increase in exposure to a drug comprising administering to a subject:

(a) an effective amount of a drug or a pharmaceutical composition comprising an effective amount of the drug, wherein the drug is {[5-(3-chlorophenyl)-3-hydroxypyridine-2-carbonyl]amino}acetic acid (Compound 1); and (b) an effective amount of the second drug, wherein the second drug is an OAT1/OAT3 inhibitor, wherein the subject has renal anemia (anemia secondary to or associated with chronic kidney disease), and wherein the amount of (a) is adjusted compared to the amount when administered in the absence of (b) or in monotherapy.

In another aspect, the present invention provides a method of preventing an increase in exposure to a drug comprising administering to a subject:

(a) an effective amount of a drug or a pharmaceutical composition comprising an effective amount of the drug, wherein the drug is {[5-(3-chlorophenyl)-3-hydroxypyridine-2-carbonyl]amino}acetic acid (Compound 1); and (b) an effective amount of the second drug, wherein the second drug is an OAT1/OAT3 inhibitor, wherein the subject has renal anemia (anemia secondary to or associated with chronic kidney disease), and wherein the amount of (a) is adjusted compared to the amount when administered in the absence of (b) or in monotherapy.

In another aspect, the present invention provides a method of controlling an increase in exposure to a drug comprising administering to a subject:

(a) an effective amount of a drug or a pharmaceutical composition comprising an effective amount of the drug, wherein the drug is {[5-(3-chlorophenyl)-3-hydroxypyridine-2-carbonyl]amino}acetic acid (Compound 1); and (b) an effective amount of the second drug, wherein the second drug is an OAT1/OAT3 inhibitor, wherein the subject has renal anemia (anemia secondary to or associated with chronic kidney disease), and wherein the amount of (a) is adjusted compared to the amount when administered in the absence of (b) or in monotherapy.

In embodiments, the subject is at risk of or has gout or gouty arthritis.

In embodiments, (b) is probenecid.

In embodiments, (b) is administered as a tablet.

In embodiments, the amount of (a) is decreased compared to the amount when administered in the absence of (b) or in monotherapy.

In embodiments, the amount of (a) is decreased by about 20% to about 80% compared to the amount when administered in the absence of (b) or in monotherapy.

In embodiments, the amount of (a) is decreased by about 40% to about 60% compared to the amount when administered in the absence of (b) or in monotherapy.

In another aspect, the present invention provides a method of treating renal anemia (anemia secondary to or associated with chronic kidney disease), comprising administering to a subject having renal anemia an effective amount of a compound which is {[5-(3-chlorophenyl)-3-hydroxypyridine-2-carbonyl]amino}acetic acid or pharmaceutically acceptable salt, solvate, or hydrate thereof, wherein the compound is for administering together with a composition comprising a polymeric amine selected from sevelamer hydrochloride and sevelamer carbonate.

In embodiments, the compound which is {[5-(3-chlorophenyl)-3-hydroxypyridine-2-carbonyl]amino}acetic acid or pharmaceutically acceptable salt, solvate, or hydrate thereof, is administered at least 1 hour before administering the composition comprising a polymeric amine selected from sevelamer hydrochloride or sevelamer carbonate.

In embodiments, the compound which is {[5-(3-chlorophenyl)-3-hydroxypyridine-2-carbonyl]amino}acetic acid or pharmaceutically acceptable salt, solvate, or hydrate thereof, is administered at least 2 hours after administering the composition comprising a polymeric amine selected from sevelamer hydrochloride or sevelamer carbonate.

In another aspect, the present invention provides a method of treating renal anemia (anemia secondary to or associated with chronic kidney disease), comprising administering to a subject having renal anemia an effective amount of a compound which is {[5-(3-chlorophenyl)-3-hydroxypyridine-2-carbonyl]amino}acetic acid or pharmaceutically acceptable salt, solvate, or hydrate thereof, wherein the compound is for administering together with an OAT1/OAT3 inhibitor that is probenecid.

In embodiments, the amount off{[5-(3-chlorophenyl)-3-hydroxypyridine-2-carbonyl]amino}acetic acid or pharmaceutically acceptable salt, solvate, or hydrate thereof, is decreased compared to the amount when administered in the absence of an OAT1/OAT3 inhibitor that is probenecid or in monotherapy.

DETAILED DESCRIPTION

Figure 1:
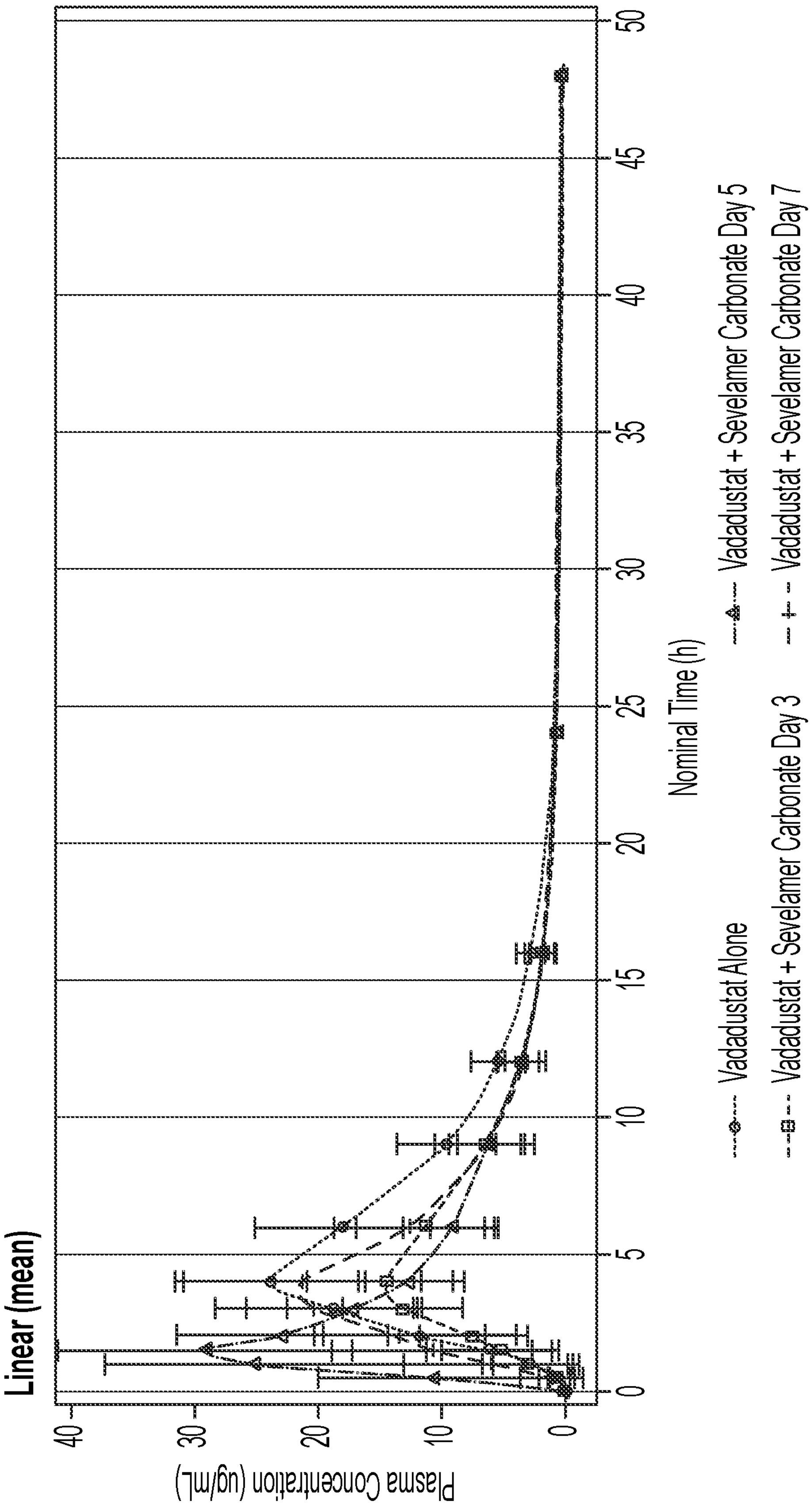
FIG. 1 shows mean (SD) plasma concentration of vadadustat when 1) administered alone; 2) administered concomitantly with sevelamer carbonate (Day 3); 3) administered 1 hour before sevelamer carbonate (Day 5); administered 2 hours after sevelamer carbonate (Day 7).

Vadadustat ({[5-(3-chlorophenyl)-3-hydroxypyridine-2-carbonyl]amino}acetic acid; (Compound 1)) is a Hypoxia Inducible Factor Prolyl Hydroxylase inhibitor (HIF-PH inhibitor).

Compound 1

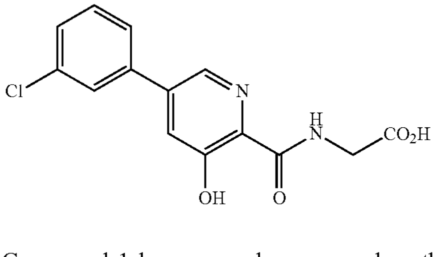

Compound 1 has emerged as a new drug that is highly useful for treating or preventing renal anemia (anemia secondary to or associated with chronic kidney disease).

A subject with renal anemia (anemia secondary to or associated with chronic kidney disease) may be receiving other therapeutic agents concurrently with a vadadustat treatment regimen (e.g., to treat co-morbid conditions or to treat complications associated with chronic kidney disease or the renal anemia (anemia secondary to or associated with chronic kidney disease)). In particular, drug-drug interactions may occur when a patient is administered Compound 1 in combination with another drug (e.g., a drug comprising a polymeric amine that binds phosphate (e.g., sevelamer-based binding agents such as sevelamer hydrochloride or sevelamer carbonate); or inhibitors and/or substrates of certain proteins, receptors, and/or transporters (e.g., probenecid, cyclosporine, rifampin, digoxin, or adefovir)). For example, administration of Compound 1 together with a composition comprising polymeric amines can cause a drug-drug interaction between Compound 1 and the polymeric amine.

A drug-drug interaction can manifest in various ways, including affecting pharmaceutical interactions, pharmacokinetic interactions, pharmacodynamic interactions, absorption, distribution, metabolism, or excretion. For example, a drug-drug interaction may adversely impact bioavailability and/or absorption of Compound 1 and/or the other therapeutic agent (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)). In other embodiments, still other side-effects may result. Accordingly, modulation of a drug-drug interaction will be highly beneficial to achieving successful treatment of subject with chronic kidney disease or the renal anemia (anemia secondary to or associated with chronic kidney disease).

Provided herein are methods for reducing, minimizing, or controlling the drug-drug interactions resulting from administration of Compound 1 and other therapeutic agents (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)) to a subject. Also provided herein are methods for increasing the bioavailability of Compound 1, wherein Compound 1 and certain drugs (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)) are administered to a subject.

In particular, provided herein are methods for reducing, minimizing, or controlling the drug-drug interactions resulting from administration of Compound 1 and other therapeutic agents, including drugs comprising a polymeric amine that binds phosphates (e.g., sevelamer hydrochloride or sevelamer carbonate) to a subject. Also provided herein are methods for increasing the bioavailability of Compound 1, wherein Compound 1 and certain drugs comprising a polymeric amine (e.g., sevelamer hydrochloride or sevelamer carbonate) are administered to a subject.

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference for all purposes.

Animal: As used herein, the term "animal" refers to any member of the animal kingdom. In some embodiments, "animal" refers to humans, at any stage of development. In some embodiments, "animal" refers to non-human animals, at any stage of development. In embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Dose(s): As used herein, the term "dose(s)" means a quantity of the compound or a pharmaceutically acceptable salt, solvate, or hydrate thereof to be administered at one time. A dose may comprise a single unit dosage form, or alternatively may comprise more than a single unit dosage form (e.g., a single dose may comprise two tablets), or even less than a single unit dosage form (e.g., a single dose may comprise half of a tablet).

Daily dose: As used herein, the term "daily dose" means a quantity of the compound, or a pharmaceutically acceptable salt, solvate, or hydrate thereof that is administered in a 24-hour period. Accordingly, a daily dose may be administered all at once (i.e., once daily dosing) or alternatively the daily dosing may be divided such that administration of the compound is twice daily, three times daily, or even four times daily.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable", as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in J. Pharmaceutical Sciences (1977) 66:1-19.

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{-alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate, and aryl sulfonate. Further pharmaceutically acceptable salts include salts formed from the quarternization of an amine using an appropriate electrophile, e.g., an alkyl halide, to form a quarternized alkylated amino salt.

Preventing: The term "prevent," "preventing," or "prevention," as used herein refers to an effect that mitigates an undesired effect, e.g., an undesirable drug-drug interaction. Prevention does not require the 100% elimination of the possibility of an event. Rather, it denotes that the likelihood of the occurrence of the event has been reduced by the compound or method.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one-unit dose.

Treating: As used herein, the term "treat," "treatment," or "treating" refers to any method used to partially or completely alleviate, ameliorate, relieve, inhibit, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

As used herein, the term "HIF prolyl hydroxylase" is art-recognized and may be abbreviated as "PHD". HIF prolyl hydroxylase is also known as "prolyl hydroxylase domain-containing protein" which may be abbreviated as "PHD". In this regard, there are three different PHD isoforms, PHD1, PHD2, and PHD3, also referred to as EGLN2, EGLN1, and EGLN3, or HPH3, HPH2, and HPH1, respectively.

As used herein, the term "unit dosage form(s)" includes tablets; caplets; capsules, such as soft elastic gelatin capsules; sachets; cachets; troches; lozenges; dispersions; powders; solutions; gels; liquid dosage forms suitable for oral or mucosal administration to a patient, including suspensions (e.g., aqueous or non-aqueous liquid suspensions), emulsions (e.g., oil-in-water emulsions, or a water-in-oil liquid emulsion), solutions, and elixirs; and sterile solids (e.g., crystalline or amorphous solids) that can be reconstituted to provide liquid dosage forms suitable for oral or parenteral administration to a patient. The unit dosage form does not necessarily have to be administered as a single dose nor does a single unit dosage form necessarily constitute an entire dose.

Further abbreviations and acronyms are given in the table below.

| | |
|---|---|
| ACTH | adrenocorticotropic hormone |
| AE | adverse event |
| ALT | alanine aminotransferase (also known as serum glutamic-pyruvic transaminase (SGPT)) |
| ANOVA | analysis of variance |
| AST | aspartate aminotransferase (also known as serum glutamic oxaloacetic transaminase (SGOT)) |
| BUN | blood urea nitrogen |
| C. | Celsius |
| CBC | complete blood count |
| CHF | congestive heart failure |
| CKD | chronic kidney disease |
| CKD-EPI | Chronic Kidney Disease Epidemiology Collaboration |

-continued

| | |
|---|---|
| CMH | Cochran-Mantel-Haenszel |
| CPK | creatine phosphokinase |
| CRF | case report form |
| CRO | contract research organization |
| CS | clinically significant |
| CV | cardiovascular |
| CVD | cardiovascular disease |
| dL | deciliter |
| DVT | deep venous thrombosis |
| EAC | Endpoint Adjudication Committee |
| ECG | electrocardiogram |
| EDC | electronic data capture |
| eGFR | estimated glomerular filtration rate |
| EOT | end of treatment |
| EPO | erythropoietin |
| ESA | erythropoiesis-stimulating agent |
| ESRD | end-stage renal disease |
| EU | European Union |
| F. | Fahrenheit |
| FDA | Food and Drug Administration |
| g | gram |
| GCP | Good Clinical Practice |
| GFR | glomerular filtration rate |
| GMP | Good Manufacturing Practice |
| HA | health authority |
| HDL | high-density lipoprotein |
| Hb | hemoglobin |
| Hgb | hemoglobin |
| HIF | hypoxia-inducible factor |
| HIFPH | hypoxia-inducible factor prolyl-hydroxylase |
| HIF-PHI | hypoxia-inducible factor prolyl-hydroxylase inhibitor |
| $IC_{50}$ | 50% inhibitory concentration |
| ICH | International Conference on Harmonization |
| IDMC | Independent Data Monitoring Committee |
| IDMS | isotope dilution mass spectrometry |
| IEC | independent ethics committee |
| INR | international normalized ratio |
| IRB | institutional review board |
| IV | intravenous(ly) |
| IWR | interactive web response |
| JSDT | Japanese Society for Dialysis Therapy |
| JSN | Japanese Society of Nephrology |
| KDIGO | Kidney Disease: Improving Global Outcomes |
| kg | kilogram |
| LDH | lactate dehydrogenase |
| LDL | low-density lipoprotein |
| LLN | lower limit of normal |
| MACE | major adverse cardiovascular events |
| MCH | mean corpuscular (cell) hemoglobin |
| MCHC | mean corpuscular (cell) hemoglobin concentration |
| MCV | mean corpuscular (cell) volume |
| MedDRA | Medical Dictionary for Regulatory Activities |
| μM | micromolar |
| mg | milligram |
| mL | milliliter |
| mRNA | messenger ribonucleic acid |
| MTD | maximum tolerated dose |
| NDD-CKD | non-dialysis dependent chronic kidney disease |
| ng | nanogram |
| PD | pharmacodynamics(s) |
| PE | pulmonary embolism |
| PHD | prolyl 4-hydroxylase domain |
| PK | pharmacokinetic(s) |
| PP | per protocol |
| PT | prothrombin time |
| PTT | partial thromboplastin time |
| QA | quality assurance |
| QC | quality control |
| RBC | red blood cell |
| RDW | red cell distribution width |
| ROW | rest of world |
| SAE | serious adverse event |
| SAP | Statistical Analysis Plan |
| SC | subcutaneous(ly) |
| SGOT | serum glutamic oxaloacetic transaminase (also known as aspartate aminotransferase (AST)) |
| SGPT | serum glutamic pyruvic transaminase (also known as alanine aminotransferase (ALT)) |
| SmPC | summary of product characteristics |
| SV | Screening visit |
| TIBC | total iron binding capacity |
| TREAT | Trial to Reduce Cardiovascular Events with Aranesp Therapy |
| TSAT | transferrin saturation |
| uACR | urine albumin-to-creatinine ratio |
| ULN | upper limit of normal |
| US | United States |
| VEGF | vascular endothelial growth factor |
| WBC | white blood cell |
| WHO | World Health Organization |

Methods of the Invention

Methods described herein can modulate a drug-drug interaction between one drug (e.g., a first drug) and another drug (e.g., a second drug) in a subject having renal anemia (anemia secondary to or associated with chronic kidney disease), where one drug (e.g., a first drug) is a HIF-PH inhibitor (e.g., {[5-(3-chlorophenyl)-3-hydroxypyridine-2-carbonyl]amino}acetic acid (Compound 1)), and the other drug (e.g., a second drug) includes but is not limited to a drug comprising a polymeric amine that binds phosphate (e.g., a sevelamer hydrochloride or sevelamer carbonate); and an inhibitor and/or a substrate of certain proteins, receptors, and/or transporters (e.g., probenecid, cyclosporine, rifampin, digoxin, or adefovir).

Therapeutic methods for patients having anemia (e.g., anemia associated with or secondary to chronic kidney disease) comprising administration of a HIF-PH inhibitor (e.g., vadadustat) can also comprise the administration of one or more additional therapeutic agents. Such additional therapeutic agents can be useful for treating one or more co-morbid conditions, such as those pre-existing at the time of commencement of the anemia therapy and/or arising during the period of anemia treatment.

For example, co-morbid conditions and/or complications can include (but are not limited to) hyperphosphatemia, which is resulted from impaired phosphorus excretion due to increasingly dysregulated calcium-phosphorus homeostasis. Co-morbid conditions can also include, but are not limited to, thrombosis, sleep disorders, somnolence, retinal hemorrhage, rotational vertigo, high blood pressure, palpitations, diarrhea, nausea, abdominal discomfort, vomiting, soft stool, gastroenteritis, stomatitis, liver dysfunction, AST elevation, rash, pruritus, eczema, erythema, alopecia, cold sweats, frequent urination, serum ferritin reduction, trans ferritin saturation reduction, fatigue, chest pain, bilirubin rise, and/or ALT rise. Other co-morbid conditions include, but are not limited to gout, gouty arthritis, hyperuricemia, high cholesterol, triglyceride levels, hypervolemia, edema, and/or other swelling related to, e.g., congestive heart failure, liver disease, kidney disease.

In embodiments, administration of one or more additional therapeutic agents can be useful for treating or preventing gout, gouty arthritis, the prophylaxis of organ rejection in kidney, liver, and heart allogeneic transplants, rheumatoid arthritis, psoriasis, tuberculosis, meningococcal carriers, heart failure (e.g., for increasing myocardial contractility, and/or control of resting ventricular rate), atrial fibrillation, and/or chronic hepatitis B.

However, significant challenges can arise when a patient receives multiple therapeutic agents, and the therapeutic agents can interact with each other in the patient's body in a way that can adversely impact the intended therapeutic effect. As described herein, such drug-drug interactions can manifest in ways that impact pharmaceutical interactions, pharmacokinetic interactions, pharmacodynamic interactions, absorption, distribution, metabolism, and/or excretion. For example, a drug-drug interaction may adversely impact bioavailability and/or absorption of Compound 1 and/or another drug (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)). In particular, a drug-drug interaction may adversely impact bioavailability and/or absorption of Compound 1 and/or a drug comprising a polymeric amine that binds phosphate (e.g., a sevelamer hydrochloride or sevelamer carbonate).

In embodiments, a method described herein prevents a drug-drug interaction between a drug that is a HIF-PH inhibitor (e.g., {[5-(3-chlorophenyl)-3-hydroxypyridine-2-carbonyl]amino}acetic acid (Compound 1) and another drug (e.g., a drug comprising a polymeric amine that binds phosphate (e.g., sevelamer hydrochloride or sevelamer carbonate); or inhibitors and/or substrates of certain proteins, receptors, or transporters (e.g., probenecid, cyclosporine, rifampin, digoxin, or adefovir)). In embodiments, a method described herein prevents a drug-drug interaction between a first drug that is a HIF-PH inhibitor (e.g., {[5-(3-chlorophenyl)-3-hydroxypyridine-2-carbonyl]amino}acetic acid (Compound 1) and a second drug (e.g., a drug comprising a polymeric amine that binds phosphate (e.g., sevelamer hydrochloride or sevelamer carbonate); or inhibitors and/or substrates of certain proteins, receptors, or transporters (e.g., probenecid, cyclosporine, rifampin, digoxin, or adefovir)). In embodiments, a method described herein controls a drug-drug interaction. In embodiments, a method described herein reduces a drug-drug interaction. In embodiments, a method described herein minimizes a drug-drug interaction.

In embodiments, a method described herein prevents a drug-drug interaction between a drug that is a HIF-PH inhibitor (e.g., {[5-(3-chlorophenyl)-3-hydroxypyridine-2-carbonyl]amino}acetic acid (Compound 1) and a drug comprising a polymeric amine that binds phosphate (e.g., a sevelamer hydrochloride or sevelamer carbonate). In embodiments, a method described herein prevents a drug-drug interaction between a first drug that is a HIF-PH inhibitor (e.g., {[5-(3-chlorophenyl)-3-hydroxypyridine-2-carbonyl]amino}acetic acid (Compound 1) and a second drug comprising a polymeric amine that binds phosphate (e.g., a sevelamer hydrochloride or sevelamer carbonate). In embodiments, a method described herein controls a drug-drug interaction. In embodiments, a method described herein reduces a drug-drug interaction. In embodiments, a method described herein minimizes a drug-drug interaction.

In embodiments, a drug-drug interaction relates to pharmaceutical interactions, pharmacokinetic interactions, pharmacodynamic interactions, absorption, distribution, metabolism, and/or excretion. In embodiments, a method described herein increases bioavailability of a drug. In embodiments, a method described herein maintains bioavailability of a drug. In embodiments, a method described herein reduces (e.g., minimizes) a decrease in absorption of a drug. In embodiments, a method described herein prevents a decrease in absorption of a drug. In embodiments, a method described herein controls a decrease in absorption of a drug.

Dose Adjustments

In embodiments, a drug-drug interaction (e.g., as described herein) is modulated by adjustment of the dosage amount of the therapeutic agent administered to a patient (e.g., adjusted compared to the amount when administered in monotherapy). In embodiments, a drug-drug interaction (e.g., as described herein) is modulated by adjustment of the dosage amount of at least one therapeutic agent administered to a patient.

In embodiments, a dose adjustment occurs independently of a timing adjustment.

In embodiments, both a dose adjustment and a timing adjustment are made.

In embodiments, only a dose adjustment or only a timing adjustment is made. In embodiments, only a dose adjustment is made.

In embodiments, a drug-drug interaction (e.g., as described herein) is modulated by adjustment of the dosage amount of at least one therapeutic agent administered to a patient. In embodiments, the dosage amount of a drug (e.g., a first drug) that is a HIF-PH inhibitor (e.g., {[5-(3-chlorophenyl)-3-hydroxypyridine-2-carbonyl]amino}acetic acid (Compound 1), or a pharmaceutically acceptable salt thereof, or a pharmaceutical composition thereof) is adjusted. In embodiments, the dosage amount is increased. In embodiments, the dosage amount is decreased. In embodiments, the dosage amount of another drug (e.g., a second drug comprising a polymeric amine that binds phosphate (e.g., sevelamer hydrochloride or sevelamer carbonate), probenecid, cyclosporine, rifampin, digoxin, adefovir, or another as described herein) is adjusted. In embodiments, the dosage amount is increased. In embodiments, the dosage amount is decreased. In embodiments, the dosage amounts of both drugs (e.g., a drug that is a HIF-PH inhibitor such as {[5-(3-chlorophenyl)-3-hydroxypyridine-2-carbonyl]amino}acetic acid (Compound 1), or a pharmaceutically acceptable salt thereof; and a drug comprising a polymeric amine that binds phosphate, probenecid, cyclosporine, rifampin, digoxin, adefovir, or another as described herein) are adjusted. In embodiments, the dosage amount is increased. In embodiments, the dosage amount is decreased.

In embodiments, the dosage amount is increased. In embodiments, the dosage amount is increased by no more than about 100%, 200%, or 300%. In embodiments, the dosage amount is increased by more than about 300%. In embodiments, the dosage amount is increased by about 20%, 40%, 60%, 80%, 100%, 120%, 140%, 160%, 180%, 200%, 220%, 240%, 260%, 280%, or 300%. In embodiments, the dosage amount is increased by 0 to about 50%, about 50% to about 100%, about 100% to about 150%, about 150% to about 200%, about 200% to about 250%, or about 250% to about 300%. In embodiments, the dosage amount is decreased. In embodiments, the dosage amount is decreased by at least about 10%, 20%, 30%, 40%, 50%, 60%, 70%, 80%, or 90%, or 100%. In embodiments, the dosage amount is decreased by at least 0 to about 25%, at least about 25% to about 50%, at least about 50% to about 75%, or at least about 75% to about 100%. In embodiments, the dosage amount is decreased by about 10%, 20%, 30%, 40%, 50%, 60%, 70%, 80%, or 90%, or 100%. In embodiments, the dosage amount is decreased by 0 to about 25%, about 25% to about 50%, about 50% to about 75%, or about 75% to about 100%. In embodiments, the dosage amount is decreased by no more than about 25%, 50%, 75%, or 100%.

In embodiments, the dosage amount of at least one therapeutic agent is adjusted, wherein the adjustments is as described herein. In embodiments, the dosage amount is increased and the amount is as described herein. In embodiments, the dosage amount is decreased and the amount is as described herein.

In embodiments, the dosage amount of a drug (e.g., a first drug) that is a HIF-PH inhibitor (e.g., {[5-(3-chlorophenyl)-3-hydroxypyridine-2-carbonyl]amino}acetic acid (Compound 1), or a pharmaceutically acceptable salt thereof, or a pharmaceutical composition thereof) is adjusted, wherein the adjustments is as described herein. In embodiments, the dosage amount is increased and the amount is as described herein. In embodiments, the dosage amount is decreased and the amount is as described herein.

In embodiments, the dosage amount of another (e.g., a second) drug (e.g., a therapeutic agent such as a drug comprising a polymeric amine that binds phosphate (e.g., sevelamer hydrochloride or sevelamer carbonate), probenecid, cyclosporine, rifampin, digoxin, adefovir, or another as described herein) is adjusted, wherein the adjustments is as described herein. In embodiments, the dosage amount is increased and the amount is as described herein. In embodiments, the dosage amount is decreased and the amount is as described herein.

In embodiments, the dosage amounts of both a drug (e.g., a first drug that is a HIF-PH inhibitor such as {[5-(3-chlorophenyl)-3-hydroxypyridine-2-carbonyl]amino}acetic acid (Compound 1), or a pharmaceutically acceptable salt thereof) and another (e.g., a second) drug (e.g., a drug comprising a polymeric amine that binds phosphate (e.g., sevelamer hydrochloride or sevelamer carbonate), probenecid, cyclosporine, rifampin, digoxin, adefovir, or another as described herein) are both adjusted, wherein the adjustments is as described herein. In embodiments, the dosage amount is increased and the amount is as described herein. In embodiments, the dosage amount is decreased and the amount is as described herein.

In embodiments, a drug that is a HIF-PH inhibitor (e.g., {[5-(3-chlorophenyl)-3-hydroxypyridine-2-carbonyl]amino}acetic acid (Compound 1), or a pharmaceutically acceptable salt thereof) is the first drug administered to the patient. In embodiments, a drug that is a HIF-PH inhibitor (e.g., {[5-(3-chlorophenyl)-3-hydroxypyridine-2-carbonyl]amino}acetic acid (Compound 1), or a pharmaceutically acceptable salt thereof) is not the first drug administered to the patient. In embodiments, a drug that is a HIF-PH inhibitor (e.g., {[5-(3-chlorophenyl)-3-hydroxypyridine-2-carbonyl]amino}acetic acid (Compound 1), or a pharmaceutically acceptable salt thereof) is the second drug administered to the patient.

Provided herein is a method of reducing or minimizing drug-drug interaction between a drug (e.g., a first drug) and another (e.g., a second) drug (or a metabolite thereof) in a subject. In embodiments, the amount of the other (e.g., the second) drug (e.g., a drug comprising a polymeric amine that binds phosphate (e.g., sevelamer hydrochloride or sevelamer carbonate), probenecid, cyclosporine, rifampin, digoxin, adefovir, or another as described herein) is adjusted compared to the amount when administered in the absence of the first drug or in monotherapy. Also provided herein is method of preventing and controlling drug-drug interaction between a drug (e.g., a first drug) and another (e.g., a second) drug (or a metabolite thereof) in a subject, wherein the amount of the other (e.g., the second) drug (e.g., a drug comprising a polymeric amine that binds phosphate (e.g., sevelamer hydrochloride or sevelamer carbonate), probenecid, cyclosporine, rifampin, digoxin, adefovir, or another as described herein) is adjusted compared to the amount when administered in the absence of the first drug or in monotherapy. In embodiments, the subject is administered an effective amount of a drug (e.g., a first drug that is {[5-(3-chlorophenyl)-3-hydroxypyridine-2-carbonyl]amino}acetic acid (Compound 1), or a pharmaceutically acceptable salt thereof); and an effective amount of another (e.g., a second) drug (e.g., a drug comprising a polymeric amine that binds phosphate (e.g., sevelamer hydrochloride or sevelamer carbonate), probenecid, cyclosporine, rifampin, digoxin, adefovir, or another as described herein).

Also provided herein are methods of maintaining bioavailability of one or more therapeutic agents (including a metabolite thereof) administered to a patient. For example, when a patient receives two different therapeutic agents, methods described herein can maintain the bioavailability of one or both therapeutic agents (including a metabolite thereof). Accordingly, in embodiments, provided herein are methods for maintaining the bioavailability of a drug (or a metabolite thereof), comprising administering to a subject an effective amount of a drug (e.g., a first drug that is {[5-(3-chlorophenyl)-3-hydroxypyridine-2-carbonyl]amino}acetic acid (Compound 1), or a pharmaceutically acceptable salt thereof); and an effective amount of another (e.g., a second) drug (e.g., a drug comprising a polymeric amine that binds phosphate (e.g., sevelamer hydrochloride or sevelamer carbonate), probenecid, cyclosporine, rifampin, digoxin, adefovir, or another as described herein). In embodiments, bioavailability of one drug (e.g., the first drug, or a metabolite thereof) is maintained. In embodiments, bioavailability of another (e.g., the second) drug (or a metabolite thereof) is maintained. In embodiments, bioavailability of both drugs (or a metabolite thereof) are maintained.

Also provided herein are methods of minimizing, preventing and controlling an increase in exposure to one or more therapeutic agents (including a metabolite thereof) administered to a patient. For example, when a patient receives two different therapeutic agents, methods described herein can minimize, prevent and/or control an increase in exposure to one or both therapeutic agents (including a metabolite thereof). Accordingly, in embodiments, provided herein are methods of minimizing, preventing and controlling an increase in exposure to a drug (or a metabolite thereof), comprising administering to a subject an effective amount of a drug (e.g., a first drug that is {[5-(3-chlorophenyl)-3-hydroxypyridine-2-carbonyl]amino}acetic acid (Compound 1), or a pharmaceutically acceptable salt thereof); and an effective amount of another (e.g., a second) drug (e.g., a drug comprising a polymeric amine that binds phosphate (e.g., sevelamer hydrochloride or sevelamer carbonate), probenecid, cyclosporine, rifampin, digoxin, adefovir, or another as described herein). In embodiments, an increase in exposure to one drug (e.g., the first drug, or a metabolite thereof) is controlled (e.g., there is no change in exposure or the change of exposure is less than about 25%, about 20%, about 15%, about 10%, or about 5%). In embodiments, an increase in exposure to the other (e.g., the second) drug (or a metabolite thereof) is controlled (e.g., there is no change in exposure or the change of exposure is less than about 25%, about 20%, about 15%, about 10%, or about 5%). In embodiments, an increase in exposure to both drugs (or a metabolite thereof) is controlled (e.g., there is no change in exposure or the change of exposure is less than about 25%, about 20%, about 15%, about 10%, or about 5%).

Also provided herein are methods of minimizing, preventing and/or controlling a decrease in the absorption of one or more therapeutic agents (including a metabolite thereof) administered to a patient. For example, when a patient receives two different therapeutic agents, methods described herein can control a decrease in the absorption of one or both therapeutic agents. Accordingly, in embodiments, provided herein are methods of controlling a decrease in the absorption of a drug, comprising administering to a subject an effective amount of a drug (e.g., a first drug) comprising an effective amount of {[5-(3-chlorophenyl)-3-hydroxypyridine-2-carbonyl]amino}acetic acid (Compound 1), or a pharmaceutically acceptable salt thereof; and an effective amount of another (e.g., a second) drug (e.g., a therapeutic agent such as a drug comprising a polymeric amine that binds phosphate (e.g., sevelamer hydrochloride or sevelamer carbonate), probenecid, cyclosporine, rifampin, digoxin, adefovir, or another as described herein). In embodiments, a decrease in the absorption of one drug (e.g., the first drug, or a metabolite thereof) is controlled (e.g., there is no change in absorption or the change of absorption is less than about 25%, about 20%, about 15%, about 10%, or about 5%). In embodiments, a decrease in the absorption of the other (e.g., the second) drug (or a metabolite thereof) is controlled (e.g., there is no change in absorption or the change of absorption is less than about 25%, about 20%, about 15%, about 10%, or about 5%). In embodiments, a decrease in the absorption of both drugs (or a metabolite thereof) is controlled (e.g., there is no change in absorption or the change of absorption is less than about 25%, about 20%, about 15%, about 10%, or about 5%).

Timing Adjustments

In embodiments, a drug-drug interaction (e.g., as described herein) is modulated by adjustment of the timing of administration of each therapeutic agent administered to a patient.

In embodiments, administration of a drug (e.g., a first drug) and the other (e.g., a second) drug occurs concomitantly (concomitant administration). In embodiments, concomitant administration of a drug (e.g., a first drug) and administration of the other (e.g., a second) drug occur within a time period that is no more than one about hour (e.g., no more than about 1, 5, 10, 15, 20, 25 or 30 minutes). In embodiments, concomitant administration of a drug (e.g., a first drug) and the other (e.g., a second) drug occurs simultaneously (simultaneous administration) where both compounds are administered at the same time.

In embodiments, administration of a drug (e.g., a first drug) that is a HIF-PH inhibitor (e.g., {[5-(3-chlorophenyl)-3-hydroxypyridine-2-carbonyl]amino}acetic acid (Compound 1), or a pharmaceutically acceptable salt thereof) and another (e.g., a second) drug (e.g., a therapeutic agent such as a drug comprising a polymeric amine that binds phosphate (e.g., sevelamer hydrochloride or sevelamer carbonate), probenecid, cyclosporine, rifampin, digoxin, adefovir, or another as described herein) occurs sequentially (sequential administration). In embodiments, administration of a drug (e.g., a first drug) that is a HIF-PH inhibitor (e.g., {[5-(3-chlorophenyl)-3-hydroxypyridine-2-carbonyl]amino}acetic acid (Compound 1), or a pharmaceutically acceptable salt thereof) and another drug (e.g., a second drug) that is a drug comprising a polymeric amine that binds phosphate (e.g., sevelamer hydrochloride or sevelamer carbonate) occurs sequentially (sequential administration).

In embodiments, a timing adjustment occurs independently of a dose adjustment.

In embodiments, both a dose adjustment and a timing adjustment are made.

In embodiments, only a timing adjustment or only a dose adjustment is made. In embodiments, only a timing adjustment is made.

In embodiments, administration of a drug (e.g., a first drug) and the other (e.g., a second) drug occurs sequentially (sequential administration). In embodiments, administration of two drugs (e.g., a first drug and a second drug) is separated by a time period that is at least about 1 hour to about 6 hours, at least about 2 hours to about 6 hours, at least about 2 hours to about 4 hours, at least about 3 hours to about 6 hours, at least about 4 hours to about 6 hours, at least about 1 hour to about 12 hours, at least about 2 hours to about 12 hours, at least about 3 hours to about 12 hours, at least about 4 hours to about 12 hours, or at least about 6 hours to about 12 hours.

In embodiments, administration of two drugs (e.g., a first drug and a second drug) is separated by a time period that is at least about 1 hour, 2 hours, 3 hours, 4 hours, 5 hours, 6 hours, 7 hours, 8 hours, 9 hours, 10 hours, 11 hours, or 12 hours.

In embodiments, administration of two drugs (e.g., a first drug and a second drug) is separated by a time period that is no more than about 12 hours or about 22 hours.

In embodiments, administration of two drugs (e.g., a first drug and a second drug) is separated by a time period that is no more than about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, or 22 hours.

In embodiments, administration of two drugs (e.g., a first drug and a second drug) is separated by a time period that is about 1 hour to about 6 hours, about 2 hours to about 6 hours, about 2 hours to about 4 hours, about 3 hours to about 6 hours, about 4 hours to about 6 hours, about 1 hour to about 12 hours, about 2 hours to about 12 hours, about 3 hours to about 12 hours, about 4 hours to about 12 hours, or about 6 hours to about 12 hours.

In embodiments, administration of two drugs (e.g., a first drug and a second drug) is separated by a time period that is at least about 1 hour, about 2 hours, about 3 hours, about 4 hours, about 5 hours, about 6 hours, about 7 hours, about 8 hours, about 9 hours, about 10 hours, about 11 hours, or about 12 hours.

In embodiments, administration of two drugs (e.g., a first drug and a second drug) is separated by a time period that is at least about 2 hours. In embodiments, administration of two drugs (e.g., a first drug and a second drug) is separated by a time period that is at least about 1 hour.

In embodiments, a drug (e.g., a first drug) is given at least 1 hour before taking the other drug (e.g., a second drug). In embodiments, a drug (e.g., a first drug) is given at least 2 hours after taking the other drug (e.g., a second drug).

In embodiments, a drug that is a HIF-PH inhibitor (e.g., {[5-(3-chlorophenyl)-3-hydroxypyridine-2-carbonyl]amino}acetic acid (Compound 1), or a pharmaceutically acceptable salt thereof) is the first drug administered to the patient. In embodiments, a drug that is a HIF-PH inhibitor (e.g., {[5-(3-chlorophenyl)-3-hydroxypyridine-2-carbonyl]amino}acetic acid (Compound 1), or a pharmaceutically acceptable salt thereof) is not the first drug administered to the patient. In embodiments, a drug that is a HIF-PH inhibitor (e.g., {[5-(3-chlorophenyl)-3-hydroxypyridine-2-carbonyl]amino}acetic acid (Compound 1), or a pharmaceutically acceptable salt thereof) is the second drug administered to the patient.

Provided herein is a method of reducing or minimizing drug-drug interaction between a drug (e.g., a first drug) and another drug (e.g., a second drug) in a subject. Also provided herein is method of preventing or controlling drug-drug interaction between one drug (e.g., a first drug) and another drug (e.g., a second drug) in a subject. In embodiments, one drug (e.g., a first drug) is given at least about 2 hours before and/or after taking the other drug (e.g., a second drug). In embodiments, one drug (e.g., a first drug) is given at least about 1 hour before and/or after taking the other drug (e.g., a second drug). In some embodiments, the subject is administered an effective amount of one drug (e.g., a first drug) or a pharmaceutical composition comprising an effective amount of the drug, wherein the drug is {[5-(3-chlorophenyl)-3-hydroxypyridine-2-carbonyl]amino}acetic acid (Compound 1); and an effective amount of another drug (e.g., a second drug), wherein the other drug is a drug comprising a polymeric amine that binds phosphate (e.g., sevelamer hydrochloride or sevelamer carbonate), probenecid, cyclosporine, rifampin, digoxin, adefovir, or another as described herein. In embodiments, the other drug (e.g., a second drug) is a composition comprising a polymeric amine that binds phosphate (e.g., sevelamer hydrochloride or sevelamer carbonate).

Also provided herein are methods of increasing the bioavailability of one or more therapeutic agent administered to the patient. For example, when a patient receives two different therapeutic agents, methods described herein can increase the bioavailability of one or both therapeutic agents. Accordingly, in embodiments, provided herein are methods of increasing the bioavailability of a drug, comprising administering to a subject an effective amount of one drug (e.g., a first drug) comprising an effective amount of {[5-(3-chlorophenyl)-3-hydroxypyridine-2-carbonyl]amino}acetic acid (Compound 1), or a pharmaceutically acceptable salt thereof; and an effective amount of another (e.g., a second) drug (e.g., a therapeutic agent such as a drug comprising a polymeric amine that binds phosphate (e.g., sevelamer hydrochloride or sevelamer carbonate), probenecid, cyclosporine, rifampin, digoxin, adefovir, or another as described herein). In embodiments, one drug (e.g., a first drug) is {[5-(3-chlorophenyl)-3-hydroxypyridine-2-carbonyl]amino}acetic acid (Compound 1), or a pharmaceutically acceptable salt thereof. In embodiments, the other drug (e.g., a second drug) is a drug comprising a polymeric amine that binds phosphate (e.g., sevelamer hydrochloride or sevelamer carbonate), probenecid, cyclosporine, rifampin, digoxin, adefovir, or another as described herein. In embodiments, the other drug (e.g., a second drug) is a composition comprising a polymeric amine that binds phosphate (e.g., sevelamer hydrochloride or sevelamer carbonate). In embodiments, one drug (e.g., a first drug) is given at least about 2 hours before and/or after taking the other drug (e.g., a second drug). In embodiments, one drug (e.g., a first drug) is given at least about 1 hour before and/or after taking the other drug (e.g., a second drug). In embodiments, bioavailability of one of the two drugs (e.g., the first drug or the second drug) is increased. In embodiments, bioavailability of both drugs are increased.

Also provided herein are methods of maintaining bioavailability of one or more therapeutic agents administered to a patient. For example, when a patient receives two different therapeutic agents, methods described herein can maintain the bioavailability of one or both therapeutic agents. Accordingly, in embodiments, provided herein are methods for maintaining the bioavailability of a drug, comprising administering to a subject an effective amount of a drug (e.g., a first drug) comprising an effective amount of {[5-(3-chlorophenyl)-3-hydroxypyridine-2-carbonyl]amino}acetic acid (Compound 1), or a pharmaceutically acceptable salt thereof; and an effective amount of another (e.g., a second) drug (e.g., a therapeutic agent such as a drug comprising a polymeric amine that binds phosphate (e.g., sevelamer hydrochloride or sevelamer carbonate), probenecid, cyclosporine, rifampin, digoxin, adefovir, or another as described herein). In embodiments, one drug (e.g., a first drug) is {[5-(3-chlorophenyl)-3-hydroxypyridine-2-carbonyl]amino}acetic acid (Compound 1), or a pharmaceutically acceptable salt thereof. In embodiments, the other drug (e.g., a second drug) is a drug comprising a polymeric amine that binds phosphate (e.g., sevelamer hydrochloride or sevelamer carbonate), probenecid, cyclosporine, rifampin, digoxin, adefovir, or another as described herein. In embodiments, the other drug (e.g., a second drug) is a composition comprising a polymeric amine that binds phosphate (e.g., sevelamer hydrochloride or sevelamer carbonate). In embodiments, one drug (e.g., a first drug) is given at least about 2 hours before and/or after taking the other drug (e.g., a second drug). In embodiments, one drug (e.g., a first drug) is given at least about 1 hour before and/or after taking the other drug (e.g., a second drug). In embodiments, bioavailability of one of the two drugs (e.g., the first drug or the second drug) is maintained. In embodiments, bioavailability of both drugs are maintained.

Also provided herein are methods of minimizing, preventing and/or controlling a decrease in the absorption of one or more therapeutic agents administered to a patient. For example, when a patient receives two different therapeutic agents, methods described herein can control a decrease in the absorption of one or both therapeutic agents. Accordingly, in embodiments, provided herein are methods of controlling a decrease in the absorption of a drug, comprising administering to a subject an effective amount of a drug (e.g., a first drug) comprising an effective amount of {[5-(3-chlorophenyl)-3-hydroxypyridine-2-carbonyl]amino}acetic acid (Compound 1), or a pharmaceutically acceptable salt thereof; and an effective amount of another (e.g., a second) drug (e.g., a therapeutic agent such as a drug comprising a polymeric amine that binds phosphate (e.g., sevelamer hydrochloride or sevelamer carbonate), probenecid, cyclosporine, rifampin, digoxin, adefovir, or another as described herein). In embodiments, one drug (e.g., a first drug) is {[5-(3-chlorophenyl)-3-hydroxypyridine-2-carbonyl]amino}acetic acid (Compound 1), or a pharmaceutically acceptable salt thereof. In embodiments, the other drug (e.g., a second drug) is a drug comprising a polymeric amine that binds phosphate (e.g., sevelamer hydrochloride or sevelamer carbonate), probenecid, cyclosporine, rifampin, digoxin, adefovir, or another as described herein. In embodiments, the other drug (e.g., a second drug) is a composition comprising a polymeric amine that binds phosphate (e.g., sevelamer hydrochloride or sevelamer carbonate). In embodiments, one drug (e.g., a first drug) is given at least about 2 hours before and/or after taking the other drug (e.g., a second drug). In embodiments, one drug (e.g., a first drug) is given at least about 1 hour before and/or after taking the other drug (e.g., a second drug). In embodiments, a decrease of absorption of one of the two drugs (e.g., the first drug or the second drug) is minimized, prevented and/or controlled (e.g., there is no change in absorption or the change of absorption is less than about 25%, about 20%, about 15%, about 10%, or about 5%). In embodiments, decreases of absorption of both drugs are minimized, prevented and/or controlled (e.g., for each drug, there is independently no change in absorption or the change of absorption is less than about 25%, about 20%, about 15%, about 10%, or about 5%).

In some embodiments of the methods provided herein, administration of the other (e.g., a second) drug is associated with a medical treatment. For example, the drug comprising a polymeric amine (e.g., sevelamer hydrochloride or sevelamer carbonate) may be administered to reduce phosphorus intake and lower serum phosphate levels toward the normal range; administration of probenecid can be helpful for treating or preventing gout or gouty arthritis; administration of cyclosporine can be helpful for treating or preventing the prophylaxis of organ rejection in kidney, liver, and heart allogeneic transplants, as well as treating or preventing rheumatoid arthritis and/or psoriasis; administration of rifampin can be helpful for treating or preventing tuberculosis and/or meningococcal carriers; administration of digoxin can be helpful for treating or preventing heart failure (e.g., for increasing myocardial contractility, and/or control of resting ventricular rate) and/or atrial fibrillation; administration of adefovir can be helpful for treating or preventing chronic hepatitis B. In embodiments, administration of the polymeric amine-containing composition is associated with management of hyperphosphatemia.

In some embodiments of the methods provided herein, Compound 1, or a pharmaceutical composition thereof, is administered at least about 2 hours before and/or after the drug comprising a polymeric amine that binds phosphate (e.g., sevelamer hydrochloride or sevelamer carbonate). In embodiments, Compound 1, or a pharmaceutical composition thereof, is administered at least about 1 hour before and/or after the drug comprising a polymeric amine that binds phosphate (e.g., sevelamer hydrochloride or sevelamer carbonate). In embodiments, Compound 1, or a pharmaceutical composition thereof, is administered at least about 1 hour before the drug comprising a polymeric amine that binds phosphate (e.g., sevelamer hydrochloride or sevelamer carbonate). In embodiments, Compound 1, or a pharmaceutical composition thereof, is administered at least about 2 hours after the drug comprising a polymeric amine that binds phosphate (e.g., sevelamer hydrochloride or sevelamer carbonate).

In certain embodiments, Compound 1, or a pharmaceutical composition thereof, is administered about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours before the polymeric amine-containing composition. In other embodiments, Compound 1, or a pharmaceutical composition thereof, is administered about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours after the polymeric amine-containing composition.

Methods described herein can be useful in subjects having anemia. Anemia may be characterized by hemoglobin threshold as follows:

| Age or Gender Group | Hemoglobin Threshold (g/dL) |
|---|---|
| Children (0.50-4.99 yrs.) | 11.0 |
| Children (5.00-11.99 yrs.) | 11.5 |
| Children (12.00-14.99 yrs.) | 12.0 |
| Non-pregnant Women (≥15.00 yrs) | 12.0 |
| Pregnant Women | 11.0 |
| Men (≥15.00 yrs) | 13.0 |

In embodiments, a subject has renal anemia (anemia secondary to or associated with chronic kidney disease).

Dialysis Status

The methods described herein can be beneficial to patients of different dialysis status, including the statuses described herein.

In embodiments, the patient is non-dialysis dependent. For example, in some embodiments, the patient with chronic kidney disease is non-dialysis dependent (an NDD-CKD patient).

In embodiments, the patient is dialysis-dependent. For example, in embodiments, the patient with chronic kidney disease is dialysis-dependent (a DD-CKD patient).

In embodiments, the patient receives or previously has received dialysis. In embodiments, the patient receives dialysis. In embodiments, the patient previously received dialysis.

In embodiments, dialysis is hemodialysis (HD). In embodiments, the patient with chronic kidney disease receives or previously received hemodialysis. In embodiments, the patient with chronic kidney disease receives hemodialysis. In embodiments, the patient with chronic kidney disease previously received hemodialysis.

In embodiments, dialysis is peritoneal dialysis (PD). In embodiments, the patient with chronic kidney disease receives or previously received peritoneal dialysis. In embodiments, the patient with chronic kidney disease receives peritoneal dialysis.

In embodiments, the patient with chronic kidney disease previously received peritoneal dialysis.

Formulations (Pharmaceutical Compositions) of Compound 1

In certain embodiments, Compound 1 may be provided as a formulation (pharmaceutical composition). In embodiments, Compound 1 is provided as a pharmaceutical formulation that is suitable for oral administration. Such pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Exemplary formulations of Compound 1 are described in WO 2014/200773 and WO/2016/161094, which are incorporated by reference in their entirety. Still further exemplary formulations are described herein.

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In embodiments, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HD90, PROSOLV 90 LM, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

In embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof.

In embodiments, fillers may include, but are not limited to isomalt, lactose, lactitol, mannitol, sorbitol xylitol, erythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 weight percent to about 15 weight percent of disintegrant, or from about 1 weight percent to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate, potato or tapioca starch, other starches, pre-gelatinized starch, other starches, clays, other algins, other celluloses, gums, and mixtures thereof.

Glidants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional glidants include, for example, a syloid silica gel (AEROSIL200, manufactured by W.R. Grace Co. of Baltimore, MD), a coagulated aerosol of synthetic silica (marketed by Degussa Co. of Plano, TX), CAB-O-SIL (a pyrogenic colloidal silicon dioxide product sold by Cabot Co. of Boston, MA), and mixtures thereof. If used at all, glidants may be used in an amount of less than about 1 weight percent of the pharmaceutical compositions or dosage forms into which they are incorporated.

Also provided are anhydrous pharmaceutical compositions and dosage forms since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers", include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

In embodiments, provided herein is a tablet formulation comprising 150 mg of Compound 1. In other embodiments, provided herein is a tablet formulation comprising 300 mg of Compound 1. Exemplary 150 mg tablet and the 300 mg tablet formulations are described in Table 1.

TABLE 1

| Exemplary Formulations | | |
|---|---|---|
| | 150 mg Tablet | 300 mg Tablet |
| Active Ingredient | {[5-(3-chlorophenyl)-3-hydroxypyridine-2-carbonyl]amino}acetic acid, 150 mg | {[5-(3-chlorophenyl)-3-hydroxypyridine-2-carbonyl]amino}acetic acid, 300 mg |
| Additives | crystalline cellulose, sodium starch glycolate, hypromellose, light anhydrous silicic acid, polyvinyl alcohol (partial saponification), macrogol 4000, talc, titanium oxide | crystalline cellulose, sodium starch glycolate, hypromellose, light anhydrous silicic acid, polyvinyl alcohol (partially saponified), macrogol 4000, talc, titanium oxide, yellow ferric oxide |

Table 2 further describes exemplary properties of each of the 150 mg tablet of Compound 1 and the 300 mg tablet of Compound 1.

TABLE 2

| Properties of the 150 mg and 300 mg Tablet of Compound 1 | | |
|---|---|---|
| | 150 mg Tablet | 300 mg Tablet |
| Properties, dosage form | White film-coated tablet | Yellow, oval film-coated tablet |
| Size (mm) | 8 | 8 (width)<br>13 (length) |
| Thickness (mm) | 4 | 6 |
| Weight (mg) | 239.2 | 474.6 |

In embodiments of any method described herein, a patient receives one or more tablets of Compound 1 that is substantially according to Table 1 and/or Table 2. In embodiments, a patient receives one or more tablets of Compound 1 that is substantially according to Table 1 and/or Table 2 comprising about 150 mg Compound 1. In embodiments, a patient receives one or more tablets of Compound 1 that is substantially according to Table 1 and/or Table 2 comprising about 300 mg Compound 1. In embodiments, a patient receives a daily dose of about 150-600 mg Compound 1 (e.g., about 150, 300, 450, or 600 mg Compound 1).

Liquid Dosage Forms

Liquid dosage forms for oral administration are also provided herein. Liquid dosage forms for oral administration can include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Amounts of Compound 1 in Unit Dosage Forms

In certain other embodiments, provided herein are unit dosage forms of Compound 1 that comprise about 150 mg and about 600 mg of a compound having a structure of Compound 1, or a pharmaceutically acceptable salt, solvate, or hydrate thereof. Such unit dosage forms can be used to provide a daily dose of Compound 1 that is about 150 mg to about 600 mg.

In certain other embodiments, provided herein are unit dosage forms of Compound 1 that comprise about 150 mg, about 200 mg, about 250 mg, about 300 mg, about 350 mg, about 400 mg, about 450 mg, about 500 mg, about 550 mg, or even about 600 mg of a compound having a structure Compound 1. In certain embodiments, the unit dosage form comprises about 150 mg, about 185 mg, about 200 mg, about 250 mg, about 300 mg, or even about 315 mg of a compound having a structure of Compound 1, or a pharmaceutically acceptable salt, solvate, or hydrate thereof. In certain such embodiments, the unit dosage form is a capsule comprising about 185 mg, about 200 mg, about 200, about 250 mg, or even about 300 mg of the compound.

In embodiments, a unit dosage form comprises about 150 mg of Compound 1. In embodiments, a unit dosage form is a tablet. In embodiments, a unit dosage form is a capsule. In embodiments, a unit dosage form comprising about 150 mg of Compound 1 is substantially the same as that exemplified in Table 1.

In embodiments, a unit dosage form comprises about 300 mg of Compound 1. In embodiments, a unit dosage form is a tablet. In embodiments, a unit dosage form is a capsule. In embodiments, a unit dosage form comprising about 300 mg of Compound 1 is substantially the same as that exemplified in Table 1.

Second Drug

In embodiments, a subject with renal anemia (anemia or secondary to chronic kidney disease) may also be administered another (e.g., a second) therapeutic agent (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)) in addition to Compound 1.

It is understood that "the other", "another", "a second" drug or therapeutic agent as used in methods described herein also encompasses metabolites formed in vivo from an administered drug. For example, methods described herein for the modulation of a drug-drug interaction between Compound 1 and another (e.g., a second) drug can encompass modulation of a drug-drug interaction between Compound 1 and the as-administered another (e.g., a second) drug and/or Compound 1 and one or more metabolites formed in vivo from the as-administered another (e.g., a second) drug.

In embodiments, the other (e.g., a second) therapeutic agent (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)) is administered concomitantly (e.g., simultaneously) with Compound 1. In embodiments, the other (e.g., a second) therapeutic agent (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)) is not administered concomitantly (e.g., simultaneously) with Compound 1. In embodiments, the other (e.g., a second) therapeutic agent (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)) is administered prior to commencement of therapy with Compound 1. In embodiments, the other (e.g., a second) therapeutic agent (e.g., a drug comprising a polymeric amine that binds phosphate (e.g., sevelamer hydrochloride or sevelamer carbonate); or inhibitors and/or substrates of certain proteins, receptors, and/or transporters (e.g., probenecid, cyclosporine, rifampin, digoxin, or adefovir)) is administered after commencing therapy with Compound 1.

In embodiments, a subject is administered another (e.g., a second) drug for treating a disease or condition in the patient that was present at the time treatment with Compound 1 was commenced.

In embodiments, a subject is administered another (e.g., a second) drug for treating or preventing a disease or condition in the patient that was not present at the time treatment with Compound 1 was commenced (e.g., the disease or condition developed after treatment with Compound 1 was commenced). In embodiments, a subject is administered another (e.g., a second) drug for treating or preventing a disease or condition in the patient induced by treatment with Compound 1. In embodiments, a subject is administered another (e.g., a second) drug for treating or preventing a disease or condition in the patient that arises independently of treatment with Compound 1.

In embodiments, a subject receives another (e.g., a second) drug (e.g., a drug comprising a polymeric amine (e.g., sevelamer hydrochloride or sevelamer carbonate)) to reduce phosphorus intake and lower serum phosphate levels toward the normal range. In embodiments, a subject receives another (e.g., a second) drug (e.g., probenecid) for treating or preventing gout or gouty arthritis. In embodiments, a subject receives another (e.g., a second) drug (e.g., cyclosporine) for treating or preventing the prophylaxis of organ rejection in kidney, liver, and heart allogeneic transplants, as well as for treating or preventing rheumatoid arthritis and/or psoriasis. In embodiments, a subject receives another (e.g., a second) drug (e.g., rifampin) for treating or preventing tuberculosis and/or meningococcal carriers. In embodiments, a subject receives another (e.g., a second) drug (e.g., digoxin) for treating or preventing heart failure (e.g., for increasing myocardial contractility, and/or control of resting ventricular rate) and/or atrial fibrillation. In embodiments, a subject receives another (e.g., a second) drug (e.g., adefovir) for treating or preventing chronic hepatitis B.

Drugs Comprising a Polymeric Amine that Binds Phosphate

In methods described herein, a drug comprises a polymeric amine that binds phosphate (e.g., sevelamer hydrochloride or sevelamer carbonate). In embodiments, a second drug is a drug comprising a polymeric amine that binds phosphate (e.g., sevelamer hydrochloride or sevelamer carbonate).

In embodiments, a polymeric amine is a poly(allylamine) crosslinked with epichlorohydrin. This cationic polymer may further comprise a counterion such as chloride or carbonate. In embodiments, a polymeric amine-containing composition is sevelamer carbonate (e.g., Renvela®). In embodiments, a polymeric amine-containing composition is sevelamer hydrochloride (e.g., Renagel®).

In embodiments, a polymeric amine-containing composition is formulated for oral administration. In embodiments, a polymeric amine-containing composition is administered as a tablet. In embodiments, a polymeric amine-containing composition is administered as a powder. In embodiments, a powder is a powder for oral suspension.

In embodiments, a drug comprising a polymeric amine that binds phosphate is a composition comprising sevelamer hydrochloride. In embodiments, a second drug comprising a polymeric amine that binds phosphate is a composition comprising sevelamer hydrochloride. In embodiments, a drug comprising a polymeric amine that binds phosphate is a composition comprising sevelamer carbonate. In embodiments, a second drug comprising a polymeric amine that binds phosphate is a composition comprising sevelamer carbonate.

In embodiments, Compound 1 is administered before (e.g., at least about 1 hour or about 2 hours before) a drug comprising a polymeric amine that binds phosphate (e.g., sevelamer hydrochloride or sevelamer carbonate). In embodiments, Compound 1 is administered after (e.g., at least about 1 hour or about 2 hours after) a drug comprising a polymeric amine that binds phosphate (e.g., sevelamer hydrochloride or sevelamer carbonate).

In embodiments, the patient has renal anemia (anemia associated with or secondary to chronic kidney disease).

In embodiments, a subject with renal anemia (anemia associated with or secondary to chronic kidney disease) may also be administered a composition comprising a polymeric amine that binds phosphate in addition to Compound 1.

In embodiments, methods described herein result in substantially no change to the $AUC_{MAX}$ for Compound 1 (e.g., any change to the $AUC_{MAX}$ of Compound 1 is no more than about 25%, about 20%, or about 15%).

In embodiments, a subject is administered a composition comprising a polymeric amine that binds phosphate for treating a disease or condition in the patient that was present at the time treatment with Compound 1 was commenced.

In embodiments, a subject is administered a composition comprising a polymeric amine that binds phosphate for treating or preventing a disease or condition in the patient that was not present at the time treatment with Compound 1 was commenced (e.g., the disease or condition developed after treatment with Compound 1 was commenced). In embodiments, a subject is administered a composition comprising a polymeric amine that binds phosphate for treating or preventing a disease or condition in the patient induced by treatment with Compound 1. In embodiments, a subject is administered a composition comprising a polymeric amine that binds phosphate for treating or preventing a disease or condition in the patient that arises independently of treatment with Compound 1.

In embodiments, a subject receiving a composition comprising a polymeric amine that binds phosphate receives said composition for treating or preventing high blood phosphate levels (hyperphosphatemia). In embodiments, a subject is on dialysis due to severe kidney disease (e.g., chronic kidney disease).

In embodiments, a subject receiving a composition comprising a polymeric amine that binds phosphate receives said composition for treating or preventing impaired phosphorus excretion.

In embodiments, a subject receiving a composition comprising a polymeric amine that binds phosphate receives said composition for reducing the risk of cardiovascular disease, kidney failure, and mortality in subjects with CKD (chronic kidney disease).

In embodiments, a subject receiving a composition comprising a polymeric amine that binds phosphate receives said composition for reducing phosphorus intake and/or lowering serum phosphate levels toward the normal range.

In certain embodiments, a subject receiving a composition comprising a polymeric amine that binds phosphate receives said composition to maintain serum phosphorus at a target level (e.g., below 5.5 mg/dL such as about 3.5 to about 5.5 mg/dL).

In some embodiments, a polymeric amine-containing composition comprises a polymeric amine that binds phosphate. In embodiments, a polymeric amine that binds phosphate is a sevelamer-based binding agent. In embodiments, a polymeric amine that binds phosphate is sevelamer hydrochloride or sevelamer carbonate. Exemplary polymeric amine-containing composition include sevelamer hydrochloride and sevelamer carbonate. In embodiments, a polymeric amine-containing composition comprises sevelamer hydrochloride or sevelamer carbonate.

In embodiments, a composition comprising a polymeric amine that binds phosphate comprises sevelamer hydrochloride or sevelamer carbonate.

A composition comprising a polymeric amine that binds phosphate can further comprise any of the excipients described herein (e.g., as described for formulations of Compound 1), as well as any combinations thereof.

In embodiments, the polymeric amine-containing composition is in the form of a powder.

In embodiments, the polymeric amine-containing composition is in the form of a tablet. Such tablets may be produced by tableting, e.g., direct compressing, the polymeric amine-containing composition as a pure powder, i.e., without containing any excipient. In other embodiments, suitable excipients may be added. Such as excipients include anti-adherents, binders, coatings, colors, disintegrants, flavors, glidants, lubricants, preservatives, sorbents, sweeteners, vehicles, and mixtures thereof.

In other embodiments, the tablet is obtained by compression of the granulated powders (i.e. the "inner phase") together with further excipients (the "outer phase"). The inner phase of the polymeric amine-containing composition may comprise the polymeric amine, and at least one excipient. The outer phase of the pharmaceutical composition according to the invention may comprise at least one excipient.

The pharmaceutical compositions according to the present invention may comprise a filler to provide processability.

Suitable filler materials are well-known to the art (see, e.g., Remington's Pharmaceutical Sciences, 18th Ed. (1990), Mack Publishing Co., Easton, Pa., pp. 1635-1636), and include microcrystalline cellulose, lactose and other carbohydrates, starch, pregelatinized starch, e.g., starch 1500R (Colorcon Corp.), corn starch, dicalcium phosphate, potassium bicarbonate, sodium bicarbonate, cellulose, calcium phosphate dibasic anhydrous, sugars, sodium chloride, and mixtures thereof, of which lactose, micro-crystalline cellulose, pregelatinized starch, and mixtures thereof, are preferred. Owing to its superior disintegration and compression properties, microcrystalline cellulose (Avicel grades, FMC Corp.), and mixtures comprising microcrystalline cellulose and one or more additional fillers, e.g., corn starch or pregelatinized starch, are particularly useful.

In embodiments, a composition comprising a polymeric amine that binds phosphate is formulated for oral administration.

In embodiments, a composition comprising a polymeric amine that binds phosphate is a tablet.

In embodiments, a composition comprising a polymeric amine that binds phosphate is a powder (e.g., a powder for oral suspension).

In embodiments, a composition comprising a polymeric amine that binds phosphate is administered continuously and/or indefinitely. In certain alternative embodiments, a composition comprising a polymeric amine that binds phosphate is administered on an as needed basis such that serum phosphorus is maintained at a level of about 3.5 to about 5.5 mg/dL.

Sevelamer Hydrochloride

In embodiments, a composition comprising a polymeric amine that binds phosphate is a composition comprising sevelamer hydrochloride.

In embodiments, a subject receives sevelamer hydrochloride for treating or preventing high blood phosphate levels (hyperphosphatemia). In embodiments, a subject receives sevelamer hydrochloride for treating or preventing impaired phosphorus excretion. In embodiments, a subject receives sevelamer hydrochloride for reducing the risk of cardiovascular disease, kidney failure, and mortality in subjects with CKD (chronic kidney disease). In embodiments, a subject receives sevelamer hydrochloride for reducing phosphorus intake and/or lowering serum phosphate levels toward the normal range. In certain embodiments, a subject receives sevelamer hydrochloride to maintain serum phosphorus at a target level (e.g., about 3.5 to about 5.5 mg/dL).

In certain embodiments, the sevelamer hydrochloride is administered in an amount such that serum phosphorus is maintained at a target level (e.g., below 5.5 mg/dL such as about 3.5 to about 5.5 mg/dL).

In embodiments, a subject receives sevelamer hydrochloride at a dose of about 400 mg to about 5000 mg. In embodiments, a subject receives sevelamer hydrochloride at a dose of about 400 mg, about 800 mg, about 1200 mg, about 1600 mg, about 2000 mg, about 2400 mg, about 2800 mg, about 3200 mg, about 3600 mg, about 4000 mg, about 4400 mg, or about 4800 mg. In embodiments, a subject receives sevelamer hydrochloride at a dose of about 800 mg, or about 1600 mg. In embodiments, a dose described herein is the initial dose at the beginning of a treatment. In embodiments, a dose described herein is the adjusted dose at a later time during the course of treatment. In embodiments, a dose described herein may be administered once daily, twice daily, or three times daily.

In embodiments, a subject is administered with 1600 mg of sevelamer hydrochloride once daily. In embodiment, a subject is initially administered with 1600 mg of sevelamer hydrochloride once daily. In embodiment, a subject is administered with 800 mg of sevelamer hydrochloride three times per day. In embodiment, a subject is initially administered with 800 mg of sevelamer hydrochloride three times per day. In embodiment, a subject is administered with 1600 mg of sevelamer hydrochloride three times per day. In embodiment, a subject is initially administered with 1600 mg of sevelamer hydrochloride three times per day.

In embodiments, a subject is administered one time per week, two times per week, or three times per week. In embodiments, a subject is administered a dose of sevelamer hydrochloride (e.g., 1600 mg) three times per week. For example, a subject may receive sevelamer hydrochloride (e.g., 1600 mg) on days 3, 5, and 7 of a seven-day period. In embodiments, a subject is administered a dose of Compound 1 (e.g., 150, 300, 450, or 600 mg Compound 1) daily. In embodiments, a subject is administered a dose of Compound 1 (e.g., 150, 300, 450, or 600 mg Compound 1) 3 times per week. In embodiments, a subject is administered a dose of Compound 1 (e.g., 150, 300, 450, or 600 mg Compound 1) 4 times per week (e.g., days 1, 3, 5, and 7 of a seven-day period).

In embodiments, a maximum dose of sevelamer hydrochloride is about 13 g per day. In embodiments, a maximum dose of sevelamer hydrochloride is about 14 g per day.

In embodiments, a subject receives sevelamer hydrochloride orally. In embodiments, a subject receives sevelamer hydrochloride as a tablet.

Sevelamer Carbonate

In embodiments, a composition comprising a polymeric amine is a composition comprising sevelamer carbonate.

In embodiments, a subject receives sevelamer carbonate for treating or preventing high blood phosphate levels (hyperphosphatemia). In embodiments, a subject receives sevelamer carbonate for treating or preventing impaired phosphorus excretion. In embodiments, a subject receives sevelamer carbonate for reducing the risk of cardiovascular disease, kidney failure, and mortality in subjects with CKD (chronic kidney disease). In embodiments, a subject receives sevelamer carbonate for reducing phosphorus intake and/or lowering serum phosphate levels toward the normal range. In certain embodiments, a subject receives sevelamer carbonate to maintain serum phosphorus at a target level (e.g., below 5.5 mg/dL such as about 3.5 to about 5.5 mg/dL).

In certain embodiments, the sevelamer carbonate is administered in an amount such that serum phosphorus is maintained at a target level (e.g., below 5.5 mg/dL such as about 3.5 to about 5.5 mg/dL).

In embodiments, a subject receives sevelamer carbonate at a dose of about 400 mg to about 5000 mg per day. In embodiments, a subject receives sevelamer carbonate at a dose of about 400 mg, about 800 mg, about 1200 mg, about 1600 mg, about 2000 mg, about 2400 mg, about 2800 mg, about 3200 mg, about 3600 mg, about 4000 mg, about 4400 mg, or about 4800 mg. In embodiments, a subject receives sevelamer carbonate at a dose of about 800 mg, or about 1600 mg. In embodiments, a dose described herein is the initial dose at the beginning of a treatment. In embodiments, a dose described herein is the adjusted dose at a later time during the course of treatment. In embodiments, a dose described herein may be administered once daily, twice daily, or three times daily.

In embodiment, a subject is administered with 1600 mg of sevelamer carbonate once daily. In embodiment, a subject is initially administered with 1600 mg of sevelamer carbonate once daily. In embodiment, a subject is administered with 800 mg of sevelamer carbonate three times per day. In embodiment, a subject is initially administered with 800 mg of sevelamer carbonate three times per day. In embodiment, a subject is administered with 1600 mg of sevelamer carbonate three times per day. In embodiment, a subject is initially administered with 1600 mg of sevelamer carbonate three times per day.

In embodiments, a subject is administered one time per week, two times per week, or three times per week. In embodiments, a subject is administered a dose of sevelamer carbonate (e.g., 1600 mg) three times per week. For example, a subject may receive sevelamer carbonate (e.g., 1600 mg) on days 3, 5, and 7 of a seven-day period. In embodiments, a subject is administered a dose of Compound 1 (e.g., 150, 300, 450, or 600 mg Compound 1) daily. In embodiments, a subject is administered a dose of Compound 1 (e.g., 150, 300, 450, or 600 mg Compound 1) 3 times per week. In embodiments, a subject is administered a dose of Compound 1 (e.g., 150, 300, 450, or 600 mg Compound 1) 4 times per week (e.g., days 1, 3, 5, and 7 of a seven-day period).

In embodiments, a maximum dose of sevelamer carbonate is about 14 g per day.

In embodiments, a subject receives sevelamer carbonate orally. In embodiments, a subject receives sevelamer carbonate as a tablet. In embodiments, a subject receives sevelamer carbonate as a powder. In embodiments, a subject receives sevelamer carbonate as a powder for oral suspension.

Organic Anion Transporter Inhibitors

In embodiments, a drug comprises an inhibitor of an organic anion transporter (e.g., OAT1/OAT3 or OATP1B1). In embodiments, a second drug is a drug comprising an inhibitor of an organic anion transporter (e.g., OAT1/OAT3 or OATP1B1). Accordingly, methods described herein can be useful for modulating drug-drug interactions between Compound 1 and an inhibitor of an organic anion transporter (e.g., OAT1/OAT3 or OATP1B1) and/or one or more metabolites thereof, including as described herein.

In embodiments, a drug (e.g., a second drug) comprises an inhibitor of an organic anion transporter (e.g., OAT1/OAT3 or OATP1B1). In embodiments, an inhibitor of an organic anion transporter is an OAT1/OAT3 inhibitor (e.g., OAT1 inhibitor and/or OAT3 inhibitor). In embodiments, an OAT1/OAT3 inhibitor is probenecid. In embodiments, an inhibitor of an organic anion transporter is an OAT1 inhibitor. In embodiments, an OAT1 inhibitor is probenecid or rifampicin. In embodiments, an inhibitor of an organic anion transporter is an OAT3 inhibitor. In embodiments, an OAT3 inhibitor is cimetidine, diclofenac, furosemide, gemfibrozil, ibuprofen, or probenecid. In embodiments, an inhibitor of an organic anion transporter is an OATP1B1 inhibitor. In embodiments, an OATP1B1 inhibitor is cyclosporine or rifampin. In embodiments, a drug (e.g., a second drug) is probenecid.

In embodiments, the dosage amount of a drug (e.g., a second drug) that is an organic anion transporter (e.g., an OAT1/OAT3 inhibitor and/or an OATP1B1 inhibitor) is adjusted when co-administered with Compound 1. In embodiments, the dosage amount is increased. In embodiments, the dosage amount is decreased. In embodiments, the dosage amount of a drug (e.g., a second drug) that is an organic anion transporter (e.g., an OAT1/OAT3 inhibitor and/or an OATP1B1 inhibitor) is not adjusted when co-administered with Compound 1. In embodiments, the dosage amount of a drug (e.g., a first drug) that is Compound 1 is adjusted when co-administered with an organic anion transporter (e.g., an OAT1/OAT3 inhibitor and/or an OATP1B1 inhibitor). In embodiments, the dosage amount is increased. In embodiments, the dosage amount is decreased. In embodiments, the dosage amount of a drug (e.g., a first drug) that is Compound 1 is not adjusted when co-administered with an organic anion transporter (e.g., an OAT1/OAT3 inhibitor and/or an OATP1B1 inhibitor).

Still further embodiments of methods comprising treating a disease or a condition using an organic anion transporter (e.g., an OAT1/OAT3 inhibitor and/or an OATP1B1 inhibitor) include those described herein.

OAT1/OAT3 Inhibitor

In embodiments, a drug comprises an OAT1/OAT3 inhibitor (e.g., an OAT1 inhibitor and/or OAT3 inhibitor). In embodiments, a second drug is a drug comprising an OAT1/OAT3 inhibitor (e.g., an OAT1 inhibitor and/or OAT3 inhibitor). Accordingly, methods described herein can be useful for modulating drug-drug interactions between Compound 1 an OAT1/OAT3 inhibitor (e.g., an OAT1 inhibitor and/or OAT3 inhibitor) and/or one or more metabolites thereof, including as described herein.

Exemplary OAT1/OAT3 inhibitors include but are not limited to probenecid, rifampicin, cimetidine, diclofenac, furosemide, gemfibrozil, ibuprofen, and probenecid. In embodiments, an OAT1/OAT3 inhibitor is an OAT1 inhibitor (e.g., probenecid or rifampicin). In embodiments, an OAT1/OAT3 inhibitor is an OAT3 inhibitor (e.g., cimetidine, diclofenac, furosemide, gemfibrozil, ibuprofen, or probenecid). In embodiments, an OAT1/OAT3 inhibitor is probenecid. In embodiments, an OAT1/OAT3 inhibitor is rifampicin.

In embodiments, an OAT1/OAT3 inhibitor (e.g., probenecid or rifampicin) is administered concomitantly (e.g., simultaneously) with Compound 1. In embodiments, an OAT1/OAT3 inhibitor (e.g., probenecid or rifampicin) is not administered concomitantly (e.g., simultaneously) with Compound 1 (e.g., administration of two drugs is separated by a time period as described herein).

In embodiments, the dosage amount of a drug (e.g., a second drug) that is an OAT1/OAT3 inhibitor (e.g., probenecid or rifampicin) is adjusted when co-administered with Compound 1. In embodiments, the dosage amount is increased. In embodiments, the dosage amount is decreased. In embodiments, the dosage amount of a drug (e.g., a second drug) that is an OAT1/OAT3 inhibitor (e.g., probenecid or rifampicin) is not adjusted when co-administered with Compound 1. In embodiments, the dosage amount of a drug (e.g., a first drug) that is Compound 1 is adjusted when co-administered with an OAT1/OAT3 inhibitor (e.g., probenecid or rifampicin). In embodiments, the dosage amount is increased. In embodiments, the dosage amount is decreased. In embodiments, the dosage amount of a drug (e.g., a first drug) that is Compound 1 is not adjusted when co-administered with an OAT1/OAT3 inhibitor (e.g., probenecid or rifampicin).

Still further embodiments of methods comprising treating a disease or a condition using an OAT1/OAT3 inhibitor include those described herein.

Probenecid

In embodiments, a drug (e.g., a second drug) is probenecid, which can be a pan-UGT inhibitor and/or an OAT1/OAT3 inhibitor. Accordingly, methods described herein can be useful for modulating drug-drug interactions between Compound 1 and a pan-UGT inhibitor (e.g., probenecid) and/or one or more metabolites thereof, including as described herein. Methods described herein can also be useful for modulating drug-drug interactions between Compound 1 and an OAT1/OAT3 inhibitor (e.g., probenecid) and/or one or more metabolites thereof, including as described herein.

In embodiments, subject receives probenecid for treating or preventing gout, gouty arthritis, and/or other medical conditions. In embodiments, a subject receives probenecid at a dose of about 250 mg, 500 mg, 750 mg, 1000 mg, or more than 1000 mg per day. In embodiments, a subject receives probenecid at a dose of about 500 mg per day. In embodiments, a dose described herein is the initial dose at the beginning of a treatment. In embodiments, a dose described herein is the adjusted dose at a later time during the course of treatment.

In certain embodiments, probenecid is administered continuously and/or indefinitely. In certain embodiments, probenecid is administered once, twice, or three times per day.

In embodiments, probenecid is administered concomitantly (e.g., simultaneously) with Compound 1. In embodiments, probenecid is not administered concomitantly (e.g., simultaneously) with Compound 1 (e.g., administration of two drugs is separated by a time period as described herein).

In embodiments, the dosage amount of probenecid is adjusted compared to the amount when administered in the absence of a Compound 1 or in monotherapy (e.g., adjusted as described herein). In embodiments, the dosage amount of probenecid is not adjusted when co-administered with Compound 1. In embodiments, the dosage amount of Compound 1 is adjusted compared to the amount when administered in the absence of probenecid or in monotherapy (e.g., adjusted as described herein). In embodiments, the dosage amount of Compound 1 is not adjusted when co-administered with probenecid.

Rifampin

In embodiments, a drug (e.g., a second drug) is rifampin, which can be an OATP1B1 inhibitor and/or an OAT1 inhibitor. In embodiments, subject receives rifampin for treating or preventing tuberculosis, meningococcal carriers, and/or other medical conditions. In embodiments, a subject receives rifampin at a dose of about 5 mg/kg, 10 mg/kg, 15 mg/kg, 20 mg/kg, or more than 20 mg/kg per day.

In embodiments, a subject receives rifampin at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, or more than about 1200 mg per day. In embodiments, a subject receives rifampin at a dose of about 600 mg per day. In embodiments, a dose described herein is the initial dose at the beginning of a treatment. In embodiments, a dose described herein is the adjusted dose at a later time during the course of treatment.

In certain embodiments, a rifampin drug is administered continuously and/or indefinitely. In certain embodiments, a rifampin drug is administered once, twice, or three times per day.

In embodiments, a rifampin drug is administered concomitantly (e.g., simultaneously) with Compound 1. In embodiments, a rifampin drug is not administered concomitantly (e.g., simultaneously) with Compound 1 (e.g., administration of two drugs is separated by a time period as described herein).

In embodiments, the dosage amount of rifampin is adjusted compared to the amount when administered in the absence of a Compound 1 or in monotherapy (e.g., adjusted as described herein). In embodiments, the dosage amount of rifampin is not adjusted when co-administered with Compound 1. In embodiments, the dosage amount of Compound 1 is adjusted compared to the amount when administered in the absence of a rifampin drug or in monotherapy (e.g., adjusted as described herein). In embodiments, the dosage amount of Compound 1 is not adjusted when co-administered with a rifampin.

OATP1B1 Inhibitor

In embodiments, a drug comprises an OATP1B1 inhibitor (e.g., cyclosporine). In embodiments, a second drug is a drug comprising an OATP1B1 inhibitor (e.g., cyclosporine). Accordingly, methods described herein can be useful for modulating drug-drug interactions between Compound 1 an OATP1B1 inhibitor (e.g., cyclosporine) and/or one or more metabolites thereof, including as described herein.

Exemplary OATP1B1 inhibitors include but are not limited to cyclosporine, gemfibrozil, statins, antibiotics, and antiretroviral drugs. In embodiments, an OATP1B1 inhibitor is cyclosporine.

In embodiments, an OATP1B1 inhibitor (e.g., cyclosporine) is administered concomitantly (e.g., simultaneously) with Compound 1. In embodiments, an OATP1B1 inhibitor (e.g., cyclosporine) is not administered concomitantly (e.g., simultaneously) with Compound 1 (e.g., administration of two drugs is separated by a time period as described herein).

In embodiments, the dosage amount of a drug (e.g., a second drug) that is an OATP1B1 inhibitor (e.g., cyclosporine) is adjusted when co-administered with Compound 1. In embodiments, the dosage amount is increased. In embodiments, the dosage amount is decreased. In embodiments, the dosage amount of a drug (e.g., a second drug) that is an OATP1B1 inhibitor (e.g., cyclosporine) is not adjusted when co-administered with Compound 1. In embodiments, the dosage amount of a drug (e.g., a first drug) that is Compound 1 is adjusted when co-administered with an OATP1B1 inhibitor (e.g., cyclosporine). In embodiments, the dosage amount is increased. In embodiments, the dosage amount is decreased. In embodiments, the dosage amount of a drug (e.g., a first drug) that is Compound 1 is not adjusted when co-administered with an OATP1B1 inhibitor (e.g., cyclosporine).

Still further embodiments of methods comprising treating a disease or a condition using an OATP1B1 inhibitor (e.g., cyclosporine) include those described herein.

Cyclosporine

In embodiments, a drug (e.g., a second drug) is cyclosporine, which can be a BCRP inhibitor, an OATP1B1 inhibitor and/or a P-glycoprotein 1 (Pgp) inhibitor. Accordingly, methods described herein can be useful for modulating drug-drug interactions between Compound 1 and a BCRP inhibitor (e.g., cyclosporine) and/or one or more metabolites thereof, including as described herein. Methods described herein can also be useful for modulating drug-drug interactions between Compound 1 and an OATP1B1 inhibitor (e.g., cyclosporine) and/or one or more metabolites thereof, including as described herein. In addition, Methods described herein can also be useful for modulating drug-drug interactions between Compound 1 and a P-glycoprotein 1 inhibitor (e.g., cyclosporine) and/or one or more metabolites thereof, including as described herein.

In embodiments, subject receives cyclosporine for treating or preventing the prophylaxis of organ rejection in kidney, liver, and heart allogeneic transplants. In embodiments, subject receives cyclosporine for treating or preventing rheumatoid arthritis, psoriasis and/or other medical conditions. In embodiments, a subject receives cyclosporine at a dose of about 0.5 mg/kg/day, 1 mg/kg/day, 1.5 mg/kg/day, 2 mg/kg/day, 2.5 mg/kg/day, 3 mg/kg/day, 3.5 mg/kg/day, 4 mg/kg/day, 4.5 mg/kg/day, 5 mg/kg/day, 6 mg/kg/day, 7 mg/kg/day, 8 mg/kg/day, 9 mg/kg/day, 10 mg/kg/day, 11 mg/kg/day, 12 mg/kg/day, or more than 12 mg/kg/day. In embodiments, a subject receives cyclosporine at a dose of about 250 mg, 500 mg, 750 mg, 1000 mg, 1250 mg, 1500 mg, 1750 mg, 2000 mg, or more than 2000 mg per day. In embodiments, a subject receives cyclosporine at a dose of about 500 mg per day. In embodiments, a dose described herein is the initial dose at the beginning of a treatment. In embodiments, a dose described herein is the adjusted dose at a later time during the course of treatment.

In certain embodiments, a cyclosporine drug is administered continuously and/or indefinitely. In certain embodiments, a cyclosporine drug is administered once, twice, or three times per day.

In embodiments, a cyclosporine drug is administered concomitantly (e.g., simultaneously) with Compound 1. In embodiments, a cyclosporine drug is not administered concomitantly (e.g., simultaneously) with Compound 1 (e.g., administration of two drugs is separated by a time period as described herein).

In embodiments, the dosage amount of cyclosporine is adjusted compared to the amount when administered in the absence of a Compound 1 or in monotherapy (e.g., adjusted as described herein). In embodiments, the dosage amount of cyclosporine is not adjusted when co-administered with Compound 1. In embodiments, the dosage amount of Compound 1 is adjusted compared to the amount when administered in the absence of a cyclosporine drug or in monotherapy (e.g., adjusted as described herein). In embodiments, the dosage amount of Compound 1 is not adjusted when co-administered with a cyclosporine.

P-Glycoprotein Transporter (P-Rp) Substrate

In embodiments, a drug comprises a p-glycoprotein transporter (P-gp) substrate (e.g., digoxin). In embodiments, a second drug is a drug comprising a p-glycoprotein transporter substrate (e.g., digoxin). Accordingly, methods described herein can be useful for modulating drug-drug interactions between Compound 1 and a p-glycoprotein transporter substrate (e.g., digoxin) and/or one or more metabolites thereof, including as described herein.

Exemplary p-glycoprotein transporter substrates include but are not limited to calcium channel blockers, cyclosporin, dabigatran etexilate, digoxin, erythromycin, loperamide, protease inhibitors and tacrolimus. In embodiments, a p-glycoprotein transporter substrate is digoxin.

In embodiments, a p-glycoprotein transporter substrate (e.g., digoxin) is administered concomitantly (e.g., simultaneously) with Compound 1. In embodiments, a p-glycoprotein transporter substrate (e.g., digoxin) is not administered concomitantly (e.g., simultaneously) with Compound 1 (e.g., administration of two drugs is separated by a time period as described herein).

In embodiments, the dosage amount of a drug (e.g., a second drug) that is a p-glycoprotein transporter substrate (e.g., digoxin) is adjusted when co-administered with Compound 1. In embodiments, the dosage amount is increased. In embodiments, the dosage amount is decreased. In embodiments, the dosage amount of a drug (e.g., a second drug) that is a p-glycoprotein transporter substrate (e.g., digoxin) is not adjusted when co-administered with Compound 1. In embodiments, the dosage amount of a drug (e.g., a first drug) that is Compound 1 is adjusted when co-administered with a p-glycoprotein transporter substrate (e.g., digoxin). In embodiments, the dosage amount is increased. In embodiments, the dosage amount is decreased. In embodiments, the dosage amount of a drug (e.g., a first drug) that is Compound 1 is not adjusted when co-administered with a p-glycoprotein transporter substrate (e.g., digoxin).

Still further embodiments of methods comprising treating a disease or a condition using a p-glycoprotein transporter substrate (e.g., digoxin) include those described herein.

Digoxin

In embodiments, a drug (e.g., a second drug) is digoxin. In embodiments, subject receives digoxin for treating or preventing heart failure (e.g., for increasing myocardial contractility, and/or control of resting ventricular rate), atrial fibrillation, and/or other medical conditions. In embodiments, a subject receives digoxin at a dose of about 5 mcg/kg, 10 mcg/kg, 15 mcg/kg, 20 mcg/kg, 25 mcg/kg, 30 mcg/kg, 35 mcg/kg, 40 mcg/kg, 45 mcg/kg, or more than 45 mcg/kg. In embodiments, a subject receives digoxin at a dose of about 0.25 mg, 0.5 mg, 0.75 mg, 1 mg, 1.25 mg, or more than 1.25 mg per day. In embodiments, a subject receives digoxin at a dose of about 0.5 mg per day. In embodiments, a dose described herein is the initial dose at the beginning of a treatment. In embodiments, a dose described herein is the adjusted dose at a later time during the course of treatment.

In certain embodiments, a digoxin drug is administered continuously and/or indefinitely. In certain embodiments, a digoxin drug is administered once, twice, or three times per day.

In embodiments, a digoxin drug is administered concomitantly (e.g., simultaneously) with Compound 1. In embodiments, a digoxin drug is not administered concomitantly (e.g., simultaneously) with Compound 1 (e.g., administration of two drugs is separated by a time period as described herein).

In embodiments, the dosage amount of a digoxin drug is adjusted compared to the amount when administered in the absence of Compound 1 or in monotherapy (e.g., adjusted as described herein). In embodiments, the dosage amount of a digoxin drug is not adjusted when co-administered with Compound 1. In embodiments, the dosage amount of Compound 1 is adjusted compared to the amount when administered in the absence of a digoxin drug or in monotherapy (e.g., adjusted as described herein). In embodiments, the dosage amount of Compound 1 is not adjusted when co-administered with a digoxin.

OAT1/OAT3 Substrate

In embodiments, a drug comprises an OAT1/OAT3 substrate (e.g., an OAT1 substrate and/or OAT3 substrate). In embodiments, a second drug is a drug comprising an OAT1/OAT3 substrate (e.g., an OAT1 substrate and/or OAT3 substrate). Accordingly, methods described herein can be useful for modulating drug-drug interactions between Compound 1 an OAT1/OAT3 substrate (e.g., an OAT1 substrate and/or OAT3 substrate) and/or one or more metabolites thereof, including as described herein.

Exemplary OAT1/OAT3 substrates (e.g., OAT1 substrates and/or OAT3 substrates) include but are not limited to adefovir, cefaclor, ceftizoxime, cimetidine, famotidine, furosemide, oseltamivir carboxylate, penicillin G, and sitagliptin.

In embodiments, an OAT1/OAT3 substrate is an OAT1 substrate (e.g., adefovir). In embodiments, an OAT1/OAT3 substrate is an OAT3 substrate (e.g., cefaclor, ceftizoxime, cimetidine, famotidine, furosemide, oseltamivir carboxylate, penicillin G, or sitagliptin). In embodiments, an OAT1/OAT3 substrate is adefovir.

In embodiments, an OAT1/OAT3 substrate (e.g., adefovir) is administered concomitantly (e.g., simultaneously) with Compound 1. In embodiments, an OAT1/OAT3 substrate (e.g., adefovir) is not administered concomitantly (e.g., simultaneously) with Compound 1 (e.g., administration of two drugs is separated by a time period as described herein).

In embodiments, the dosage amount of a drug (e.g., a second drug) that is an OAT1/OAT3 substrate (e.g., adefovir) is adjusted when co-administered with Compound 1. In embodiments, the dosage amount is increased. In embodiments, the dosage amount is decreased. In embodiments, the dosage amount of a drug (e.g., a second drug) that is OAT1/OAT3 substrate (e.g., adefovir) is not adjusted when co-administered with Compound 1. In embodiments, the dosage amount of a drug (e.g., a first drug) that is Compound 1 is adjusted when co-administered with an OAT1/OAT3 substrate (e.g., adefovir). In embodiments, the dosage amount is increased. In embodiments, the dosage amount is decreased. In embodiments, the dosage amount of a drug (e.g., a first drug) that is Compound 1 is not adjusted when co-administered with an OAT1/OAT3 substrate (e.g., adefovir).

Still further embodiments of methods comprising treating a disease or a condition using an OAT1/OAT3 substrate (e.g., adefovir) include those described herein.

In embodiments, an OAT1/OAT3 substrate is not furosemide.

Adefovir

In embodiments, a drug (e.g., a second drug) is adefovir. In embodiments, subject receives adefovir for treating or preventing chronic hepatitis B and/or other medical conditions. In embodiments, a subject receives adefovir at a dose of about 2 mg, 4 mg, 6 mg, 8 mg, 10 mg, or more than 10 mg per day. In embodiments, a subject receives adefovir at a dose of about 10 mg per day. In embodiments, a dose described herein is the initial dose at the beginning of a treatment. In embodiments, a dose described herein is the adjusted dose at a later time during the course of treatment.

In certain embodiments, an adefovir drug is administered continuously and/or indefinitely. In certain embodiments, an adefovir drug is administered once, twice, or three times per day. In certain embodiments, an adefovir drug is administered once per day, once per 2 days, once per 3 days, or once per 7 days.

In embodiments, an adefovir drug is administered concomitantly (e.g., simultaneously) with Compound 1. In embodiments, an adefovir drug is not administered concomitantly (e.g., simultaneously) with Compound 1 (e.g., administration of two drugs is separated by a time period as described herein).

In embodiments, the dosage amount of an adefovir drug is adjusted compared to the amount when administered in the absence of Compound 1 or in monotherapy (e.g., adjusted as described herein). In embodiments, the dosage amount of an adefovir drug is not adjusted when co-administered with Compound 1. In embodiments, the dosage amount of Compound 1 is adjusted compared to the amount when administered in the absence of an adefovir drug or in monotherapy (e.g., adjusted as described herein). In embodiments, the dosage amount of Compound 1 is not adjusted when co-administered with an adefovir drug.

Diseases Associated with HIF Prolyl Hydroxylase Modulation

In certain embodiments, the methods of the inventions include subjects having a disease associated with HIF prolyl hydroxylase modulation.

Diseases associated with HIF prolyl hydroxylase modulation include Peripheral Vascular Disease (PVD); Coronary Artery Disease (CAD); heart failure; ischemia; anemia; wound healing; ulcers; ischemic ulcers; inadequate blood supply; poor capillary circulation; small artery atherosclerosis; venous stasis; atherosclerotic lesions (e.g., in coronary arteries); angina; myocardial infarction; diabetes; hypertension; Buerger's disease; diseases associated with abnormal levels of VEGF, GAPDH, and/or EPO; Crohn's disease; ulcerative colitis; psoriasis; sarcoidosis; rheumatoid arthritis; hemangiomas; Osler-Weber-vasculitis disease; hereditary hemorrhagic telangiectasia; solid or blood borne tumors and acquired immune deficiency syndrome; atrial arrhythmias; ischemic tissue damage in tissues such as: cardiac tissue, such as myocardium and cardiac ventricles, skeletal muscle, neurological tissue, such as from the cerebellum, internal organs, such as the stomach, intestine, pancreas, liver, spleen, and lung; and distal appendages such as fingers and toes.

Specifically, the methods provided herein include administering Compound 1 and another therapeutic agent (e.g., a drug as described herein) to a subject having, inter alia, Peripheral Vascular Disease (PVD); Coronary Artery Disease (CAD); heart failure; ischemia; anemia; wound healing; ulcers; ischemic ulcers; inadequate blood supply; poor capillary circulation; small artery atherosclerosis; venous stasis; atherosclerotic lesions (e.g., in coronary arteries); angina; myocardial infarction; diabetes; hypertension; Buerger's disease; diseases associated with abnormal levels of VEGF, GAPDH, and/or EPO; Crohn's disease; ulcerative colitis; psoriasis; sarcoidosis; rheumatoid arthritis; hemangiomas; Osler-Weber-vasculitis disease; hereditary hemorrhagic telangiectasia; solid or blood borne tumors and acquired immune deficiency syndrome; atrial arrhythmias; ischemic tissue damage in tissues such as: cardiac tissue, such as myocardium and cardiac ventricles, skeletal muscle, neurological tissue, such as from the cerebellum, internal organs, such as the stomach, intestine, pancreas, liver, spleen, and lung; and distal appendages such as fingers and toes.

In certain embodiments, the methods provided herein include administering Compound 1 and another therapeutic agent (e.g., a drug as described herein) to a subject having anemia, as such anemia secondary to non-dialysis dependent chronic kidney disease.

In embodiments, a subject has renal anemia (anemia secondary to or associated with chronic kidney disease).

In certain embodiments, the chronic kidney disease is stage 3, 4, or 5 chronic kidney disease. In certain embodiments, the chronic kidney disease is pre-dialysis chronic kidney disease. In other embodiments, the chronic kidney disease is non-dialysis dependent chronic kidney disease. In still other embodiments, the subject has not been previously treated for anemia, such as anemia secondary to chronic kidney disease. In alternative embodiments, the subject has been previously treated for anemia, such as anemia secondary to chronic kidney disease.

Doses and Dosing Regimens of Compound 1

The specific doses for uses of a Compound 1 can be administered in any manner known to the skilled artisan. Exemplary doses are provided herein, including in the Examples.

In embodiments, the dose of Compound 1 is about 150 mg to about 600 mg, about 150 mg to 750 mg, about 150 mg to 900 mg, about 150 mg to 1200 mg, about 150 mg to 1500 mg, about 75 mg to 1200 mg, about 75 mg to 1500 mg, or about 75 mg to 1800 mg. In embodiments, the dose of Compound 1 is about 75 mg to about 1200 mg, about 150 mg to about 600 mg, or about 150 mg to about 750 mg. In embodiments, the dose of Compound 1 is about 75 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, or about 1800 mg. In embodiments, the dose of Compound 1 is at least about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, or about 1800 mg. In embodiments, the dose of Compound 1 is no more than about 75 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, or about 1800 mg.

In embodiments, such doses may be administered orally, once daily, twice daily, three times daily, three times per week, or once per week.

In embodiments, such a dose is the initial dose at the beginning of a treatment. In embodiments, such a dose is the adjusted dose at a later time during the course of treatment.

Doses of Compound 1 may be taken orally. Doses of Compound 1 may be taken while fasting, together with fluids, or together with food of any kind. In specific embodiments, doses of Compound 1 may be taken or 1, 2, 3, 4, 5, 6, 7, 8, 9, 10, 11, or 12 hours after a meal, or 1, 2, 3, 4, 5, 6, 7, 8, 9, 10, 11, or 12 hours before a meal. Doses of Compound 1 may be taken at any time of day. In certain embodiments, repeat doses are administered at the same time during the day. In certain embodiments, the dose doses are administered in the morning, around mid-day, or in the evening. In certain embodiments, the doses are administered between 4:00 am and 2:00 pm. In certain embodiments, the doses are administered between 5:00 am and 1:00 pm. In certain embodiments, the doses are administered between 6:00 am and 12:00 noon. In certain embodiments, the doses are administered between 7:00 am and 11:00 am. In certain embodiments, the doses are administered between 8:00 am and 10:00 am. In certain embodiments, the doses are administered before, during, or after breakfast. Administration and dosing regimens may be adjusted as described herein.

Dose levels of the compound include 150, 300, 450, and 600 mg. Thereafter, the medication is taken once daily during the course of treatment. The subject should take the study medication with 4 ounces of water or other oral beverage, regardless of food intake. The dose is taken at approximately the same time each day, preferably between 7 AM and 2 PM.

In a specific embodiment, a subject is initially treated with 300 mg of Compound 1 daily (300 mg/day).

In a specific embodiment, a subject is initially treated with 450 mg of Compound 1 daily (450 mg/day).

This section provides several exemplary doses for Compound 1. In certain embodiments, such a dose is the initial dose at the beginning of a treatment. In other embodiments, such a dose is the adjusted dose at a later time during the course of treatment.

In certain embodiments, the daily dose of Compound 1 is between about 150 mg and about 600 mg. In certain embodiments, the daily dose of the compound is between about 150 mg and about 300 mg or about 300 and about 600 mg. In certain embodiments, the daily dose is about 150 mg, 200 mg, 250 mg, 300 mg, 350 mg, 400 mg, 450 mg, 500 mg, 550 mg, or 600 mg of Compound 1, or a pharmaceutically acceptable salt thereof. In certain embodiments, the daily dose of Compound 1, or a pharmaceutically acceptable salt thereof, is at least about 150 mg, at least about 300 mg, at least about 450 mg, or even at least about 600 mg.

In certain embodiments, the daily dose is about 150 mg, about 300 mg, about 450 mg, or about 600 mg of Compound 1. In certain embodiments, the daily dose Compound 1 is about 150 mg, about 300 mg, about 450 mg, or about 600 mg. In embodiments, a maximum dose is about 600 mg.

In embodiments, a starting dose is about 300 mg, and the dose is adjusted (e.g., according to the patient's condition). In embodiments, a maximum dose is about 600 mg.

In embodiments, a starting dose is about 450 mg, and the dose is adjusted (e.g., according to the patient's condition). In embodiments, a maximum dose is about 600 mg.

In certain embodiments, a daily dose of 450 mg of Compound 1 may be decreased by about 150 mg, such that the daily dose of the compound is about 300 mg. In certain embodiments, a daily dose of Compound 1 may be decreased by about 300 mg, such that the daily dose of the compound is about 150 mg. In certain embodiments, the daily dose Compound 1 may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose of Compound 1, or a pharmaceutically acceptable salt thereof, may be increased or decreased by an amount between about 75 mg and about 250 mg, about 100 mg and about 225 mg, or about 125 mg and about 200 mg. In certain such embodiments, the daily dose Compound 1 does not exceed about 600 mg.

Dose Adjustments

In certain embodiments, the dose may be adjusted by administering to a patient having anemia an initial daily dose of a compound which is {[5-(3-chlorophenyl)-3-hydroxypyridine-2-carbonyl]amino}acetic acid (Compound 1) or a pharmaceutically acceptable salt, solvate, or hydrate thereof administered in a formulation as described herein; taking a first measurement of the hemoglobin level in the patient and subsequently taking a second measurement of the hemoglobin level in the patient, wherein if the hemoglobin level in the patient at the second measurement is less than about 10.0 g/dL and the level of hemoglobin has decreased by less than about 0.5 g/dL as compared to the level at the first measurement; or if the hemoglobin level in the patient at the second measurement is less than about 10.0 g/dL and the level of hemoglobin has changed by up to about 0.4 g/dL as compared to the level at the first measurement; or if the hemoglobin level in the patient at the second measurement is between about 10.0 and about 10.9 g/dL and the level of hemoglobin has decreased by less than about 0.5 g/dL as compared to the level at the first measurement; then administering an adjusted daily dose of the compound that is greater than the initial daily dose. In certain such embodiments, the adjusted daily dose of the compound is about 150 mg greater than the initial daily dose.

In certain embodiments, the dose may be adjusted by administering to a patient having anemia an initial daily dose of a compound which is {[5-(3-chlorophenyl)-3-hydroxypyridine-2-carbonyl]amino}acetic acid, or a pharmaceutically acceptable salt thereof, administered in a formulation as described herein; taking a first measurement of the hemoglobin level in the patient and subsequently taking a second measurement of the hemoglobin level in the patient, wherein if the hemoglobin level in the patient at the second measurement is less than about 10.0 g/dL and the level of hemoglobin has increased by greater than about 1.5 g/dL as compared to the level at the first measurement; or if the hemoglobin level in the patient at the second measurement is between about 10.0 and about 10.9 g/dL and the level of hemoglobin has increased by greater than about 1.5 g/dL as compared to the level at the first measurement; or if the hemoglobin level in the patient at the second measurement is between about 11.0 and about 12.2 g/dL and the level of hemoglobin has increased by between about 1.0 and about 1.4 g/dL as compared to the level at the first measurement; or if the hemoglobin level in the patient at the second measurement is between about 12.3 and about 12.9 g/dL and the level of hemoglobin has decreased by up to about 0.4 g/dL or increased by up to about 0.4 g/dL as compared to the at the first measurement; or if the hemoglobin level in the patient at the second measurement is between about 12.3 and about 12.9 g/dL and the level of hemoglobin has increased by about 0.5 to about 0.9 g/dL as compared to the level at the first measurement; then administering an adjusted daily dose of the compound that is less than the initial daily dose. In certain such embodiments, the adjusted daily dose of the compound is about 150 mg less than the initial daily dose. In certain embodiments, the lowest dose level is 150 mg per day. Patients already on the lowest dose level will continue on 150 mg per day unless their Hgb increases to ≥13.0 g/dL.

In certain embodiments, the dose may be adjusted by administering to a patient having anemia an initial daily dose of a compound which is {[5-(3-chlorophenyl)-3-hydroxypyridine-2-carbonyl]amino}acetic acid (Compound 1) or a pharmaceutically acceptable salt thereof, administered in a formulation; taking a first measurement of the hemoglobin level in the patient and subsequently taking a second measurement of the hemoglobin level in the patient, wherein if the hemoglobin level in the patient at the second measurement is between about 11.0 and about 12.2 g/dL and the level of hemoglobin has increased by greater than about 1.5 g/dL as compared to the level at the first measurement; or if the hemoglobin level in the patient at the second measurement is between about 12.3 and about 12.9 g/dL and the level of hemoglobin has increased by between about 1.0 and about 1.4 g/dL as compared to the level at the first measurement; or if the hemoglobin level in the patient at the second measurement is between about 12.3 and about 12.9 g/dL and the level of hemoglobin has increased by greater than about 1.5 g/dL as compared to the level at the first measurement; then administering an adjusted daily dose of the compound that is less than the initial daily dose. In certain such embodiments, the adjusted daily dose of the compound is about 300 mg less than the initial daily dose. In certain embodiments, the lowest dose level is 150 mg per day. Patients already on the lowest dose level will continue on 150 mg per day unless their Hgb increases to ≥13.0 g/dL.

In certain embodiments, the dose may be adjusted by administering to a patient having anemia an initial daily dose of a compound which is {[5-(3-chlorophenyl)-3-hydroxypyridine-2-carbonyl]amino}acetic acid (Compound 1) or a pharmaceutically acceptable salt thereof, administered in a formulation; taking a first measurement of the hemoglobin level in the patient and subsequently taking a second measurement of the hemoglobin level in the patient, wherein if the hemoglobin level in the patient at the second measurement is equal to or above 13.0 g/dL, then administering an adjusted daily dose of the compound that is less than the initial daily dose. In certain such embodiments, dosing is suspended. In certain such embodiments, dosing will be suspended if Hgb rises to 13 g/dL, and will not be restarted until Hgb reduces to ≤12.5 g/dL. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxypyridine-2-carbonyl]amino}acetic acid (Compound 1) or a pharmaceutically acceptable salt thereof; taking a first measurement of the hemoglobin level in the patient and subsequently taking a second measurement of the hemoglobin level in the patient, wherein if the hemoglobin level in the patient at the second measurement is equal to or above 12.5 g/dL, then administering an adjusted daily dose of the compound that is less than the initial daily dose. In certain such embodiments, dosing is suspended. In certain such embodiments, dosing will be suspended if Hgb rises to ≥12.5 g/dL, and will not be restarted until Hgb reduces to ≤12.0 g/dL. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxypyridine-2-carbonyl]amino}acetic acid (Compound 1) or a pharmaceutically acceptable salt thereof; taking a first measurement of the hemoglobin level in the patient and subsequently taking a second measurement of the hemoglobin level in the patient, wherein if the hemoglobin level in the patient at the second measurement is equal to or above 13.0 g/dL if the patient is an adult male or 12.5 g/dL if the patient is an adult female, then administering an adjusted daily dose of the compound that is less than the initial daily dose. In certain such embodiments, dosing is suspended. In certain such embodiments, dosing will be suspended if Hgb rises to 13.0 g/dL if the patient is an adult male or to 12.5 g/dL if the patient is an adult female, and will not be restarted until Hgb reduces to ≤12.5 g/dL if the patient is an adult male or 12.0 g/dL if the patient is an adult female. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxypyridine-2-carbonyl]amino}acetic acid (Compound 1) or a pharmaceutically acceptable salt thereof, administered in a formulation; taking a first measurement of the hemoglobin level in the patient and subsequently taking a second measurement of the hemoglobin level in the patient, wherein if the hemoglobin level in the patient at the second measurement is less than about 9.5 to 10.5 g/dL or about 9.75 to 10.25 g/dL and the level of hemoglobin has decreased by less than about 0.2 to 0.8, about 0.3 to 0.7, or about 0.4 to 0.6 g/dL as compared to the level at the first measurement; or if the hemoglobin level in the patient at the second measurement is less than about 9.5 to 10.5 g/dL or about 9.75 to 10.25 g/dL and the level of hemoglobin has changed by up to about 0.1 to 0.7, about 0.2 to 0.6, or about 0.3 to 0.5 g/dL as compared to the level at the first measurement; or if the hemoglobin level in the patient at the second measurement is between about 9.5 to 10.5 g/dL or about 9.75 to 10.25 g/dL and about 10.4 to 11.4 g/dL or about 10.65 to 11.15 g/dL and the level of hemoglobin has decreased by less than about 0.2 to 0.8, about 0.3 to 0.7, or about 0.4 to 0.6 g/dL as compared to the level at the first measurement; then administering an adjusted daily dose of the compound that is greater than the initial daily dose. In certain such embodiments, the adjusted daily dose of the compound is about 150 mg greater than the initial daily dose.

In certain embodiments, the dose may be adjusted by administering to a patient having anemia an initial daily dose of a compound which is {[5-(3-chlorophenyl)-3-hydroxypyridine-2-carbonyl]amino}acetic acid or a pharmaceutically acceptable salt thereof, administered in a formulation; taking a first measurement of the hemoglobin level in the patient and subsequently taking a second measurement of the hemoglobin level in the patient, wherein if the hemoglobin level in the patient at the second measurement is less than about 9.5 to about 10.5 g/dL or about 9.75 to about 10.25 g/dL and the level of hemoglobin has increased by greater than about 1.2 to about 1.8, about 1.3 to about 1.7, or about 1.4 to about 1.6 g/dL as compared to the level at the first measurement; or if the hemoglobin level in the patient at the second measurement is between about 9.5 to about 10.5 or about 9.75 to about 10.25 g/dL and about 10.4 to about 11.4 g/dL or about 10.65 to about 11.15 g/dL and the level of hemoglobin has increased by greater than about 1.2 to about 1.8, about 1.3 to about 1.7, or about 1.4 to about 1.6 g/dL as compared to the level at the first measurement; or if the hemoglobin level in the patient at the second measurement is between about 10.5 to about 11.5 g/dL or about 10.75 to about 11.25 g/dL and about 11.7 to about 12.7 g/dL or about 11.95 to about 12.45 g/dL g/dL and the level of hemoglobin has increased by between about 0.7 to about 1.3, about 0.8 to about 1.2, or about 0.9 to about 1.1 g/dL, and about 1.1 to about 1.7, about 1.2 to about 1.6, or about 1.3 to about 1.5 g/dL as compared to the level at the first measurement; or if the hemoglobin level in the patient at the second measurement is between about 11.8 to about 12.8 g/dL or about 12.05 to about 12.55 g/dL and about 12.4 to about 13.9 g/dL or about 12.65 to about 13.15 g/dL and the level of hemoglobin has decreased by up to about 0.1 to about 0.7, about 0.2 to about 0.6, or about 0.3 to about 0.5 g/dL or increased by up to about 0.1 to about 0.7, about 0.2 to about 0.6, or about 0.3 to about 0.5 g/dL as compared to the at the first measurement; or if the hemoglobin level in the patient at the second measurement is between about about 11.8 to about 12.8 g/dL, or about 12.05 to about 12.55 g/dL and about 12.4 to about 13.9 g/dL or about 12.65 to about 13.15 g/dL g/dL and the level of hemoglobin has increased by about 0.2 to about 0.8 g/dL, about 0.3 to about 0.7 g/dL, about 0.4 to about 0.6 g/dL, about 0.6 to about 1.2 g/dL, about 0.7 to about 1.1 g/dL, or about 0.8 to 1.0 g/dL as compared to the level at the first measurement; then administering an adjusted daily dose of the compound that is less than the initial daily dose. In certain such embodiments, the adjusted daily dose of the compound is about 150 mg less than the initial daily dose. In certain embodiments, the lowest dose level is 150 mg per day. Patients already on the lowest dose level will continue on 150 mg per day unless their Hgb increases to ≥12.0 g/dL, 12.5 g/dL, or 13.0 g/dL.

In certain embodiments, the dose may be adjusted by administering to a patient having anemia an initial daily dose of a compound which is {[5-(3-chlorophenyl)-3-hydroxy-pyridine-2-carbonyl]amino}acetic acid (Compound 1) or a pharmaceutically acceptable salt thereof, administered in a formulation; taking a first measurement of the hemoglobin level in the patient and subsequently taking a second measurement of the hemoglobin level in the patient, wherein if the hemoglobin level in the patient at the second measurement is between about 10.5 to 11.5 g/dL, or about 10.75 to 11.25 g/dL and about 11.7 to 12.7 g/dL or about 11.95 to 12.45 g/dL g/dL and the level of hemoglobin has increased by greater than about 1.2 to 1.8 g/dL, about 1.3 to about 1.7 g/dL, or about 1.4 to about 1.6 g/dL as compared to the level at the first measurement; or if the hemoglobin level in the patient at the second measurement is between about 11.8 to about 12.8 g/dL or about 12.05 to about 12.55 g/dL and about 12.4 to about 13.9 g/dL or about 12.65 to about 13.15 g/dL g/dL and the level of hemoglobin has increased by between about 0.7 to about 1.3 g/dL, about 0.8 to about 1.2 g/dL, or about 0.9 to about 1.1 g/dL and about 1.1 to about 1.7 g/dL, about 1.2 to about 1.6 g/dL, or about 1.3 to about 1.5 g/dL as compared to the level at the first measurement; or if the hemoglobin level in the patient at the second measurement is between about 11.8 to about 12.8 g/dL or about 12.05 to about 12.55 g/dL and about 12.4 to about 13.9 g/dL or about 12.65 to about 13.15 g/dL and the level of hemoglobin has increased by greater than about 1.2 to about 1.8 g/dL, about 1.3 to about 1.7 g/dL, or about 1.4 to about 1.6 g/dL as compared to the level at the first measurement; then administering an adjusted daily dose of the compound that is less than the initial daily dose. In certain such embodiments, the adjusted daily dose of the compound is about 300 mg less than the initial daily dose. In certain embodiments, the lowest dose level is 150 mg per day. Patients already on the lowest dose level will continue on 150 mg per day unless their Hgb increases to 12.0 g/dL, 12.5 g/dL, or 13.0 g/dL.

In certain embodiments, the dose may be adjusted by administering to a patient having anemia an initial daily dose of a compound which is {[5-(3-chlorophenyl)-3-hydroxy-pyridine-2-carbonyl]amino}acetic acid (Compound 1) or a pharmaceutically acceptable salt thereof, administered in a formulation; taking a first measurement of the hemoglobin level in the patient and subsequently taking a second measurement of the hemoglobin level in the patient, wherein if the hemoglobin level in the patient at the second measurement is equal to or above 11.0 g/dL, 11.5 g/dL, 12.0 g/dL, 12.5 g/dL, 13.0 g/dL, 13.5 g/dL, or 14.0 g/dL, then administering an adjusted daily dose of the compound that is less than the initial daily dose. In certain such embodiments, dosing is suspended. In certain such embodiments, dosing will be suspended if Hgb rises to 11.0 g/dL, 11.5 g/dL, 12.0 g/dL, 12.5 g/dL, 13.0 g/dL, 13.5 g/dL, or 14.0 g/dL, and will not be restarted until Hgb reduces to 10.5 g/dL, 11.0 g/dL, 11.5 g/dL, 12.0 g/dL, 12.5 g/dL, 13.0 g/dL, or 13.5 g/dL. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxy-pyridine-2-carbonyl]amino}acetic acid (Compound 1) or a pharmaceutically acceptable salt thereof, administered in a formulation; taking a first measurement of the hemoglobin level in the patient and subsequently taking a second measurement of the hemoglobin level in the patient, wherein if the hemoglobin level in the patient at the second measurement is equal to or above 10.5 g/dL, 11.0 g/dL, 11.5 g/dL, 12.0 g/dL, 12.5 g/dL, 13.0 g/dL, or 13.5 g/dL, then administering an adjusted daily dose of the compound that is less than the initial daily dose. In certain such embodiments, dosing is suspended. In certain such embodiments, dosing will be suspended if Hgb rises to 10.5 g/dL, 11.0 g/dL, 11.5 g/dL, 12.0 g/dL, 12.5 g/dL, 13.0 g/dL, or 13.5 g/dL, and will not be restarted until Hgb reduces to 10.0 g/dL, 10.5 g/dL, 11.0 g/dL, 11.5 g/dL, 12.0 g/dL, 12.5 g/dL, or 13.0 g/dL. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxy-pyridine-2-carbonyl]amino}acetic acid (Compound 1) or a pharmaceutically acceptable salt thereof, administered in a formulation; taking a first measurement of the hemoglobin level in the patient and subsequently taking a second measurement of the hemoglobin level in the patient, wherein if the hemoglobin level in the patient at the second measurement is equal to or above 11.0, 11.5, 12.0, 12.5, 13.0, 13.5, or 14.0 g/dL if the patient is an adult male or 10.5 g/dL, 11.0 g/dL, 11.5 g/dL, 12.0 g/dL, 12.5 g/dL, 13.0 g/dL, or 13.5 g/dL if the patient is an adult female, then administering an adjusted daily dose of the compound that is less than the initial daily dose. In certain such embodiments, dosing is suspended. In certain such embodiments, dosing will be suspended if Hgb rises to 11.0 g/dL, 11.5 g/dL, 12.0 g/dL, 12.5 g/dL, 13.0 g/dL, 13.5 g/dL, or 14.0 g/dL if the patient is an adult male or to 10.5 g/dL, 11.0 g/dL, 11.5 g/dL, 12.0 g/dL, 12.5 g/dL, 13.0 g/dL, or 13.5 g/dL if the patient is an adult female, and will not be restarted until Hgb reduces to 10.5 g/dL, 11.0 g/dL, 11.5 g/dL, 12.0 g/dL, 12.5 g/dL, 13.0 g/dL, or 13.5 g/dL if the patient is an adult male or 10.0 g/dL, 10.5 g/dL, 11.0 g/dL, 11.5 g/dL, 12.0 g/dL, 12.5 g/dL, or 13.0 g/dL if the patient is an adult female. Factors that may temporarily change the Hgb level should be considered before suspending the dose. Hgb is assessed every 2 weeks during this time period. The dose adjustment methods described herein may be applied in treatment regimens using any compound described herein, or any combination thereof.

Dose Adjustment Based on Hemoglobin Levels

In certain embodiments, the dose may be adjusted by administering to a patient having anemia an initial daily dose of Compound 1 administered in a formulation, taking a first measurement of the hemoglobin level in the patient and subsequently taking a second measurement of the hemoglobin level in the patient, and adjusting the dose as described below. In certain embodiments, the first measurement is a baseline measurement. In certain embodiments, the dose may be adjusted by administering to a patient having anemia an initial daily dose of a compound which is Compound 1 administered in a formulation as described herein; taking a first measurement of the hemoglobin level in the patient and subsequently taking a second measurement of the hemoglobin level in the patient; and adjusting the dose as described below.

In certain embodiments, hemoglobin levels can be determined and monitored, e.g., via a HemoCue® point of care Hgb monitoring system, throughout the study to determine if the dose of study medication will be adjusted. In certain embodiments, Hgb can be obtained via HemoCue® every 2 weeks for monitoring for dose adjustment. In certain embodiments, Hgb can be obtained via HemoCue® every 4 weeks, unless more frequent monitoring is clinically indicated or warranted based on dosing changes. In certain embodiments, Hgb can be obtained via HemoCue® every 4, 6, 8, 10, 12, or 16 weeks. In certain embodiments, hemoglobin can also be assessed with a complete blood count (CBC) through the central laboratory for efficacy and safety evaluations; however, dose adjustments are based on the local HemoCue® Hgb value. In certain embodiments, the aim is to increase and maintain a Hgb level of 10-11 g/dL. In certain embodiments, the aim is to increase and maintain a Hgb level of 10-12 g/dL. In certain embodiments, the aim is to increase and maintain a Hgb level of 10-13 g/dL.

In certain embodiments, Compound 1 is dosed according to the following dose-adjustment algorithm guidelines. When adjusting therapy, Hgb rate of rise, rate of decline, and variability is considered. A single Hgb excursion may not require a dosing change.

Dose Adjustment Procedure in Patients with Chronic Kidney Disease

In certain embodiments, the dosing of a Compound 1 is adjusted during the course of treatment of a patient as described below. In certain specific embodiments, the dose is adjusted to correct anemia in a patient. In certain specific embodiments, the patient has non-dialysis dependent chronic kidney disease (NDD-CKD).

In certain embodiments, a baseline value is determined immediately prior to the first administration of Compound 1. In certain embodiments, the initial daily dose administered to the patients is 300 mg/day. In certain specific embodiments, the initial daily dose is administered in form of two tablets of 150 mg each. In certain embodiments, the initial daily dose administered to the patients is 450 mg/day. In certain specific embodiments, the initial daily dose is administered in form of three tablets of 150 mg each. In certain specific embodiments, the initial daily dose is administered in the morning. In certain specific embodiments, the initial daily dose is administered between 7 am and 2 pm.

In certain embodiments, the daily dose of Compound 1 is not increased more frequently than once every 4 weeks during the course of treatment. Decreases in daily dose can occur more frequently, but frequent dose adjustments are to be avoided.

In certain embodiments, if the Hgb has not increased by more than 0.5 g/dL above the baseline value after 4 weeks of treatment, the daily dose of the compound is increased by 150 mg/day. The daily dose is increased by 150 mg/day every 4 weeks until Hgb is above 10.0 g/dL (maximum dose is 600 mg/day). In certain specific embodiments, if the Hgb has not increased by more than 0.5 g/dL above the baseline value after 4 weeks of treatment of a NDD-CKD patient with a daily dose of Compound 1, the daily dose of the compound is increased by 150 mg/day. In certain specific embodiments, the daily dose of Compound 1 is increased by 150 mg/day every 4 weeks until Hgb in the NDD-CKD patient is above 10.0 g/dL (maximum dose is 600 mg/day).

In certain embodiments, if the Hgb rises rapidly during treatment (e.g., more than 1.0 g/dL in any 2-week period), the daily dose is reduced by 150 mg/day. In certain specific embodiments, if the Hgb in a NDD-CKD patient rises rapidly during treatment with a daily dose of Compound 1 (e.g., more than 1.0 g/dL in any 2-week period), the daily dose is reduced by 150 mg/day.

In certain embodiments, if the Hgb falls below 10.0 g/dL, the daily dose is increased by 150 mg/day. In certain specific embodiments, if the Hgb in a NDD-CKD patient falls below 10.0 g/dL during treatment with a dose of Compound 1, the daily dose is increased by 150 mg/day.

In certain embodiments, if the Hgb level exceeds 11.0 g/dL, treatment is interrupted until the Hgb decreases to 10.5 g/dL or less. Thereafter, dosing is resumed with a daily dose reduced by 150 mg/day. In certain specific embodiments, if the Hgb level in a NDD-CKD patient exceeds 11.0 g/dL, treatment with Compound 1 is interrupted until the Hgb decreases to 10.5 g/dL or less. Thereafter, dosing with Compound 1 is resumed with a daily dose reduced by 150 mg/day.

In certain embodiments, if the Hgb level exceeds 12.0 g/dL, the daily dose is reduced by 150 mg. In certain embodiments, if the Hgb level exceeds 13.0 g/dL, treatment is interrupted until the Hgb decreases to 12.5 g/dL or less. Thereafter, dosing is resumed with with a daily dose reduced by 150 mg/day. In certain specific embodiments, if the Hgb level in a NDD-CKD patient exceeds 12.0 g/dL during treatment with a daily dose of Compound 1, the dose is reduced by 150 mg/day. In certain specific embodiments, if the Hgb level in a NDD-CKD patient exceeds 13.0 g/dL, treatment with Compound 1 is interrupted until the Hgb decreases to 12.5 g/dL or less. Thereafter, dosing with Compound 1 is resumed with a daily dose reduced by 150 mg/day.

In certain embodiments, if a dose adjustment is required to maintain Hgb at the desired level, the daily dose is adjusted by 150 mg/day. In certain specific embodiments, if a dose adjustment of Compound 1 is required to maintain Hgb in a NDD-CKD patient at the desired level, the daily dose is adjusted by 150 mg/day.

In certain embodiments, the dosing of Compound 1, is adjusted during the course of treatment of a patient as described below. In certain specific embodiments, the daily dose is adjusted for the maintenance treatment of anemia in a patient. In certain specific embodiments, the patient has non-dialysis dependent chronic kidney disease (NDD-CKD).

In certain embodiments, a baseline value is determined immediately prior to the first administration of Compound 1. In certain embodiments, the initial daily dose administered to the patients is 300 mg/day. In certain specific embodiments, the initial daily dose is administered in form of two tablets of 150 mg each. In certain embodiments, the initial daily dose administered to the patients is 450 mg/day. In certain specific embodiments, the initial daily dose is administered in form of three tablets of 150 mg each. In certain specific embodiments, the initial daily dose is administered in the morning. In certain specific embodiments, the initial daily dose is administered between 7 am and 2 pm.

In certain embodiments, the daily dose of Compound 1 is not increased more frequently than once every 4 weeks during the course of treatment. Decreases in daily dose can occur more frequently, but frequent dose adjustments are to be avoided.

In certain embodiments, if dose adjustment is required to maintain Hgb at the desired level, the daily dose of the compound is adjusted by 150 mg/day (maximum daily dose is 600 mg/day). In certain specific embodiments, if dose adjustment is required to maintain Hgb at the desired level in a NDD-CKD patient, the daily dose of Compound 1 is adjusted by 150 mg/day (maximum dose is 600 mg/day).

In certain embodiments, if the Hgb falls below 10.0 g/dL, the daily dose is increased by 150 mg/day. In certain specific embodiments, if the Hgb in a NDD-CKD patient falls below 10.0 g/dL during treatment with a dose of Compound 1, the daily dose is increased by 150 mg/day.

In certain embodiments, if the Hgb level exceeds 11.0 g/dL, treatment is interrupted until the Hgb decreases to 10.5 g/dL or less. Thereafter, dosing is resumed with with a daily dose reduced by 150 mg/day. In certain specific embodiments, if the Hgb level in a NDD-CKD patient exceeds 11.0 g/dL, treatment with Compound 1 is interrupted until the Hgb decreases to 10.5 g/dL or less. Thereafter, dosing with Compound 1 is resumed with a daily dose reduced by 150 mg/day.

In certain embodiments, if the Hgb level exceeds 12.0 g/dL, the daily dose is reduced by 150 mg/day. In certain embodiments, if the Hgb level exceeds 13.0 g/dL, treatment is interrupted until the Hgb decreases to 12.5 g/dL or less. Thereafter, dosing is resumed with with a daily dose reduced by 150 mg/day. In certain specific embodiments, if the Hgb level in a NDD-CKD patient exceeds 12.0 g/dL during treatment with a daily dose of Compound 1, the daily dose is reduced by 150 mg/day. In certain specific embodiments, if the Hgb level in a NDD-CKD patient exceeds 13.0 g/dL, treatment with Compound 1 is interrupted until the Hgb decreases to 12.5 g/dL or less. Thereafter, dosing with Compound 1 is resumed with a daily dose reduced by 150 mg/day.

EXEMPLIFICATION

Example 1: Clinical Information Related to Compound 1

Mechanism of Action

Under normal oxygen concentration, prolyl hydroxylase (PHD) causes hypoxia inducible factor (HIF) a to be hydroxylated and decomposed, while PHD activity is decreased under low oxygen concentration, HIF-a protein is stabilized. As a result, gene expression including erythropoietin is increased, and erythropoiesis and iron utilization are enhanced to obtain adaptability to a hypoxic environment. Without being bound by theory, by inhibiting PHD activity, Compound 1 mimics the above-mentioned biological response, and exerts hemoglobin production and erythropoiesis by increasing erythropoietin production following stabilization of HIF-α protein.

PHD Inhibitory Action

Compound 1 inhibits human PHD1, PHD2, and PHD3 ($IC_{50}$ values: 15.36 nmol/L, 11.83 nmol/L, and 7.63 nmol/L, respectively) (in vitro).

Blood Erythropoietin Concentration Increasing Action

In a normal rat, a single oral administration of Compound 1 showed elevated blood erythropoietin levels.

Hemoglobin Concentration

In normal rats, repeated oral administration of Compound 1 for 14 days showed the effect of increasing hemoglobin concentration and red blood cell count.

Guidelines for Initiation of Administration of Compound 1

As a guideline for initiation of administration, hemoglobin concertation in hemodialysis patients is less than 10 g/dL (30% in hematocrit value), hemoglobin concentration should be less than 11 g/dL (33% hematocrit) in patients with chronic kidney disease and peritoneal dialysis patients in the storage stage.

When administering this drug, it should be confirmed that that the patient has renal anemia, and it should not be administered for other anemias, such as blood loss anemia, pancytopenia, etc.

During administration of this drug, the hemoglobin concentration or hematocrit value should be observed regularly.

Dosage Regimens

Adult patients are typically administered with an initial dose of 300 mg of Compound 1 orally, once daily.

Once an anemia-ameliorating effect is obtained, adult patients typically are administered 150 mg-600 mg of Compound 1 orally, once daily.

The dose may be adjusted appropriately according to factors including the progress and severity of anemia. The dose may also be adjusted appropriate based on, for example, the dose of a red blood cell (RBC) stimulating agent (e.g., an erythropoiesis-stimulating agent) preparation before switching. However, the maximum once daily dose of Compound 1 is 600 mg.

Increase or decrease the dose in the range of 150-600 mg daily if dose adjustment may be necessary, where no proper increase is seen in hemoglobin or hematocrit level in the early administration and/or where it is difficult to maintain hemoglobin or hematocrit level in the target range in the maintenance administration period. Dose increases or reductions are considered before the hemoglobin or hematocrit level deviate from the target values by fully monitoring changes in the level. However, the dose should not be increased by more than 150 mg increments.

Administration of an iron agent may be performed if iron deficiency is observed.

During administration of Compound 1, the hemoglobin concentration or hematocrit value are observed regularly to prevent excessive hematopoietic activity. Complications, including heart failure, ischemic heart disease, and death are associate with hemoglobin concentrations round 14 g/dL (hematocrit level 42%) compared to those with hemoglobin concentrations round 10 g/dL (hematocrit level 30%).

Pharmacokinetics of Compound 1

Blood Levels—Single Dose

Changes in plasma concentration and pharmacokinetic parameters on the first day of administration when 150 mg, 300 mg, and 600 mg of Compound 1 are repeatedly administered once a day for 10 days to healthy adult men are summarized in Table 3.

TABLE 3

| Repeated Dose Administration | | | | |
|---|---|---|---|---|
| Dose | $AUC_{0\text{-}last}$ (μg · h/mL) | $C_{max}$ (μg/mL) | $t_{max}$ (h) | $t_{1/2}$ (h) |
| 150 mg | 123 ± 30.5 | 24.2 ± 4.99 | 0.750 (0.450-3.93) | 5.96 ± 0.914 |
| 300 mg | 289 ± 75.3 | 44.3 ± 10.8 | 1.95 (1.99-4.00) | 6.14 ± 0.763 |
| 600 mg | 624 ± 205 | 84.8 ± 22.3 | 1.98 (0.98-4.00) | 6.07 ± 0.419 |

Ratio (%) of the geometric mean of $C_{max}$ and $AUC_{0\text{-}inf}$, when fasted or fed a single dose of 450 mg of this drug to healthy adult males) and its 90% confidence intervals were 73% [68%, 79%] and 94% [90%, 98%]. The median $t_{max}$ of this drug was prolonged by postprandial administration for about 1.5 hours as compared with fasting. These results are summarized in Table 4.

TABLE 4

| Influences of Meal | | | |
|---|---|---|---|
| Dose | $C_{max}$ (μg/mL) | $AUC_{0-inf}$ (μg · h/mL) | $t_{max}$ (h) |
| Fasting | 63.1 ± 14.58 | 371 ± 100.0 | 2.00 (0.97-6.00) |
| After Meal | 46.3 ± 12.17 | 351 ± 101.3 | 3.52 (1.03-8.97) |

Distribution

The human plasma protein binding rate of this drug was higher than 99% (in vitro, equilibrium dialysis).

Metabolism

Compound 1 is metabolized via UGT, mainly producing 0-glucuronide conjugates. When Compound 1 was orally administered to a healthy adult male (6 patients) once with 650 mg of [$^{14}$C]-labeled, Compound 1 accounts for 75% of the total radioactivity ($AUC_{0-\infty}$) in plasma, whereas the 0-glucuronide conjugate was about 15%.

UGT1A1, UGT1A7, UGT1A8 and UGT1A9 were involved in the generation of 0-glucuronide, which is the main metabolite of this drug in humans (in vitro). Although Compound 1 showed an inhibitory effect on CYP2B6, CYP2C8, CYP2C9, and UGT1A1 (in vitro), the variation ratio of AUC of each typical substrate was less than 1.25 times (static) Pharmacokinetics model).

Excretion

When a single dose of 650 mg of [$^{14}$C]-labeled Compound 1 was administered to healthy adult males (6 cases), 58.9% of the total radioactivity administered is in urine and 26 9% in feces by 72 hours after administration. The urinary excretion rate of this drug and acyl glucuronide is less than 1% of the total radioactivity. Without being bound by theory, the main excretion route of this Compound 1 is urinary excretion of 0-glucuronide conjugate via glucuronidation.

Phase III Clinical Trial of Compound 1 with Patients Having Hemodialysis Anemia

Compound 1 was administered for 24 weeks to patients with hemodialysis anemia who did not use erythrocyte stimulating factor (the dose of Compound 1 was 300 mg once daily as the initial dose and 150 mg to 600 mg once daily as the maintenance dose). Average hemoglobin levels at 20 and 24 weeks are shown in Table 5. The incidence of adverse reactions when this drug was administered up to 24 weeks was 8.3% (2/24 cases).

TABLE 5

| Phase III Clinical Trial of Compound 1 | | |
|---|---|---|
| | Before administration | After administration |
| Main agent group (23 people) | 9.30 ± 0.67 | 10.75 ± 0.19 [10.35, 11.14] |

Before administration: mem ± standard deviation, After administration: adjusted average value + standard error

[ ] 95% confidence interval of both sides

Example 2: Administration of Sevelamer Carbonate with Compound 1

Investigators can prescribe a composition comprising a polymeric amine that binds to phosphate as needed to a patient taking Compound 1.

A phase I, open-label, fixed-sequence study was conducted in healthy adult subjects to assess the effect of sevelamer carbonate as phosphate binders on the pharmacokinetics of a single dose of vadadustat.

The study included screening (28 days maximum), 9-day treatment period, and a 14-day follow-up period post last dose.

Following the screening period, subjects who meet all inclusion and no exclusion criteria described below were randomized in the subsequent treatment period. A total of 18 subjects were enrolled in the study.

Inclusion Criteria:

1. Male or female between 18 and 55 years of age, inclusive, at time of informed consent.
   a. Female subjects of childbearing potential must be non-lactating, not pregnant as confirmed by a negative serum pregnancy test at screening and Day −1, and using, and agree to continue using, an effective method of contraception for at least of 4 weeks prior to the first dose of study drug until 30 days after the last dose of study drug.
   b. Female subjects of non-childbearing potential must be surgically sterile (e.g., hysterectomy, bilateral tubal ligation, oophorectomy) or post-menopausal (no menses for >1 year with follicle stimulating hormone [FSH]>40 U/L at screening).
   c. Female subjects of childbearing potential must agree not to donate ova during the study and for at least 30 days after the last dose of study drug.
   d. Male subjects who have not had a vasectomy for at least 6 months must agree to use an effective method of contraception during the study and until 90 days after the last dose of the study drug, and to not donate sperm during the study and for at least 90 days after the last dose of study drug.
2. Healthy per investigator judgment as documented by medical history, physical examination, vital sign assessments, 12-lead ECG, clinical laboratory assessments, and general observations.
   a. At screening, abnormalities or deviations outside the normal ranges for any clinical assessments (laboratory tests, ECG, vital signs) may be repeated once at the discretion of the investigator(s), and results that continue to be outside the normal ranges must be judged by the investigator to be not clinically significant and acceptable for study participation.
   b. On Day −1, alanine aminotransferase (ALT), aspartate aminotransferase (AST) and total bilirubin values must be within the upper limits of the normal range. All other laboratory test results that are outside the normal range on Day −1 and judged by the investigator to be not clinically significant may be repeated. Results that continue to be outside the normal range must be judged by the investigator to be not clinically significant and acceptable for study participation.
3. Body mass index (BMI) between 18.0 and 30 kg/m2, with a minimum body weight of 45 kg for females and 50 kg for males, inclusive.
4. Understands the procedures and requirements of the study and provides written informed consent and authorization for protected health information disclosure
5. Willing and able to comply with the requirements of the study protocol.

Exclusion Criteria

1. Current or past history of cardiovascular, cerebrovascular, respiratory, gastrointestinal, hematologic, renal, hepatic, immunologic, metabolic, urologic, neurologic, dermatologic, psychiatric, or other major disease, as determined by the investigator. History of cancer (except treated non-melanoma skin cancer) or history of chemotherapy use within 5 years prior to screening.

2. Any surgical or medical condition or history that, in the opinion of the investigator, may potentially alter the absorption, metabolism, or excretion of study treatment, such as, but not limited to gastric bypass surgery or gastric or duodenal ulcers.
3. Clinically significant history of dysphagia, bowel obstruction, or perforation.
4. Clinically significant history of hypercalcemia.
5. Clinically significant history of iron overload.
6. Clinically significant history of liver disease.
7. Clinically significant history of hypophosphatemia, ulcerative colitis, or gastrointestinal bleeding.
8. Contraindication to study drugs or its excipients and/or history of allergic or anaphylactic reactions.
9. Taking any of the following prohibited medications:
   a. Any prescription medication or over the counter multi-vitamin supplement, or any nonprescription products (including herbal-containing preparations but excluding acetaminophen up to 2 g daily) within 14 days prior to Day −1, b. Any drug known to inhibit or induce cytochrome P450 (CYP) enzymes and/or P-glycoprotein including St. John's wort (*Hypericum perforatum*) within 14 days or 5 half-lives (whichever is longer) prior to Day −1.
10. History of drug abuse within the previous year prior to screening or use of soft drugs (such as marijuana) within 3 months prior to the screening visit or hard drugs (such as cocaine, phencyclidine [PCP], crack, opioid derivatives including heroin, and amphetamine derivatives) within 1 year prior to screening.
11. History of regular alcohol consumption exceeding 14 drinks/week (1 drink=5 ounces [150 mL] of wine or 12 ounces [360 mL] of beer or 1.5 ounces [45 mL] of hard liquor) within 6 months of screening or alcohol abuse within 1 year prior to screening.
12. Positive drug and alcohol test at screening or on Day −1.
13. History of latent or active tuberculosis (TB) as per documented medical history. Exposure to endemic areas within 8 weeks of screening.
14. Daily use of nicotine-containing products within 6 months of screening.
15. Consumed any food or drink/beverage containing grapefruit or grapefruit juice, apple or orange juice, pomelo juice, pomegranate, pineapple, star fruit, Seville or Moro (blood) orange products, and vegetables from the mustard green family (e.g., kale, broccoli, watercress, collard greens, kohlrabi, brussels sprouts, mustard) and charbroiled meats known to modulate CYP enzyme activity and transporters within 7 days before administration of study drug.
16. Positive test results of hepatitis B surface antigen (HBsAg), or positive hepatitis C virus antibody (HCVab) test result within 3 months prior to Day −1 or at screening.
17. Positive test results for human immunodeficiency virus (HIV) antibody within 3 months prior to Day −1 or at screening.
18. Participation in another clinical trial or exposure to any investigational agent within 30 days or 5 half-lives prior to Day −1, whichever is longer.
19. Donation of plasma within 7 days prior to dosing. Donation or loss of blood (excluding volume drawn at screening) of 50 mL to 499 mL of blood within 30 days, or more than 499 mL within 56 days prior to the first dosing.
20. Received a tattoo or body piercing (including ear piercings) within 2 months prior to Day 1, and/or open wound that may result in risk of infection.
21. Having a condition that the investigator believes would interfere with his/her ability to provide written informed consent, comply with study instructions, or which might confound the interpretation of the study results or put the subject at undue risk.
22. Have previously participated in a clinical study that administered vadadustat.

Criteria for Evaluation

Pharmacokinetics. A predose PK blood sample was collected on Day 1. After each dose of vadadustat administered (Days 1, 3, 5, and 7), blood samples for PK analysis were collected at the following time points: predose and 0.5, 1, 1.5, 2, 3, 4, 6, 9, 12, 16, 24, and 48 hours after each dose of vadadustat. The 48-hour postdose sample was collected before vadadustat administration on Days 3, 5, and 7. The following parameters were calculated and analyzed: $AUC_{0-\infty}$, $AUC_{0-last}$, $C_{max}$, $T_{max}$, Kel, $CI_B$, $V_c/F$, and $t_{1/2}$.

Safety. Safety and tolerability were evaluated by adverse event reporting, assessment of 12-lead electrocardiograms (ECGs), vital signs, physical examination and clinical laboratory tests.

Treatment of Subjects

Subjects were dosed approximately at the same designated time on each dosing day, where applicable. Study drugs were administered with approximately 8 ounces (240 mL) of water at room temperature in a seated position. Subjects were instructed to drink the full 8 ounces of water, and not to chew or break the tablets/gelcaps.

A single oral dose of vadadustat 300 mg (2×150 mg tablets) was administered on Days 1, 3, 5, and 7. Phosphate binder that is sevelamer carbonate (1600 mg, 2×800 mg tablets) was administered on Days 3, 5, and 7.

The 9-day treatment period was conducted as follows:

Day 1: vadadustat administered immediately after consuming breakfast.

Day 2: wash-out (no investigational product administration).

Day 3: vadadustat administered concomitantly with the requisite phosphate binder immediately after consuming breakfast.

Day 4: wash-out (no investigational product administration).

Day 5: vadadustat administered in fasted condition and the phosphate binder administered 1 hour later (breakfast must be served within 2 minutes after phosphate binder administration and consumed immediately after it is served).

Day 6: wash-out (no investigational product administration).

Day 7: phosphate binder administered immediately after consuming breakfast; vadadustat administered 2 hours after the phosphate binder was administered.

Day 8: wash-out (no investigational product administration).

Day 9: subjects discharged from the Clinical Research Unit (CRU) after the 48-hour postdose PK blood sample has been collected.

Data Analysis

Vadadustat plasma PK parameter findings are summarized in Table 6. Plasma concentration-time profiles for vadadustat alone and when coadministered with sevelamer carbonate are presented in FIG. 1.

TABLE 6

Summary of plasma PK parameters for vadadustat following coadministration with sevelamer carbonate

| PK parameters | Vadadustat alone[a] (n = 18) | Sevelamer carbonate + vadadustat: Concomitant administration[b] (n = 18) | Vadadustat administered 1 hour prior to sevelamer carbonate[c] (n = 18) | Vadadustat administered 2 hours after sevelamer carbonate[d] (n = 18) |
|---|---|---|---|---|
| $AUC_{0\text{-}last}$ (μg · h/mL) | 185 ± 57.3 | 121 ± 50.4 | 152 ± 46.2 | 151 ± 57.5 |
| $AUC_{0\text{-}\infty}$ (μg · h/mL) | 190 ± 57.2 | 124 ± 51.0 | 156 ± 48.5 | 154 ± 57.8 |
| $C_{max}$ (μg/mL) | 26.7 ± 6.61 | 16.6 ± 5.75 | 31.3 ± 10.65 | 24.6 ± 7.60 |
| $T_{max}$ (h) | 3.97 (2.93, 5.96) | 3.49 (2.01, 6.08) | 1.49 (0.92, 6.00) | 2.99 (0.94, 5.93) |
| Elimination half-life ($t_{1/2}$; h) | 4.81 ± 1.15 | 4.70 ± 0.90 | 4.47 ± 0.72 | 5.10 ± 0.97 |
| Clearance ($Cl_B$; L/h) | 1.73 ± 0.55 | 2.88 ± 1.35 | 2.14 ± 0.82 | 2.30 ± 1.07 |
| Volume of distribution ($V_c$; L) | 11.5 ± 2.84 | 19.4 ± 10.09 | 13.6 ± 5.04 | 16.4 ± 7.04 |

[a]Vadadustat 300 mg administered immediately after breakfast.
[b]Vadadustat 300 mg administered concomitantly with sevelamer carbonate immediately after breakfast.
[c]Vadadustat 300 mg administered under fasting conditions and sevelamer carbonate administered 1 hour later, followed immediately (within 2 minutes) by breakfast.
[d]Sevelamer carbonate followed immediately by breakfast; vadadustat 300 mg administered 2 hours later.
Values are represented as mean ± SD, expect for $T_{max}$, presented as median (minimum, maximum).
$AUC_{0\text{-}\infty}$, area under the plasma concentration-time curve from dosing (time 0) to infinity;
$AUC_{0\text{-}last}$, area under the plasma concentration-time curve from dosing (time 0) to last quantifiable concentration;
$C_{max}$, maximum observed plasma concentration;
PK, pharmacokinetics;
SD, standard deviation;
$T_{max}$, time to maximum observed plasma concentration;
$V_c$, apparent volume of central component of pharmacokinetic model.

Figure 2:
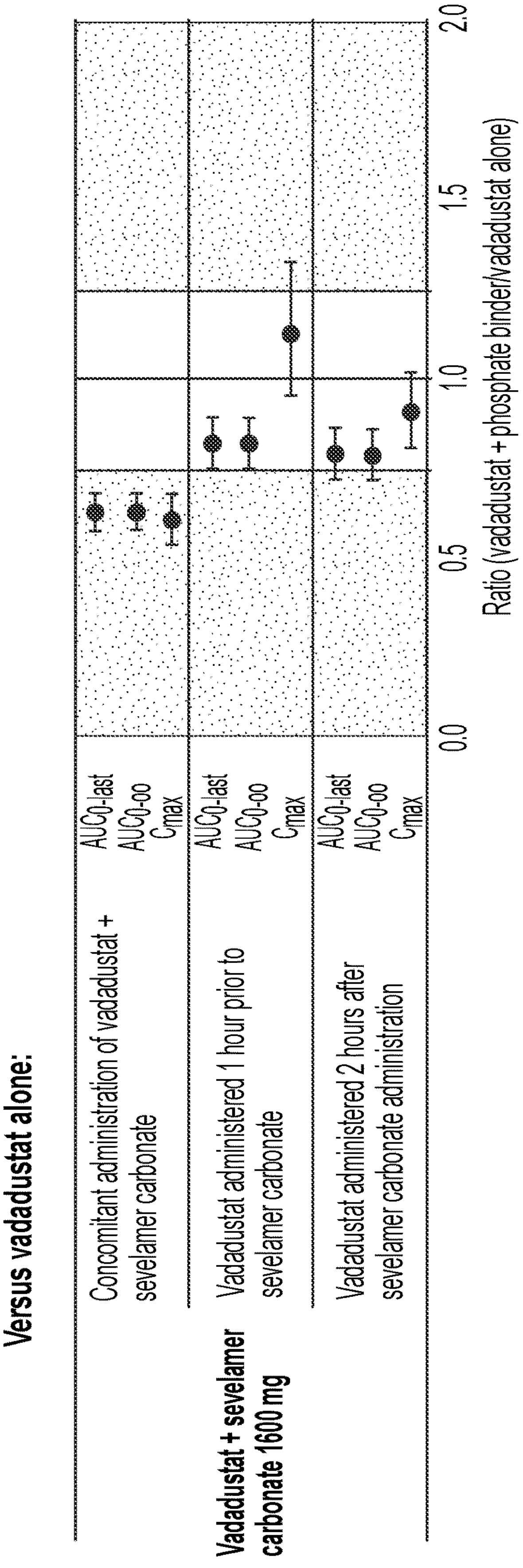
FIG. 2 shows effect of a single dose of phosphate binder that is sevelamer carbonate on the PK of vadadustat (300 mg). Values shown are geometric least squares mean ratios; the error bars represent the 90% geometric confidence interval. $AUC_{0-\infty}$: area under the plasma concentration-time curve from time 0 to infinity; $AUC_{0\text{-}last}$: area under the plasma concentration-time curve from time 0 to last quantifiable concentration; $C_{max}$: maximum observed plasma concentration; PK: pharmacokinetics.

Concomitant administration of sevelamer carbonate with vadadustat reduced vadadustat $AUC_{0\text{-}last}$, $AUC_{0\text{-}\infty}$ and $C_{max}$ compared with administering vadadustat alone, whereas $T_{max}$ and $t_{1/2}$ remained similar and $CI_B$ and $V_c$ increased (Table 6 and FIG. 1). ANOVA (Analysis of variance) indicated that concomitant administration of phosphate binders with vadadustat reduced vadadustat $AUC_{0\text{-}last}$ and $AUC_{0\text{-}\infty}$ by about 37% and $C_{max}$ by about 40% (FIG. 2). Specifically, the geometric LS mean $AUC_{0\text{-}\infty}$ for concurrent vadadustat and sevelamer carbonate was 113.98 μg·h/mL, with a geometric LS mean ratio of 62.85% (90% CI, 57.96-68.16) to vadadustat alone. However, when vadadustat was administered 1 hour prior to or 2 hours after sevelamer carbonate, changes in vadadustat exposure were within the prespecified no-effect boundaries of 80% to 125%. This suggests that the DDI with phosphate binders such as sevelamer carbonate can be overcome by administering vadadustat immediately upon waking, prior to breakfast, or 2 hours after administering a phosphate binder (which can continue to be administered with meals).

Example 3: Administration of an Organic Anion Transporter with Compound 1

Investigators can prescribe a composition comprising an organic anion transporter (e.g., an OAT1/OAT3 and/or OATP1B1 inhibitor) as needed to a patient taking Compound 1.

A phase I, open-label, 2-part study was conducted in healthy male and female subjects to evaluate the potential for interaction of cyclosporine (Part 1, Arm 1), probenecid (Part 1, Arm 2), and rifampin (Part 2) with vadadustat.

The study included a 28-day Screening period, a 6- to 10-day clinic period, and a 30-day (±2 days) follow-up period post last dose.

Following the screening period, subjects who meet all inclusion and no exclusion criteria described below were randomized in the subsequent clinic period.

Inclusion Criteria:

Subjects were to have met the following inclusion criteria to participate in the study:

1. Male or female between 18 and 55 years of age, inclusive, at time of informed consent.
    a. Female subjects of childbearing potential must be non-lactating, not pregnant as confirmed by a negative serum pregnancy test at Screening and Day −1, and using, and agree to continue using, an effective method of contraception for at least 4 weeks prior to first study drug administration until 30 days after the last dose of study drug.
    b. Female subjects of non-childbearing potential must be surgically sterile (e.g., hysterectomy, bilateral tubal ligation, oophorectomy) or post-menopausal (no menses for >1 year with follicle-stimulating hormone [FSH]>40 U/L at Screening)
    c. Female subjects of childbearing potential must not donate ova during the study and for at least 30 days after the last dose of study drug.
    d. Male subjects who have not had a vasectomy must agree to use an effective method of contraception for at least 4 weeks prior to first study drug administration until 90 days after the last dose of the study drug, and to not donate sperm during the study and for at least 90 days after the last dose of study drug.

2. Healthy per Investigator judgment as documented by medical history, physical examination, vital sign assessments, 12-lead ECG, clinical laboratory assessments, and general observations.
   a. At Screening, abnormalities or deviations outside the normal ranges for any clinical assessments (laboratory tests, ECG, vital signs) may be repeated once at the discretion of the Investigator(s), and results that continue to be outside the normal ranges must be judged by the Investigator to be not clinically significant and acceptable for study participation.
   b. On Day −1, alanine aminotransferase (ALT), aspartate aminotransferase (AST) and total bilirubin values must be within the upper limits of the normal range. All other laboratory test results that are outside the normal range on Day −1 and judged by the Investigator to be not clinically significant may be repeated. Results that continue to be outside the normal range must be judged by the Investigator to be not clinically significant and acceptable for study participation.
3. Body mass index between 18.0 and 30.0 kg/$m^2$, with a minimum body weight of 45 kg for females and 50 kg for males, inclusive.
4. Understands the procedures and requirements of the study and provides written informed consent and authorization for protected health information disclosure.
5. Willing and able to comply with the requirements of the study protocol.

Exclusion Criteria:

Subjects who presented with any of the following were not to be entered into the study:

1. Current or past clinically significant history of cardiovascular, cerebrovascular, pulmonary, gastrointestinal, hematologic, renal, hepatic, immunologic, metabolic, urologic, neurologic, dermatologic, psychiatric, or other major disease, as determined by the Investigator. History of cancer (except treated non-melanoma skin cancer) or history of chemotherapy use within 5 years prior to Screening.
2. Any surgical or medical condition or history that, in the opinion of the Investigator, may potentially alter the absorption, metabolism, or excretion of study treatment, such as, but not limited to gastric bypass surgery or gastric or duodenal ulcers.
3. Contraindication to study drugs or its excipients and/or history of allergic or anaphylactic reactions.
4. Taking any of the following prohibited medications:
   a. Any prescription medication or over the counter multi-vitamin supplement, or any nonprescription products (including herbal-containing preparations but excluding acetaminophen) within 14 days prior to Day −1.
   b. Any drug known to inhibit or induce cytochrome P450 (CYP) enzymes and/or P-glycoprotein including St. John's wort (*Hypericum perforatum*) within 14 days or 5 half-lives (whichever is longer) prior to Day −1.
5. History of drug abuse within the previous year prior to Screening.
6. History of regular alcohol consumption exceeding 14 drinks/week [1 drink: 5 ounces (150 mL) of wine or 12 ounces (360 mL) of beer or 1.5 ounces (45 mL) of hard liquor] within 6 months of Screening.
7. Positive drug and alcohol test at Screening or on Day −1.
8. History of latent or active tuberculosis (TB) as per documented medical history. Exposure to endemic areas within 8 weeks of Screening.
9. Positive QuantiFERON®-TB test indicating possible TB infection at Screening (unless documented results of a test performed within 2 months).
10. Currently smoke 10 cigarettes or more per day.
11. Consumed any food or drink/beverage containing of grapefruit or grapefruit juice, apple or orange juice, pomelo juice, star fruit, Seville or Moro (blood) orange products, and vegetables from the mustard green family (e.g., kale, broccoli, watercress, collard greens, kohlrabi, brussel sprouts, mustard), food containing poppy seeds (e.g., muffins, bagels and cakes) 24 hours before Day −1, and charbroiled meats known to modulate CYP enzyme activity and transporters within 6 days before Day −1.
12. Positive test results of hepatitis B surface antigen (HBsAg), or positive hepatitis C virus antibody (HCVab) test result at Screening.
13. Positive test results for human immunodeficiency virus antibody (HIVab) at Screening.
14. Participation in another clinical trial or exposure to any investigational agent within 30 days or 5 half-lives prior to Day −1, whichever is longer.
15. Donation or loss of blood (excluding volume drawn at Screening) within 60 days or plasma donation within 7 days prior to the first dose.
16. Received a tattoo or body piercing (including ear piercings) within 2 months prior to Day 1, and/or open wound that may result in risk of infection.
17. Having a condition that the Investigator believes would interfere with his/her ability to provide written informed consent, comply with study instructions, or which might confound the interpretation of the study results or put the subject at undue risk.

Treatment of Subjects.

Part 1 (Cyclosporine and Probenecid)

Arm 1—Cyclosporine

Subjects were randomized in a 1:1 ratio to 1 of 2 dosing sequences (A:B or B:A) to receive vadadustat 300 mg alone and vadadustat 300 mg in combination with oral cyclosporine 500 mg in a crossover design. Study drugs were administered in the morning after at least a 10-hour overnight fast. Subjects remained fasted for at least 4 hours post-dose.

Treatment A: a single oral dose of vadadustat (300 mg) administered as 2×150 mg tablets.

Treatment B: a single oral dose of vadadustat (300 mg) administered as 2×150 mg tablets co-administered with a single oral dose of cyclosporine (500 mg) administered as 5×100 mg capsules.

On the morning of Day 1, subjects received the first treatment (A or B). Following a 7-day washout, subjects crossed over to Period 2 to receive the second treatment of the dosing sequence (A or B) on Day 8.

On each dosing day (Day 1 and Day 8) blood samples for PK analysis were collected up to 48 hours post-dose. Subjects were discharged from the clinical research unit (CRU) on the morning of Day 10, after the final 48-hour post-dose PK sample had been collected. A follow-up phone call was conducted 30 days±2 days after the final dose.

Part 1 Arm 2 (probenecid):

On the morning of Day 1, subjects received a single oral dose of vadadustat (300 mg) as 2×150 mg tablets after at least a 10-hour overnight fast and remained fasted for at least 4 hours post-dose. Following a 2-day washout (Days 1 to 2), subjects received 1 oral probenecid 500 mg tablet Q12 h for 4 days (Days 3 to 6). On days that probenecid was administered alone (Days 3, 4, and 6), probenecid was administered in a fasted state 1 hour prior to a standard breakfast and 1 hour prior to an evening meal or snack. On Day 5, probenecid was co-administered with a single dose of vadadustat (300 mg as 2×150 mg tablets) following at least a 10-hour fast. Subjects remained fasted for at least 4 hours after dosing.

On days vadadustat was administered (Day 1 and Day 5), blood samples for PK analysis were collected up to 48 hours postdose. In addition, on vadadustat dosing days, pooled urine samples were collected up to 24 hours post-dose. Subjects were discharged from the CRU on the morning of Day 7, after the final 48-hour post-dose PK sample had been collected. A follow-up phone call was conducted 30 days±2 days after the final dose.

Part 2—Rifampin

The following study design was to be conducted only if a DDI between vadadustat and cyclosporine was observed.

Subjects were randomized in a 1:1 ratio to 1 of 2 dosing sequences (A:B or B:A) to receive vadadustat 300 mg alone and vadadustat 300 mg in combination with rifampin 600 mg IV in a crossover design. Study drugs were administered in the morning after at least a 10-hour overnight fast. Subjects remained fasted for at least 4 hours post dose.

- Treatment A: a single oral dose of vadadustat (300 mg) administered as 2×150 mg tablets.
- Treatment B: a single 30-minute IV infusion of rifampin (600 mg) followed immediately (within 5 minutes) by a single oral dose of vadadustat (300 mg as 2×150 mg tablets).

Rifampin 600 mg IV was administered over 30 minutes as described in the Product Monograph. On the morning of Day 1, subjects received the first treatment (A or B). Following a 7-day washout, subjects crossed over to Period 2 to receive the second treatment of the dosing sequence (A or B) on Day 8.

On each dosing day (Day 1 and Day 8), blood samples for PK analysis were collected up to 48 hours post-dose. Subjects were discharged from the CRU on the morning of Day 10 after the final 48-hour post-dose PK sample had been collected. A follow-up phone call was conducted 30 days±2 days after the final dose.

Data Analysis

Figure 3A:
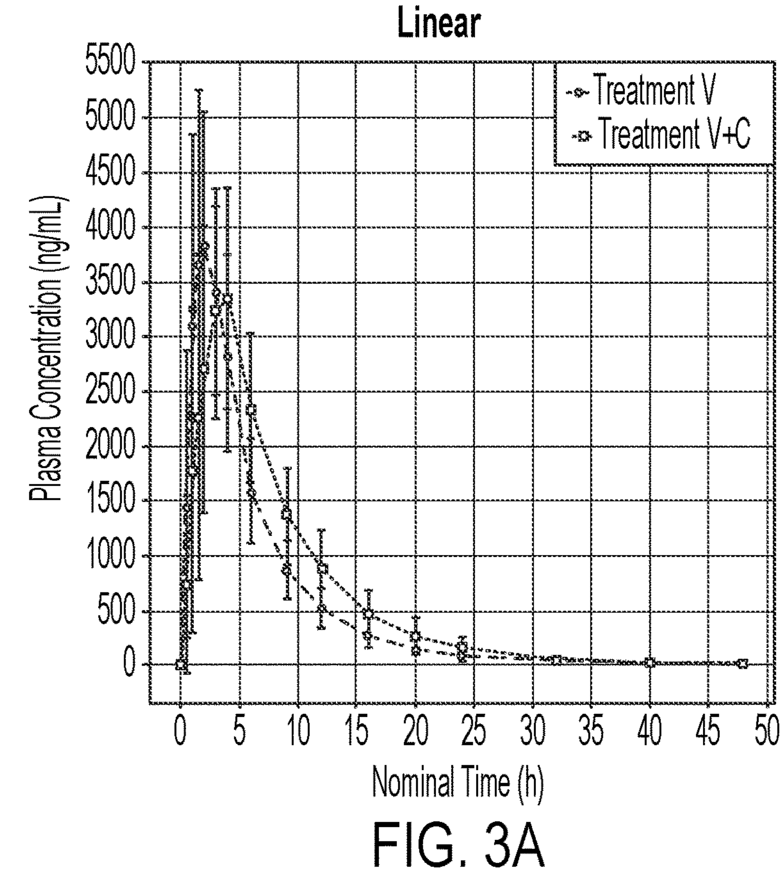
FIGS. 3*a*-3*b* show mean (SD) vadadustat plasma concentration (Days 1 and 5) (ng/mL) versus time (Pharmacokinetic Population) when 1) 300 mg vadadustat administered alone; and 2) 300 mg vadadustat administered with 500 mg cyclosporine.
Figure 3B:
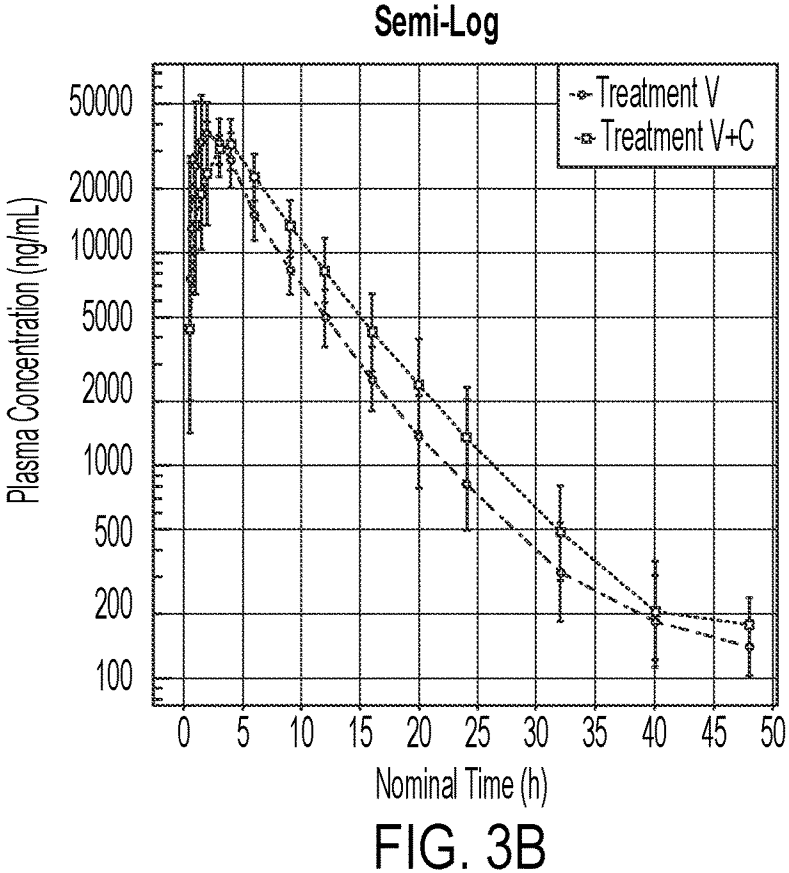
Figure 4A:
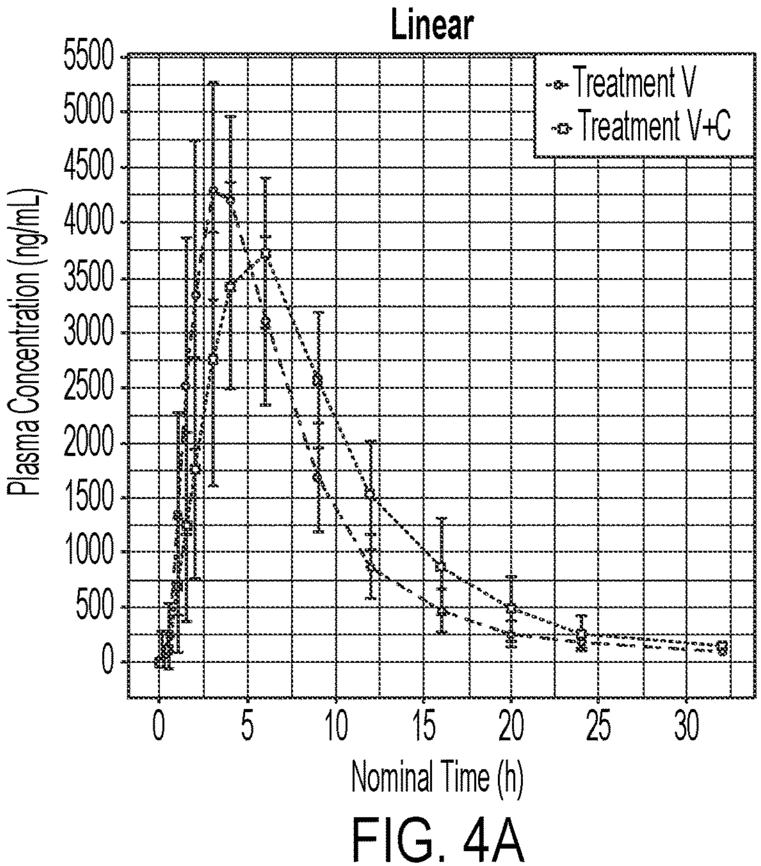
FIGS. 4*a*-4*b* show mean (SD) vadadustat-O-glucuronide plasma concentration (days 1 and 5) (ng/mL) versus time (Pharmacokinetic Population) when 1) 300 mg vadadustat administered alone; and 2) 300 mg vadadustat administered with 500 mg cyclosporine.
Figure 4B:
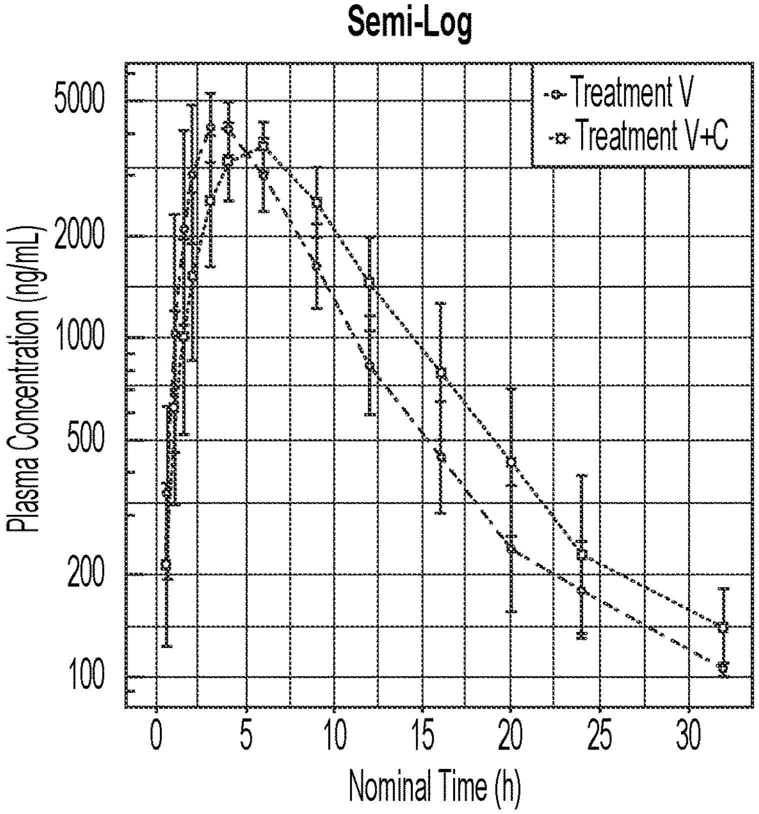

Plasma concentration-time profiles for vadadustat alone and when coadministered with cyclosporine are presented in Figures. 3-4.

Following treatment with vadadustat alone or vadadustat plus cyclosporine, point estimates of the T/R mean ratios of the primary parameters $AUC_{last}$, $AUC_{inf}$, and $C_{max}$ for vadadustat were 116.97%, 116.89%, and 81.76%, respectively. For vadadustat-O-glucuronide, T/R mean ratios of the primary parameters $AUC_{last}$, $AUC_{inf}$, and $C_{max}$ were 114.04%, 113.74%, and 86.63%, respectively. Overall, these data indicated no-to-minimal interaction between vadadustat and cyclosporine (Table 7).

TABLE 7

Summary of plasma PK parameters for vadadustat following coadministration with Cyclosporine

| Parameter (unit) | Geometric LSM Treatment V + C | Geometric LSM Treatment V | Ratio (V + C)/V[1] (%) | 90% Geometric CI[2] Lower (%) | 90% Geometric CI[2] Upper (%) | Intra-Subject CV (%)[3] | Inter-Subject CV (%)[4] |
|---|---|---|---|---|---|---|---|
| Vadadustat | | | | | | | |
| $AUC_{last}$ (hr*μg/mL) | 291.77 | 249.44 | 116.97 | 109.35 | 125.13 | 12.34 | 22.81 |
| $AUC_{inf}$ (hr*μg/mL) | 293.23 | 250.86 | 116.89 | 109.32 | 124.99 | 12.26 | 22.75 |
| $C_{max}$ (μg/mL) | 37.13 | 45.42 | 81.76 | 76.02 | 87.93 | 13.34 | 22.74 |
| Vadadustat-O-Glucuronide | | | | | | | |
| $AUC_{last}$ (hr*μg/mL) | 38.13 | 33.43 | 114.04 | 108.84 | 119.50 | 8.54 | 23.24 |
| $AUC_{inf}$ (hr*μg/mL) | 39.21 | 34.48 | 113.74 | 108.57 | 119.16 | 8.50 | 22.73 |
| $C_{max}$ (μg/mL) | 3.90 | 4.50 | 86.63 | 82.25 | 91.26 | 9.50 | 17.27 |

$AUC_{inf}$: AUC from 0 to infinity;
$AUC_{last}$: AUC from 0 to last quantifiable concentration;
$C_{max}$: maximum observed plasma concentration;
CV %: coefficient of variation;
V: vadadustat;
V + C: vadadustat and cyclosporine
[1]90% Geometric Confidence Interval calculated according to the formula: exp(DIFFERENCE ± t(dfResidual) * SEDIFFERENCE) * 100.
[2]Calculated using least-square means according to the formula: exp(DIFFERENCE) * 100.
[3]Calculated according to formula: SQRT (exp (MSE) − 1) * 100.
[4]Calculated according to formula: SQRT (exp ((MSSUBJECT(SEQ) − MSE)/2) − 1) * 100.
Probability (p) values were derived from Type III sums of squares. P-value for the Sequence effect was tested using the Subject(Sequence) effect as the error term.

Figure 5A:
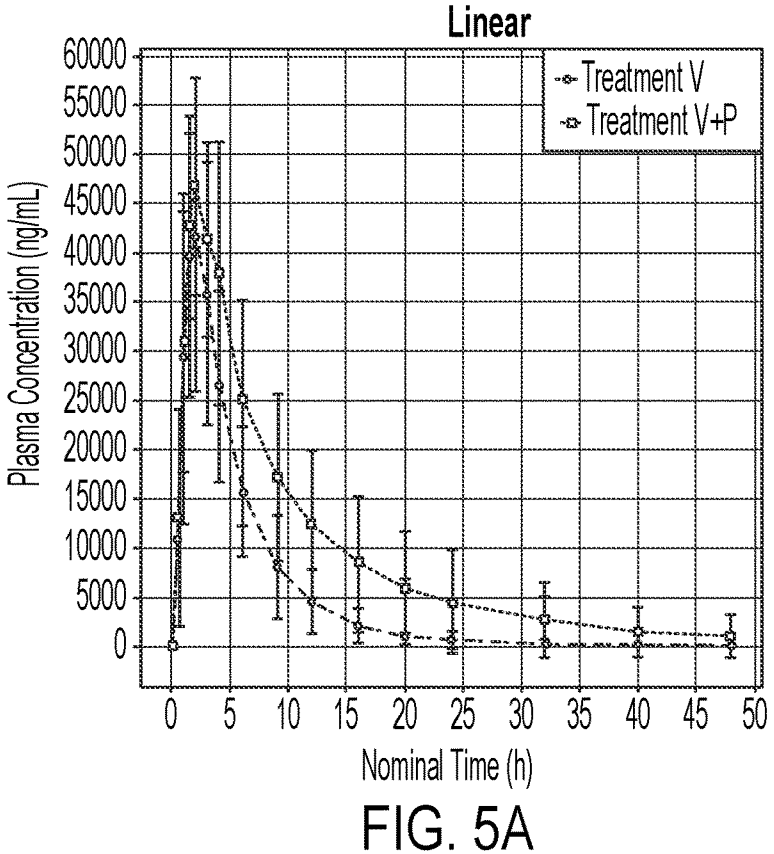
FIGS. 5*a*-5*b* show mean (SD) vadadustat plasma concentration (days 1 and 8) (μg/ml) versus time (Pharmacokinetic Population) when 1) 300 mg vadadustat administered alone; and 2) 300 mg vadadustat administered with 500 mg probenecid.
Figure 5B:
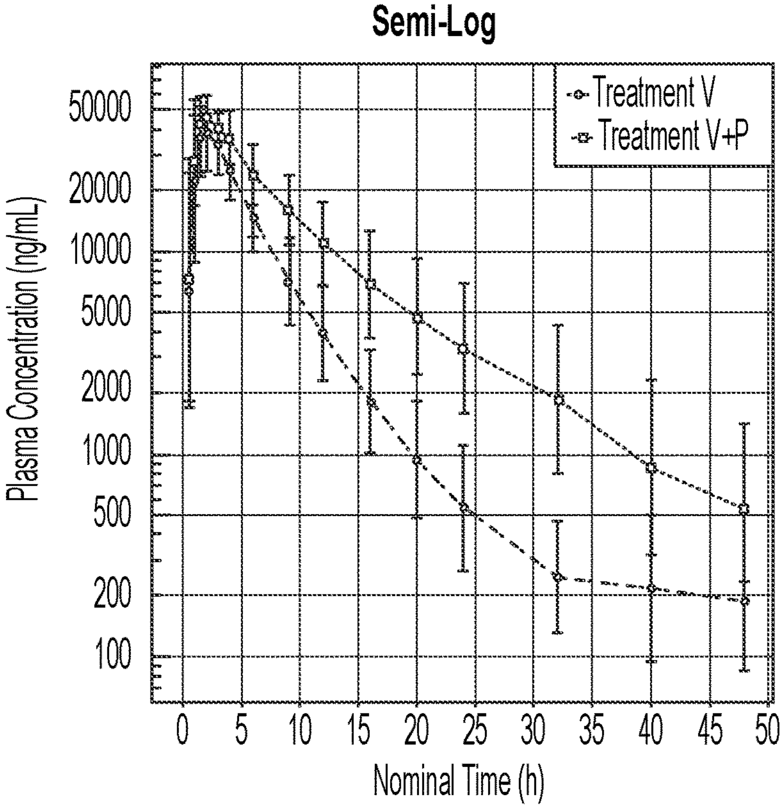
Figure 6A:
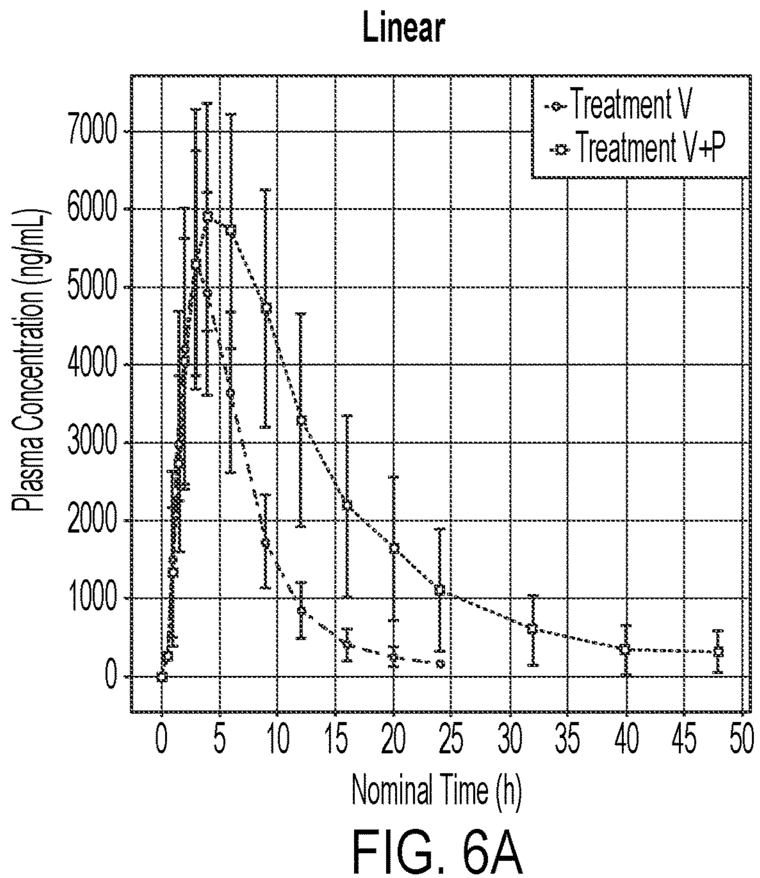
FIGS. 6*a*-6*b* show mean (SD) vadadustat-O-glucuronide plasma concentration (days 1 and 8) (μg/ml) versus time (Pharmacokinetic Population) when 1) 300 mg vadadustat administered alone; and 2) 300 mg vadadustat administered with 500 mg probenecid.
Figure 6B:
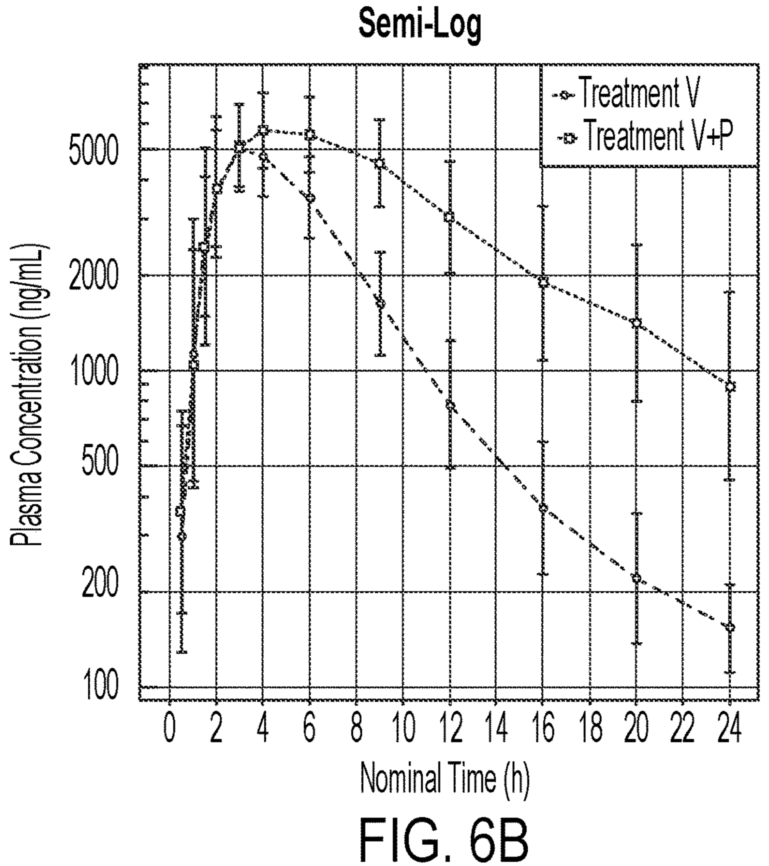

Plasma concentration-time profiles for vadadustat alone and when coadministered with probenecid are presented in Figures. 5-6.

Following treatment with vadadustat alone or vadadustat plus probenecid, point estimates of the T/R mean ratios of the primary parameters $AUC_{last}$, $AUC_{inf}$, and $C_{max}$ for vadadustat were 178.95%, 182.13%, and 102.79%, respectively. These data indicate just under a 2-fold increase in exposure to vadadustat when it was administered with multiple doses of probenecid. For vadadustat-Oglucuronide, T/R mean ratios were 224.05%, 226.39%, 110.38%, respectively (Table 8). These data also showed an ~2-fold increase when administered with multiple doses of probenecid.

TABLE 8

| Summary of plasma PK parameters for vadadustat following coadministration with Probenecid | | | | | | |
|---|---|---|---|---|---|---|
| | Geometric LSM | | Ratio | | | Intra- |
| | Treatment | Treatment | (V + P)/V[1] | 90% Geometric CI[2] | | Subject |
| Parameter (unit) | V + P | V | (%) | Lower (%) | Upper (%) | CV (%)[3] |
| Vadadustat | | | | | | |
| $AUC_{last}$ (hr*μg/mL) | 416.58 | 232.80 | 178.95 | 169.98 | 188.38 | 8.88 |
| $AUC_{inf}$ (hr*μg/mL) | 426.59 | 234.22 | 182.13 | 171.08 | 193.89 | 10.83 |
| $C_{max}$ (μg/mL) | 48.78 | 47.46 | 102.79 | 94.95 | 111.28 | 13.75 |
| Vadadustat-O-Glucuronide | | | | | | |
| $AUC_{last}$ (hr*μg/mL) | 83.81 | 37.41 | 224.05 | 207.73 | 241.66 | 13.10 |
| $AUC_{inf}$ (hr*μg/mL) | 86.58 | 38.24 | 226.39 | 208.92 | 245.33 | 13.92 |
| $C_{max}$ (μg/mL) | 6.17 | 5.59 | 110.38 | 105.06 | 115.97 | 8.53 |

$AUC_{inf}$: AUC from 0 to infinity;
$AUC_{last}$: AUC from 0 to last quantifiable concentration;
$C_{max}$: maximum observed plasma concentration;
CV %: coefficient of variation;
V: vadadustat;
V + P: vadadustat and probenecid
[1]90% Geometric Confidence Interval calculated according to the formula: exp(DIFFERENCE ± t(dfResidual) * SEDIFFERENCE) * 100.
[2]Calculated using least-square means according to the formula: exp(DIFFERENCE) * 100.
[3]Calculated according to formula: SQRT (exp (MSE) − 1) * 100. Probability (p) values were derived from Type III sums of squares.

When vadadustat was administered in combination with cyclosporine (an OATP1B1 and BCRP inhibitor), there were no clinically relevant changes in the $C_{max}$ and AUC values of vadadustat or vadadustat-O-glucuronide.

As cyclosporine, an OATP1B1 and BCRP inhibitor, did not alter the PK of vadadustat, further evaluation of the OATP1B1 inhibitor (IV single dose rifampin) was not warranted.

When vadadustat was administered in combination with probenecid (a UGT and OAT3 inhibitor), the AUC values for both vadadustat and vadadustat-O-glucuronide increased about 2-fold; whereas, the $C_{max}$ values were relatively unchanged. Urinary excretion decreased for both vadadustat and vadadustat-O-glucuronide.

As the AUC values for both vadadustat and vadadustat-O-glucuronide were increased similarly (ie. parent to metabolite ratio unchanged), it was concluded that the increase in vadadustat AUC was not due to UGT inhibition.

In general, vadadustat was tolerated by subjects during treatment with cyclosporine or probenecid.

Example 4: Administration of Digoxin or Adefovir with Compound 1

Investigators can prescribe a composition comprising a p-glycoprotein transport substrate (e.g., digoxin) and/or a substrate of OAT1 (e.g., adefovir) as needed to a patient taking Compound 1.

A Phase 1, open-label, fixed sequence study was conducted in healthy male and female subjects to evaluate vadadustat as a perpetrator of DDIs with digoxin and/or adefovir.

Following the screening period, subjects who meet all inclusion and no exclusion criteria described below were randomized in the subsequent clinic period.

Inclusion Criteria:

Subjects were to have met the following inclusion criteria to participate in the study:

1. Male or female between 18 and 55 years of age, inclusive, at time of informed consent.
   a. Female subjects of childbearing potential must be non-lactating, not pregnant as confirmed by a negative serum pregnancy test at Screening and Day −1, and using, and agree to continue using, an effective method of contraception for at least 4 weeks prior to first study drug administration the Screening visit until 30 days after the last dose of study drug.
   b. Female subjects of non-childbearing potential must be surgically sterile (e.g., hysterectomy, bilateral tubal ligation, oophorectomy) or post-menopausal (no menses for >1 year with follicle stimulating hormone [FSH]>40 U/L at Screening)
   c. Female subjects of childbearing potential must not donate ova during the study and for at least 30 days after the last dose of study drug.
   d. Male subjects who have not had a vasectomy must agree to use an effective method of contraception for at least 4 weeks prior to first study drug administration until 90 days after the last dose of the study drug, and to not donate sperm during the study and for at least 90 days after the last dose of study drug. See Appendix 16.1.1 for acceptable contraceptive use.
2. Healthy per investigator judgment as documented by medical history, physical examination, vital sign assessments, 12-lead ECG, clinical laboratory assessments, and general observations.
   a. At Screening, abnormalities or deviations outside the normal ranges for any clinical assessments (laboratory tests, ECG, vital signs) may be repeated once at the discretion of the investigator(s), and results that continue to be outside the normal ranges must be judged by the investigator to be not clinically significant and acceptable for study participation.
   b. On Day −1, alanine aminotransferase (ALT), aspartate aminotransferase (AST) and total bilirubin values must be within the upper limits of the normal range. All other laboratory test results that are outside the normal range on Day −1 and judged by the investigator to be not clinically significant may be repeated. Results that continue to be outside the normal range must be judged by the investigator to be not clinically significant and acceptable for study participation.

3. Body mass index between 18.0 and 30.0 kg/m2, with a minimum body weight of 45 kg for females, inclusive and 50 kg for males, inclusive.
4. Understands the procedures and requirements of the study and provides written informed consent and authorization for protected health information disclosure.
5. Willing and able to comply with the requirements of the study protocol.

Exclusion Criteria

Subjects who presented with any of the following were not to be entered into the study:

1. Current or past clinically significant history of cardiovascular, cerebrovascular, pulmonary, gastrointestinal, hematologic, renal, hepatic, immunologic, metabolic, urologic, neurologic, dermatologic, psychiatric, or other major disease, as determined by the investigator. History of cancer (except treated non-melanoma skin cancer) or history of chemotherapy use within 5 years prior to Screening.
2. Any surgical or medical condition or history that, in the opinion of the investigator, may potentially alter the absorption, metabolism, or excretion of study treatment, such as, but not limited to gastric bypass surgery or gastric or duodenal ulcers.
3. Contraindication to study drugs or its excipients and/or history of allergic or anaphylactic reactions.
4. Taking any of the following prohibited medications:
   a. Any prescription medication or over the counter multi-vitamin supplement, or any nonprescription products (including herbal-containing preparations but excluding acetaminophen) within 14 days prior to Day −1
   b. Any drug known to inhibit or induce cytochrome P450 (CYP) enzymes and/or p-glycoprotein including St. John's wort (*Hypericum perforatum*) within 14 days or 5 half-lives (whichever is longer) prior to Day −1
5. History of drug abuse within the previous year prior to Screening.
6. History of regular alcohol consumption exceeding 14 drinks/week [1 drink=5 ounces (150 mL) of wine or 12 ounces (360 mL) of beer or 1.5 ounces (45 mL) of hard liquor] within 6 months of Screening.
7. Positive drug and alcohol test at Screening or on Day −1.
8. Currently smoke 10 cigarettes or more per day
9. Consumed any food or drink/beverage containing of grapefruit or grapefruit juice, apple or orange juice, pomelo juice, star fruit, Seville or Moro (blood) orange products, and vegetables from the mustard green family (e.g., kale, broccoli, watercress, collard greens, kohlrabi, brussel sprouts, mustard), foods containing poppy seeds (e.g., muffins, bagels and cakes) 24 hours before Day −1 and charbroiled meats known to modulate CYP enzyme activity and transporters within 6 days before Day −1.
10. Positive test results of hepatitis B surface antigen (HBsAg), or positive hepatitis C virus antibody (HCVab) at Screening.
11. Positive test results for human immunodeficiency virus antibody (HIVab) within 3 months prior to Day −1 or at Screening.
12. Participation in another clinical trial or exposure to any investigational agent within 30 days or 5 half-lives prior to Day −1, whichever is longer.
13. Donation of blood or significant blood loss within 60 days, or plasma donation within 7 days prior to the first dose.
14. Received a tattoo or body piercing (including ear piercings) within 2 months prior to Day 1, and/or open wound that may result in risk of infection.
15. Having a condition that the investigator believes would interfere with his/her ability to provide written informed consent, comply with study instructions, or which might confound the interpretation of the study results or put the subject at undue risk.

Treatment of Subjects

Arm 1—Digoxin

On the morning of Day 1 subjects received a single oral dose of digoxin 0.5 mg after at least a 10-hour overnight fast. Subjects remained fasted for at least 4 hours after dosing. Following a 12-day washout period, subjects received vadadustat 600 mg QD beginning on Day 13 for 7 days (Days 13-19). When administered alone (Days 13-15 and Days 17-19), vadadustat was administered in the morning at least 30 minutes prior to breakfast. On Day 16 subjects received their morning dose of vadadustat 600 mg along with a single oral dose of digoxin 0.5 mg after at least a 10-hour fast.

Arm 2—Adefovir

On the morning of Day 1, subjects received a single oral dose of adefovir 10 mg after at least a 10-hour overnight fast. Subjects remained fasted for at least 4 hours after dosing. Following a 3-day washout period, subjects received vadadustat 600 mg QD beginning on Day 4 for 5 days (Days 4-8). When administered alone, vadadustat was administered in the morning at least 30 minutes prior to breakfast. On Day 7 subjects received their morning dose of vadadustat 600 mg along with a single oral dose of adefovir 10 mg after at least a 10-hour overnight fast.

Data Analysis

Figure 7A:
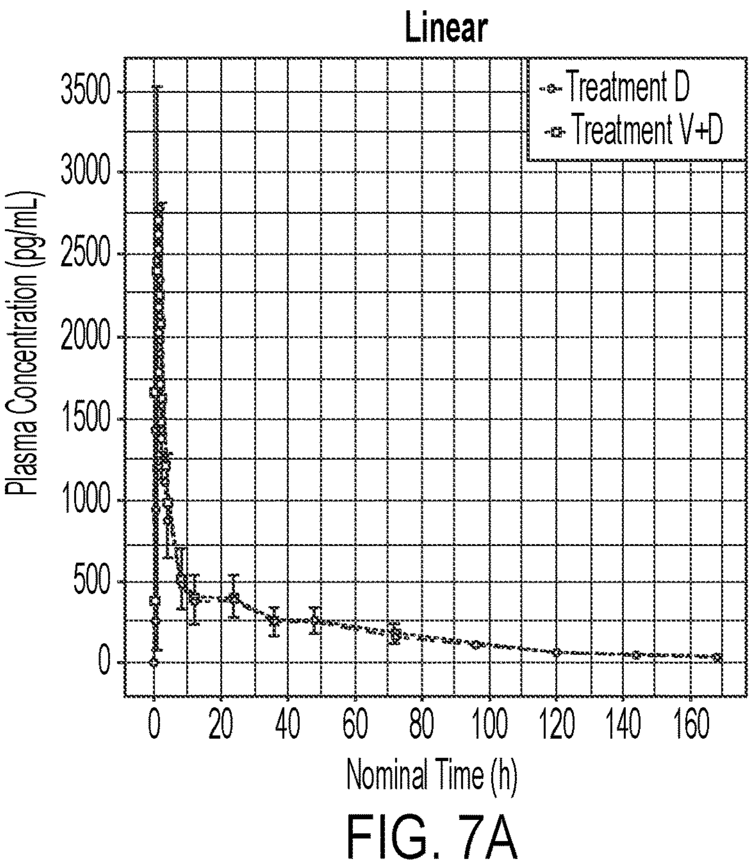
FIGS. 7*a*-7*b* show mean (SD) digoxin plasma concentrations (days 1 and 16) (Pharmacokinetic Population) when 1) 0.5 mg digoxin administered alone; and 2) 0.5 mg digoxin administered with 600 mg vadadustat.
Figure 7B:
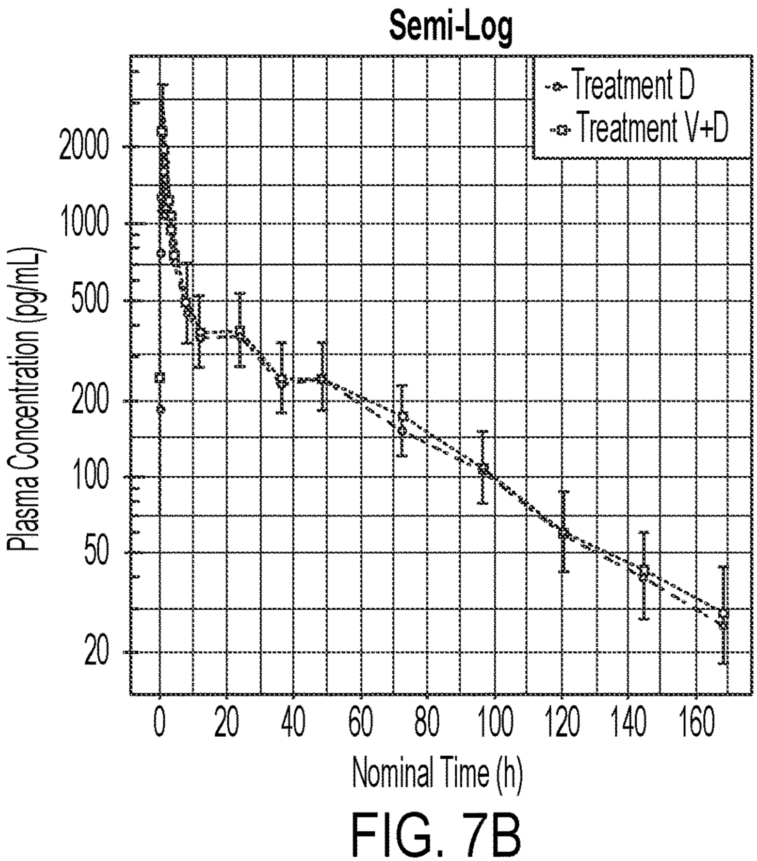

Plasma concentration-time profiles for digoxin alone and when coadministered with vadadustat are presented in FIG. 7*a*-7*b*.

Following treatment with digoxin alone or vadadustat plus digoxin, point estimates of the T/R mean ratios of the primary parameters $AUC_{last}$, $AUC_{inf}$, and $C_{max}$ for digoxin were 91.49%, 91.37%, and 66.92%, respectively (Table 9). Total exposure ($AUC_{last}$ and $AUC_{inf}$) to digoxin was unchanged when digoxin was administered following multiple doses of vadadustat compared to when digoxin was administered alone. Digoxin $C_{max}$ decreased by ~35% when digoxin and vadadustat were coadministered.

TABLE 9

Summary of plasma PK parameters for vadadustat following coadministration with Digoxin

| Parameter(unit) | Geometric LSM Treatment V + D | Geometric LSM Treatment D | Ratio (V + D)/D[1] (%) | 90% Geometric CI[2] Lower (%) | 90% Geometric CI[2] Upper (%) | Intra-Subject CV (%)[3] |
|---|---|---|---|---|---|---|
| $AUC_{last}$ (hr*ng/mL) | 31.69 | 34.63 | 91.49 | 85.41 | 98.01 | 11.52 |
| $AUC_{inf}$ (hr*ng/mL) | 33.19 | 36.32 | 91.37 | 85.20 | 97.99 | 11.72 |
| $C_{max}$ (ng/mL) | 1.64 | 2.46 | 66.92 | 60.52 | 74.00 | 17.47 |

$AUC_{inf}$: AUC from 0 to infinity;
$AUC_{last}$: AUC from 0 to last quantifiable concentration;
$C_{max}$: maximum observed plasma concentration;
CV: coefficient of variation;
LSM: Least Square Mean;
Treatment D: digoxin alone;
Treatment V + D: vadadustat + digoxin.
[1]Calculated using least-squares means according to the formula: exp (DIFFERENCE) * 100.
[2]90% Geometric Confidence Interval (CI) calculated according to the formula: exp (DIFFERENCE ± t(dfResidual) * SEDIFFERENCE) * 100
[3]Calculated according to formula: SQRT (exp (MSE) − 1) * 100.

Figure 8A:
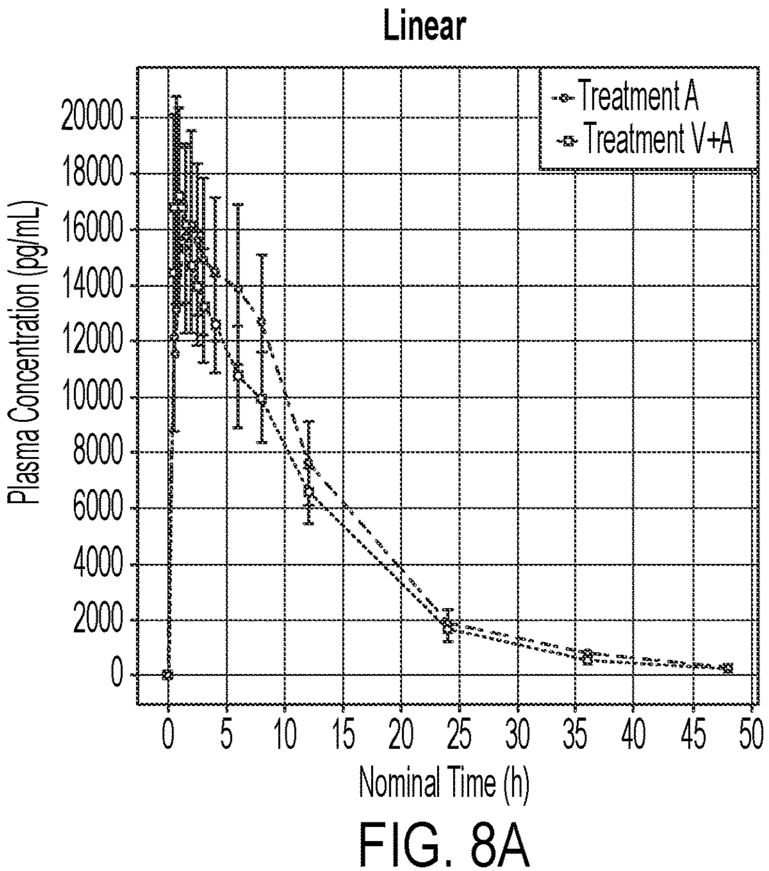
FIGS. 8*a*-8*b* show mean (SD) adefovir plasma concentrations (days 1 and 7) (Pharmacokinetic Population) when 1) 10 mg adefovir administered alone; and 2) 10 mg adefovir administered with 600 mg vadadustat.
Figure 8B:
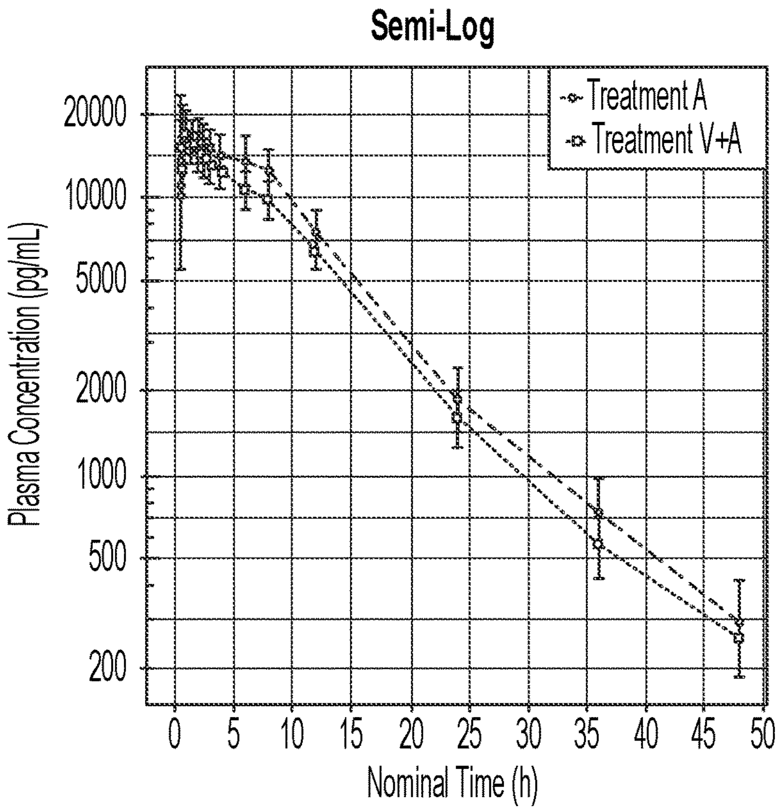

Plasma concentration-time profiles for adefovir alone and when coadministered with vadadustat are presented in FIG. 8*a*-8*b*.

Following treatment with adefovir alone or vadadustat plus adefovir, point estimates of the T/R mean ratios of the primary parameters $AUC_{last}$, $AUC_{inf}$, and $C_{max}$ for adefovir were 114.74%, 114.70%, and 95.15%, respectively. These data indicate that the systemic exposure to adefovir was relatively unchanged when adefovir was administered with vadadustat as compared to when adefovir was administered alone. Overall, these data indicated minimal interaction between vadadustat and adefovir (Table 10).

TABLE 10

Summary of plasma PK parameters for vadadustat following coadministration with Adefovir

| Parameter(unit) | Geometric LSM Treatment V + A | Geometric LSM Treatment A | Ratio (V + A)/A[1] (%) | 90% Geometric CI[2] Lower (%) | 90% Geometric CI[2] Upper (%) | Intra- Subject CV (%)[3] |
|---|---|---|---|---|---|---|
| $AUC_{last}$ (hr*ng/mL) | 226.75 | 197.62 | 114.74 | 108.83 | 120.97 | 7.92 |
| $AUC_{inf}$ (hr*ng/mL) | 230.17 | 200.66 | 114.70 | 108.82 | 120.90 | 7.88 |
| $C_{max}$ (ng/mL) | 17.07 | 17.94 | 95.15 | 86.27 | 104.95 | 14.72 |

$AUC_{inf}$: AUC from 0 to infinity;
$AUC_{last}$: AUC from 0 to last quantifiable concentration;
$C_{max}$: maximum observed plasma concentration;
LSM: Least Square Mean;
Treatment A: adefovir alone;
Treatment V + A: vadadustat + adefovir
[1]Calculated using least-squares means according to the formula: exp (DIFFERENCE) * 100.
[2]90% Geometric Confidence Interval (CI) calculated according to the formula: exp (DIFFERENCE ± t(dfResidual) * SEDIFFERENCE) * 100
[3]Calculated according to formula: SQRT (exp (MSE) − 1) * 100.

When vadadustat was administered in combination with digoxin, a p-glycoprotein transport substrate, total exposure ($AUC_{last}$ and $AUC_{inf}$) to digoxin was unchanged. Digoxin $C_{max}$ decreased by ~35% when digoxin and vadadustat were co-administered. A change in exposure <2-fold is considered a mild drug interaction per FDA 2017 guidance. These data suggest that vadadustat would likely have minimal interaction with other substrates of p-glycoprotein.

When vadadustat was administered in combination with adefovir, a substrate of OAT1, systemic exposure to adefovir was relatively unchanged; therefore, no interaction was noted between vadadustat and adefovir. These data suggest that vadadustat would likely have minimal interaction with other substrates of OAT1.

While a number of embodiments of this invention have been described, it is apparent that the basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

From the ongoing description, one skilled in the art can easily ascertain the essential characteristics of this invention, and without departing from the spirit and scope thereof, can make various changes and modifications of the invention to adapt it to various usages and conditions.

All references, patents or applications, U.S. or foreign, cited in the application are hereby incorporated by reference as if written herein in their entireties. Where any inconsistencies arise, material literally disclosed herein controls.

What is claimed is:

1. A method of reducing or minimizing drug-drug interaction between a first drug and a second drug comprising administering to a subject:

(a) an effective amount of the first drug or a pharmaceutical composition comprising an effective amount of the first drug, wherein the first drug is {[5-(3-chlorophenyl)-3-hydroxypyridine-2-carbonyl]amino}acetic acid (Compound 1), or a pharmaceutically acceptable salt thereof; and (b) an effective amount of the second drug, wherein the second drug comprises a polymeric amine that binds phosphate, wherein the second drug is sevelamer hydrochloride or sevelamer carbonate;

wherein the subject has anemia secondary to or associated with chronic kidney disease, and wherein (a) is administered to the subject at least 1 hour before and/or after (b) is administered to the subject, or wherein (a) is administered to the subject at least 2 hours before and/or after (b) is administered to the subject.

2. A method of increasing bioavailability of a first drug, or minimizing a decrease in the absorption of the first drug, comprising administering to a subject:

(a) an effective amount of the first drug or a pharmaceutical composition comprising an effective amount of the first drug, wherein the first drug is {[5-(3-chlorophenyl)-3-hydroxypyridine-2-carbonyl]amino}acetic acid (Compound 1), or a pharmaceutically acceptable salt thereof; and (b) an effective amount of a second drug that is a composition comprising a polymeric amine that binds to phosphate, wherein the second drug is sevelamer hydrochloride or sevelamer carbonate;

wherein the subject has anemia secondary to or associated with chronic kidney disease, and wherein (a) is administered to the subject at least 2 hours before and/or after (b) is administered to the subject; or wherein (a) is administered to the subject at least 1 hour before and/or after (b) is administered to the subject.

3. The method of claim 1, wherein the second drug is a sevelamer hydrochloride.

4. The method of claim 1, wherein the second drug is a sevelamer carbonate.

5. The method of claim 1, wherein (b) is administered as a tablet.

6. The method of claim 1, wherein (b) is administered as a powder.

7. The method of claim 1, wherein the first drug is administered to the subject at least 1 hour before the second drug is administered to the subject.

8. The method of claim 1, wherein the first drug is administered to the subject at least 2 hours after the second drug is administered to the subject.

9. The method of claim 2, wherein (a) is administered to the subject at least 1 hour before (b) is administered to the subject.

10. The method of claim 2, wherein (a) is administered to the subject at least 2 hours after (b) is administered to the subject.

11. A method of reducing or minimizing drug-drug interaction between a first drug and a second drug comprising administering to a subject:

(a) an effective amount of the first drug or a pharmaceutical composition comprising an effective amount of the first drug, wherein the first drug is {[5-(3-chlorophenyl)-3-hydroxypyridine-2-carbonyl]amino}acetic acid (Compound 1), or a pharmaceutically acceptable salt thereof; and (b) an effective amount of the second drug, wherein the second drug is an OAT1/OAT3 inhibitor that is probenecid, wherein the subject has anemia secondary to or associated with chronic kidney disease, and wherein the amount of (a) is adjusted compared to the amount when administered in the absence of (b) or in monotherapy.

12. The method of claim 11, wherein the subject is at risk of or has gout or gouty arthritis.

13. The method of claim 11, wherein (b) is administered as a tablet.

14. The methods of claim 11, wherein the amount of (a) is decreased compared to the amount when administered in the absence of (b) or in monotherapy.

15. The method of claim 14, wherein the amount of (a) is decreased by about 20% to about 80% compared to the amount when administered in the absence of (b) or in monotherapy.

16. The method of claim 15, wherein the amount of (a) is decreased by about 40% to about 60% compared to the amount when administered in the absence of (b) or in monotherapy.

17. A method of treating anemia secondary to or associated with chronic kidney disease in a subject, comprising administering to the subject an effective amount of a compound which is {[5-(3-chlorophenyl)-3-hydroxypyridine-2-carbonyl]amino}acetic acid (Compound 1), or pharmaceutically acceptable salt thereof, and wherein the compound is for administering together with a composition comprising a polymeric amine selected from sevelamer hydrochloride and sevelamer carbonate, or wherein the compound is for administering together with an OAT1/OAT3 inhibitor that is probenecid.

18. The method of claim 17, wherein the compound is administered at least 1 hour before administering the composition comprising a polymeric amine selected from sevelamer hydrochloride or sevelamer carbonate.

19. The method of claim 18, wherein the compound is administered at least 2 hours after administering the composition comprising a polymeric amine selected from sevelamer hydrochloride or sevelamer carbonate.

20. The methods of claim 17, wherein the amount of {[5-(3-chlorophenyl)-3-hydroxypyridine-2-carbonyl]amino}acetic acid (Compound 1), or pharmaceutically acceptable salt thereof, is decreased compared to the amount when administered in the absence of an OAT1/OAT3 inhibitor that is probenecid or in monotherapy.

21. A method of treating anemia due to chronic kidney disease in a subject having dialysis dependent renal anemia, comprising administering to the subject:

(a) an effective amount of a first drug comprising {[5-(3-chlorophenyl)-3-hydroxypyridine-2-carbonyl]amino}acetic acid (Compound 1), or pharmaceutically acceptable salt thereof, and (b) an effective amount of a second drug, wherein the second drug comprises sevelamer hydrochloride or sevelamer carbonate, and wherein the first drug is administered to the subject at least 1 hour before or at least 2 hours after the second drug.

22. The method of claim 21, wherein the first drug is administered to the subject at least 1 hour before the second drug.

23. The method of claim 21, wherein the first drug is administered to the subject at least 2 hours after the second drug.

24. A method of treating anemia due to chronic kidney disease in a subject having dialysis dependent renal anemia, comprising administering to the subject:

(a) an effective amount of a first drug comprising {[5-(3-chlorophenyl)-3-hydroxypyridine-2-carbonyl] amino}acetic acid (Compound 1), or pharmaceutically acceptable salt thereof, and (b) an effective amount of a second drug that comprises probenecid, and wherein the amount of the first drug is adjusted compared to the amount when administered in the absence of the second drug or in monotherapy.

25. The method of claim 24, wherein the amount of the first drug is increased compared to the amount when administered in the absence of the second drug or in monotherapy.

26. The method of claim 24, wherein the first drug is decreased compared to the amount when administered in the absence of the second drug or in monotherapy.

* * * * *